United States Patent
Lau et al.

(10) Patent No.: US 11,760,788 B2
(45) Date of Patent: Sep. 19, 2023

(54) NEURORECEPTOR COMPOSITIONS AND METHODS OF USE

(71) Applicant: Pathways Neuro Pharma, Inc., Tomball, TX (US)

(72) Inventors: Warren C. Lau, Tomball, TX (US); Brad Thompson, Calgary (CA)

(73) Assignee: Pathways Neuro Pharma, Inc., Tomball, TX (US)

( * ) Notice: Subject to any disclaimer, the term of this patent is extended or adjusted under 35 U.S.C. 154(b) by 336 days.

(21) Appl. No.: 17/190,322

(22) Filed: Mar. 2, 2021

(65) Prior Publication Data

US 2022/0281952 A1    Sep. 8, 2022

(51) Int. Cl.
*C12N 15/00* (2006.01)
*C07K 14/72* (2006.01)
*C12N 15/86* (2006.01)

(52) U.S. Cl.
CPC .............. *C07K 14/72* (2013.01); *C12N 15/86* (2013.01); *C12N 2750/14143* (2013.01); *C12N 2830/48* (2013.01); *C12N 2830/50* (2013.01)

(58) Field of Classification Search
CPC ..................... C07K 14/72; C12N 15/86; C12N 2750/14143; C12N 2830/48; C12N 2830/50
See application file for complete search history.

(56) References Cited

U.S. PATENT DOCUMENTS

| | | | |
|---|---|---|---|
| 5,478,745 A | 12/1995 | Samulski et al. | |
| 6,204,059 B1 | 3/2001 | Samulski et al. | |
| 6,566,118 B1 | 5/2003 | Atkinson et al. | |
| 9,441,206 B2 | 9/2016 | Grieger et al. | |
| 2007/0065801 A1* | 3/2007 | Golz | G01N 33/942 435/6.16 |
| 2016/0145218 A1 | 5/2016 | Hitchcock et al. | |
| 2018/0193414 A1* | 7/2018 | Greenberg | A61P 25/16 |

FOREIGN PATENT DOCUMENTS

| | | |
|---|---|---|
| WO | WO 96/40240 | 12/1996 |
| WO | WO 98/09657 | 3/1998 |
| WO | WO 2001/92551 | 12/2001 |
| WO | WO 2002/46359 | 6/2002 |
| WO | WO 2013/063379 | 5/2013 |

OTHER PUBLICATIONS

Alavi et al (Biomedicine & Pharmacotherapy vol. 98, 2018: pp. 222-232). (Year: 2018).*
Dizeyi et al (European Urology 2005 vol. 47, pp. 895-900). (Year: 2005).*
Yan et al (Cancer Communications 2020 vol. 40: pp. 694-710). (Year: 2020).*
Sobczuk et al (Cancers 2020 vol. 12: No. 3232: pp. 1-22). (Year: 2020).*
Andersen et al., "Protection of Primary Dopaminergic Midbrain Neurons by GPR139 Agonists Supports Different Mechanisms of Mpp+ and Rotenone Toxicity," Frontiers in Cellular Neuroscience, 10:164 (publication date: Jun. 2016).
Balazs et al., "Antibody-based protection against HIV infection by vectored immunoprophylaxis," Nature, vol. 481, 81-84 (publication date: Jan. 5, 2012).
Brown et al., "Chimeric Parvovirus B19 Capsids for the Presentation of Foreign Epitopes," Virology, 198(2):477-488 (publication date: Feb. 1994) Abstract.
Castellani et al., "Copy number variation distribution in six monozygotic twin pairs discordant for schizophrenia," Twin Res Hum Genet, 17(2):108-120 (publication date: Apr. 2014).
Clark et al., "Highly Purified Recombinant Adeno-Associated Virus Vectors Are Biologically Active and Free of Detectable Helper and Wild Type Viruses," Human Gene Therapy 10(6):1031-1039 (publication date: Apr. 10, 1999).
Codon Usage Database available at www.kazusa.or.jp/codon/ (visited Jun. 18, 2012).
Eugene G. Shpaer, "GeneAssist," Methods in Molecular Biology, 70:173-187 (1997).
GenBank Accession No. NM_000794.5 (first available at NCBI on Mar. 24, 1999).
GenBank Accession No. NP_000785.1 (first available at NCBI on Mar. 24, 1999).
GenBank Accession No. NP_000861.1 (first available at NCBI on Nov. 23, 2000).
GenBank Accession No. NP_001002911.1 (first available at NCBI on Aug. 3, 2004).
GenBank Accession No. NP_001035259.1 (first available at NCBI on Apr. 28, 2006).
GenBank Accession No. NP_001035262.2 (first available at NCBI on Apr. 28, 2006).
GenBank Accession No. NP_001035263.1 (first available at NCBI on Apr. 28, 2006).
GenBank Accession No. NP_001273339.1 (first available at NCBI on Nov. 5, 2013).
GenBank Accession No. NP_001305412.1 (first available at NCBI on Jan. 8, 2016).
Graham et al., "Characteristics of a Human Cell Line Transformed by DNA from Human Adenovirus Type 5," J. Gen. Virol., 36:59-72 (1977).
Grieger et al., "Production of Recombinant Adeno-associated Virus Vectors Using Suspension Hek293 Cells and Continuous Harvest of Vector From the Culture Media for CMP Fix and FLT1 Clinical Vector," Molecular Therapy, 24(2):287-297 (publication date: Feb. 2016).
Grimm et al., "Novel Tools for Production and Purification of Recombinant Adeno associated Virus Vectors," Human Gene Therapy 9:2745-2760 (publication date: Dec. 10, 1998).

(Continued)

*Primary Examiner* — Catherine S Hibbert
(74) *Attorney, Agent, or Firm* — Perkins Coie LLP

(57) ABSTRACT

Compositions and methods for the treatment of neurological disorders whereby vectors contain codon-optimized nucleic acids for expression in humans, encoding a human dopamine receptor D1 protein, a human 5-Hydroxytryptamine receptor 4 protein, and a human G-protein coupled receptor 139).

24 Claims, 43 Drawing Sheets

Specification includes a Sequence Listing.

(56) References Cited

OTHER PUBLICATIONS

Halbert et al., "AAV6 Vector Production and Purification for Muscle Gene Therapy," Methods Mol Biol, 1687:257-66 (2018) Abstract.
Halbert et al., "Efficient mouse airway transduction following recombination between AAV vectors carrying parts of a larger gene," Nat. Biotechnol., 20:697-701 (publication date: Jul. 2002).
Hu et al., "Identification of Surrogate Agonists and Antagonists for Orphan G-Protein-Coupled Receptor GPR139," Journal of Biomolecular Screening, 14(7):789-797 (2009).
Kajigaya et al., "Self-assembled B19 parvovirus capsids, produced in a baculovirus system, are antigenically and immunogenically similar to native virions," Proc. Nat'l. Acad. Sci. USA 88(11):4646-4650 (publication date: Jun. 1, 1991) Abstract.
Kimbauer et al., "Virus-like Particles of Bovine Papillomavirus Type 4 in Prophylactic and Therapeutic Immunization," Virology, 219:37-44 (1996).
Kononoff et al., "Systemic and Intra-Habenular Activation of the Orphan G Protein—Coupled Receptor GPR139 Decreases Compulsive-Like Alcohol Drinking and Hyperalgesia in Alcohol-Dependent Rats," eNeuro, e0153-18:2018 1-14 (publication date: May/Jun. 2018).
Liu et al., "GPR139, an Orphan Receptor Highly Enriched in the Habenula and Septum, Is Activated by the Essential Amino Acids L-Tryptophan and L-Phenylalanine," Mol. Pharmacol., 88:911-925 (publication date: Nov. 2015).
Miyazaki et al., "Expression vector system based on the chicken α-actin promoter directs efficient production of interleukin-5," Gene, 79:269-277 (1989).
Nakamura et al., "Codon usage tabulated from international DNA sequence database: status for the year 2000," Nucleic Acids Research, 28(1):292 (2000).
Needleman et al., "A General Method Applicable to the Search for Similarities in the Amino Acid Sequence of Two Proteins," J. Mol. Biol. 48:443-453 (1970).
Rabinowitz et al., "Cross-packaging of a single adeno-associated virus (AAV) type 2 vector genome into multiple AAV serotypes enables transduction with broad specificity," J Virol., 76(2):791-801.
Ruffing et al., "Assembly of Viruslike Particles by Recombinant Structural Proteins of Adeno-Associated Virus Type 2 in Insect Cells," Journal of Virology, p. 6922-6930 (publication date: Dec. 1992).
Samulski et al., "Helper-Free Stocks of Recombinant Adeno-Associated Viruses: Normal Integration Does Not Require Viral Gene Expression," Journal of Virology, p. 3822-3828 (publication date: Sep. 1989).
Schenpp et al., "Highly purified recombinant adeno-associated virus vectors," Preparation and Quantitation, Gene Therapy Protocols, 427-443 (2002) Abstract.
Sharp et al., "The codon adaptation index—a measure of directional synonymouscodon usage bias, and its potential applications," Nucleic Acids Research, 15:1281-1295 (publication date: Nov. 3, 1987).
Shi et al., "Discovery and SAR of a Series of Agonists at Orphan G Protein-Coupled Receptor 139," ACS Med Chem Lett, 2(4):303-306 (publication date: Feb. 28, 2011).
Urabe et al., "Insect Cells as a Factory to Produce Adeno-Associated Virus Type 2 Vectors," Human Gene Therapy, 13:1935-1943 (publication date: Nov. 1, 2002).
Xiao et al., "A Novel 165-Base-Pair Terminal Repeat Sequence Is the Sole cis Requirement for the Adeno-Associated Virus Life Cycle," Journal of Virology, p. 941-948 (publication date: Feb. 1997).
Zhao et al., "BPV1 E2 protein enhances packaging of full-length plasmid DNA in BPV1 pseudovirions," Virol. 272(2):382-393 (publication date: 2000) Abstract.

\* cited by examiner

FIGURE 1

Sequence: pACASI-GFP-F2A-DRD1-HA-optimized.dna

```
5'   CAGCAGCTGCGCGCTCGCTCGCTCACTGAGGCCGCCCGGGCAAAGCCCGGGCGTCGGGCGACCTT
     ················································································  65
3'   GTCGTCGACGCGCGAGCGAGCGAGTGACTCCGGCGGGCCCGTTTCGGGCCCGCAGCCCGCTGGAA
                                    RBE

TGGTCGCCCGGCCTCAGTGAGCGAGCGAGCGCGCAGAGAGGGAGTGGCCAACTCCATCACTAGGG
     ················································································  130
     ACCAGCGGGCCGGAGTCACTCGCTCGCTCGCGCGTCTCTCCCTCACCGGTTGAGGTAGTGATCCC
                                    RBE

GTTCCTTGTAGTTAATGATTAACCCGCCATGCTACTTATCTACGTAGCCATGCTCTAGGACATTG
     ················································································  195
     CAAGGAACATCAATTACTAATTGGGCGGTACGATGAATAGATGCATCGGTACGAGATCCTGTAAC

SpeI
     ATTATTGACTAGTggagttccgcgttacataacttacggtaaatggcccgcctggctgaccgccc
     ················································································  260
     TAATAACTGATCAcctcaaggcgcaatgtattgaatgccatttaccgggcggaccgactggcggg
                                    CASI promoter
                                    CMV enhancer aacgaccccgcccattgacgtcaataatgacgtatgttcccatagtaacgccaatagggactt t
     ················································································  325
     ttgctggggcgggtaactgcagttattactgcatacaagggtatcattgcggttatccctgaaa
                                    CASI promoter
                                    CMV enhancer ccattgacgtcaatgggtggagtatttacggtaaactgcccacttggcagtacatcaagtgtatc
     ················································································  390
     ggtaactgcagttacccacctcataaatgccatttgacgggtgaaccgtcatgtagttcacatag
                                    CASI promoter
                                    CMV enhancer atatgccaagtacgccccctattgacgtcaatgacggtaaatggcccgcctggcattatgccag
     ················································································  455
     tatacggttcatgcggggataactgcagttactgccatttaccgggcggaccgtaatacgggtc
                                    CASI promoter
                                    CMV enhancer tacatgaccttatgggactttcctacttggcagtacatctacgtattagtcatcgctattaccat
     ················································································  520
     atgtactggaataccctgaaaggatgaaccgtcatgtagatgcataatcagtagcgataatggta
                                    CASI promoter
                                    CMV enhancer
```

FIGURE 1 Continued

```
       ggtcgaggtgagccccacgttctgcttcactctccccatctccccccctccccaccccaattt
       ----+----|----+----|----+----|----+----|----+----|----+----|----   585
       ccagctccactcggggtgcaagacgaagtgagaggggtagaggggggggaggggtggggttaaa
                                  CASI promoter
       ]──────────────────────── chicken β-actin promoter ────────────────>
CMV enhancer tgtatttatttatttttaattatttgtgcagcgatggggggcggggggggggggggcgcgcgc
       ----+----|----+----|----+----|----+----|----+----|----+----|----   650
       acataaataaataaaaattaataaaacacgtcgctaccccgccccccccccccgcgcgcg
                                  CASI promoter
       ──────────────────────── chicken β-actin promoter ────────────────> caggcggggcggggcggggcgaggggcggggcggggcgaggcggagaggtgcggcggcagccaat
       ----+----|----+----|----+----|----+----|----+----|----+----|----   715
       gtccgccccgccccgccccgctccccgccccgcccgctccgcctctccacgccgccgtcggtta
                                  CASI promoter
       ──────────────────────── chicken β-actin promoter ────────────────> cagagcggcgcgctccgaaagtttccttttatggcgaggcggcggcggcggccctataaaaa
       ----+----|----+----|----+----|----+----|----+----|----+----|----   780
       gtctcgccgcgcgaggctttcaaaggaaaataccgctccgccgccgccgccgggatatttttt
                                  CASI promoter
       ──────────────────────── chicken β-actin promoter ────────────────> gcgaagcgcgcggcgggcgggagtcgctgcgcgctgccttcgccccgtgccccgctccgccgccg
       ----+----|----+----|----+----|----+----|----+----|----+----|----   845
       cgcttcgcgcgccgcccgccctcagcgacgcgcgacggaagcggggcacggggcgaggcggcggc
                                  CASI promoter
       ┈┈┈┈┈chicken β-actin promoter┈┈┈┈> cctcgcgccgcccgccccggctctgactgaccgcgttactaaaacaggtaagtccggcctccgcg
       ----+----|----+----|----+----|----+----|----+----|----+----|----   910
       ggagcgcggcgggcggggccgagactgactggcgcaatgattttgtccattcaggccggaggcgc
                                  CASI promoter AfeI
       ccgggttttggcgcctccgcgggcgcccccctcctcacggcgagcgctgccacgtcagacgaag
       ----+----|----+----|----+----|----+----|----+----|----+----|----   975
       ggcccaaaaccgcggagggcgcccgcggggggaggagtgccgctcgcgacggtgcagtctgcttc
                                  CASI promoter ggcgcagcgagcgtcctgatccttccgcccggacgctcaggacagcggcccgctgctcataagac
       ----+----|----+----|----+----|----+----|----+----|----+----|----   1040
       ccgcgtcgctcgcaggactaggaaggcgggcctgcgagtcctgtcgccgggcgacgagtattctg
                                  CASI promoter tcggccttagaaccccagtatcagcagaaggacattttaggacgggacttgggtgactctagggc
       ----+----|----+----|----+----|----+----|----+----|----+----|----   1105
       agccggaatcttggggtcatagtcgtcttcctgtaaaatccgcctgaacccactgagatcccg
                                  CASI promoter
```

FIGURE 1 Continued

```
actggttttctttccagagagcggaacaggcgaggaaaagtagtcccttctcggcgattctgcgg
                                                                              1170
tgaccaaaagaaaggtctctcgccttgtccgctccttttcatcagggaagagccgctaagacgcc
                                    CASI promoter agggatctccgtggggcggtgaacgccgatgatgcctctactaaccatgttcatgttttctttt
                                                                              1235
tccctagaggcaccccgccacttgcggctactacggagatgattggtacaagtacaaaagaaaa
                                    CASI promoter Acc65I   KpnI
ttttctacaggtcctgggtgacgaacagGGTACCGCCACCATGGTGTCCAAGGGAGAGGAGCTGT
                                                                              1300
aaaagatgtccaggacccactgcttgtcCCATGGCGGTGGTACCACAGGTTCCCTCTCCTCGACA
                                                       1           5
                                                       M V S K G E E L
                    CASI promoter       KpnI   Kozak   eGFP mouse-human codon optimized TCACCGGAGTGGTGCCCATCCTGGTGGAGCTGGACGGCGATGTGAATGGCCACAAGTTTAGCGTG
                                                                              1365
AGTGGCCTCACCACGGGTAGGACCACCTCGACCTGCCGCTACACTTACCGGTGTTCAAATCGCAC
     10          15          20          25          30
  F T G V V P I L V E L D G D V N G H K F S V
                     eGFP mouse-human codon optimized BspEI
TCCGGAGAGGGAGAGGGCGACGCAACCTACGGCAAGCTGACACTGAAGTTCATCTGCACCACAGG
                                                                              1430
AGGCCTCTCCCTCTCCCGCTGCGTTGGATGCCGTTCGACTGTGACTTCAAGTAGACGTGGTGTCC
    35          40          45          50
 S G E G E G D A T Y G K L T L K F I C T T G
                     eGFP mouse-human codon optimized BstEII
CAAGCTGCCCGTGCCTTGGCCAACCCTGGTGACCACACTGACATACGGCGTGCAGTGTTTTCTC
                                                                              1495
GTTCGACGGGCACGGAACCGGTTGGGACCACTGGTGTGACTGTATGCCGCACGTCACAAAAGAG
    55          60          65          70
  K L P V P W P T L V T T L T Y G V Q C F S
                     eGFP mouse-human codon optimized GGTATCCAGACCACATGAAGCAGCACGATTTCTTTAAGAGCGCCATGCCCGAGGGCTACGTGCAG
                                                                              1560
CCATAGGTCTGGTGTACTTCGTCGTGCTAAAGAAATTCTCGCGGTACGGGCTCCCGATGCACGTC
    75          80          85          90          95
  R Y P D H M K Q H D F F K S A M P E G Y V Q
                     eGFP mouse-human codon optimized GAGAGGACAATCTTCTTTAAGGACGATGGCAACTATAAGACCAGAGCCGAGGTGAAGTTCGAGGG
                                                                              1625
CTCTCCTGTTAGAAGAAATTCCTGCTACCGTTGATATTCTGGTCTCGGCTCCACTTCAAGCTCCC
        100         105         110         115
  E R T I F F K D D G N Y K T R A E V K F E G
                     eGFP mouse-human codon optimized CGACACACTGGTGAACCGGATCGAGCTGAAGGGCATCGACTTTAAGGAGGATGGCAATATCCTGG
                                                                              1690
GCTGTGTGACCACTTGGCCTAGCTCGACTTCCCGTAGCTGAAATTCCTCCTACCGTTATAGGACC
        120         125         130         135
  D T L V N R I E L K G I D F K E D G N I L
                     eGFP mouse-human codon optimized
```

FIGURE 1 Continued

```
                                              BsrGI
GCCACAAGCTGGAGTACAACTATAATTCCCACAACGTGTACATCATGGCCGATAAGCAGAAGAAC
CGGTGTTCGACCTCATGTTGATATTAAGGGTGTTGCACATGTAGTACCGGCTATTCGTCTTCTTG       1755
         140         145         150         155         160
    G  H  K  L  E  Y  N  Y  N  S  H  N  V  Y  I  M  A  D  K  Q  K  N
                       eGFP mouse-human codon optimized GGCATCAAGGTGAACTTCAAGATCCGCCACAATATCGAGGACGGCTCTGTGCAGCTGGCCGATCA
CCGTAGTTCCACTTGAAGTTCTAGGCGGTGTTATAGCTCCTGCCGAGACACGTCGACCGGCTAGT       1820
         165         170         175         180
    G  I  K  V  N  F  K  I  R  H  N  I  E  D  G  S  V  Q  L  A  D  H
                       eGFP mouse-human codon optimized AccI
CTACCAGCAGAACACCCCTATCGGCGACGGACCCGTGCTGCTGCCTGATAATCACTATCTGTCTA
GATGGTCGTCTTGTGGGGATAGCCGCTGCCTGGGCACGACGACGGACTATTAGTGATAGACAGAT       1885
         185         190         195         200
    Y  Q  Q  N  T  P  I  G  D  G  P  V  L  L  P  D  N  H  Y  L  S
                       eGFP mouse-human codon optimized CACAGAGCGCCCTGTCCAAGGACCCAAACGAGAAGAGGGATCACATGGTGCTGCTGGAGTTCGTG
GTGTCTCGCGGGACAGGTTCCTGGGTTTGCTCTTCTCCCTAGTGTACCACGACGACCTCAAGCAC       1950
         205         210         215         220         225
    T  Q  S  A  L  S  K  D  P  N  E  K  R  D  H  M  V  L  L  E  F  V
                       eGFP mouse-human codon optimized ACCGCAGCAGGCATCACACTGGGCATGGATGAGCTGTATAAGcgaaaaagaagatcaggttcggg
TGGCGTCGTCCGTAGTGTGACCCGTACCTACTCGACATATTCgcttttttcttctagtccaagccc     2015
         230         235                     1         5
    T  A  A  G  I  T  L  G  M  D  E  L  Y  K  R  K  R  R  S  G  S  G
          eGFP mouse-human codon optimized              F2A optimized AarI
                      BfuAI
                      BspMI
tgcgccagtaaagcagacattaaactttgatttgctgaaacttgcaggtgatgtagagtcaaatc
acgcggtcatttcgtctgtaatttgaaactaaacgactttgaacgtccactacatctcagtttag       2080
     10         15         20         25
    A  P  V  K  Q  T  L  N  F  D  L  L  K  L  A  G  D  V  E  S  N
                                  F2A optimized BamHI
caggtccaggGATCCATGAGGACACTGAATACCTCTGCCATGGATGGCACAGGCCTGGTGGTGGAG
gtccaggtCCTAGGTACTCCTGTGACTTATGGAGACGGTACCTACCGTGTCCGGACCACCACCTC       2145
 30        1         1         5         10         15
  P  G  P  G  S  M  R  T  L  N  T  S  A  M  D  G  T  G  L  V  V  E
  F2A optimized   BamHI          DRD1A mouse-human codon optimized AGGGACTTTAGCGTGAGAATCCTGACCGCCTGCTTCCTGAGCCTGCTGATCCTGTCCACACTGCT
TCCCTGAAATCGCACTCTTAGGACTGGCGGACGAAGGACTCGGACGACTAGGACAGGTGTGACGA       2210
         20         25         30         35
    R  D  F  S  V  R  I  L  T  A  C  F  L  S  L  L  I  L  S  T  L  L
                       DRD1A mouse-human codon optimized
```

FIGURE 1 Continued

```
GGGCAATACCCTGGTGTGCGCCGCCGTGATCCGGTTTCGCCACCTGAGATCCAAGGTGACAAACT
CCCGTTATGGGACCACACGCGGCGGCACTAGGCCAAAGCGGTGGACTCTAGGTTCCACTGTTTGA    2275
        40            45            50            55            60
     G  N  T  L  V  C  A  A  V  I  R  F  R  H  L  R  S  K  V  T  N
                    DRD1A mouse-human codon optimized                →

TCTTTGTGATCAGCCTGGCCGTGTCCGATCTGCTGGTGGCCGTGCTGGTCATGCCTTGGAAGGCA
AGAAACACTAGTCGGACCGGCACAGGCTAGACGACCACCGGCACGACCAGTACGGAACCTTCCGT    2340
         65            70            75            80
  F  F  V  I  S  L  A  V  S  D  L  L  V  A  V  L  V  M  P  W  K  A
                    DRD1A mouse-human codon optimized                →

EcoRV
GTGGCAGAGATCGCAGGATTCTGGCCATTTGGCTCTTTCTGCAATATCTGGGTGGCCTTCGATAT
CACCGTCTCTAGCGTCCTAAGACCGGTAAACCGAGAAAGACGTTATAGACCCACCGGAAGCTATA    2405
          85            90            95           100
     V  A  E  I  A  G  F  W  P  F  G  S  F  C  N  I  W  V  A  F  D  I
                    DRD1A mouse-human codon optimized                →

AgeI
CATGTGCTCCACCGCCTCTATCCTGAACCTGTGCGTGATCAGCGTGGACCGGTACTGGGCCATCA
GTACACGAGGTGGCGGAGATAGGACTTGGACACGCACTAGTCGCACCTGGCCATGACCCGGTAGT    2470
       105           110           115           120           125
     M  C  S  T  A  S  I  L  N  L  C  V  I  S  V  D  R  Y  W  A  I
                    DRD1A mouse-human codon optimized                →

GCTCCCCCTTCAGGTACGAGAGAAAGATGACACCCAAGGCCGCCTTCATCCTGATCAGCGTGGCC
CGAGGGGGAAGTCCATGCTCTCTTTCTACTGTGGGTTCCGGCGGAAGTAGGACTAGTCGCACCGG    2535
          130           135           140           145
  S  S  P  F  R  Y  E  R  K  M  T  P  K  A  A  F  I  L  I  S  V  A
                    DRD1A mouse-human codon optimized                →

TGGACCCTGTCTGTGCTGATCAGCTTTATCCCCGTGCAGCTGTCCTGGCACAAGGCCAAGCCCAC
ACCTGGGACAGACACGACTAGTCGAAATAGGGGCACGTCGACAGGACCGTGTTCCGGTTCGGGTG    2600
        150           155           160           165
    W  T  L  S  V  L  I  S  F  I  P  V  Q  L  S  W  H  K  A  K  P  T
                    DRD1A mouse-human codon optimized                →

AAGCCCTTCCGACGGCAATGCCACATCTCTGGCCGAGACCATCGATAACTGTGACTCTAGCCTGA
TTCGGGAAGGCTGCCGTTACGGTGTAGAGACCGGCTCTGGTAGCTATTGACACTGAGATCGGACT    2665
       170           175           180           185           190
     S  P  S  D  G  N  A  T  S  L  A  E  T  I  D  N  C  D  S  S  L
                    DRD1A mouse-human codon optimized                →

GCCGCACCTACGCCATCTCCTCTAGCGTGATCTCCTTCTATATCCCTGTGGCCATCATGATCGTG
CGGCGTGGATGCGGTAGAGGAGATCGCACTAGAGGAAGATATAGGGACACCGGTAGTACTAGCAC    2730
       195           200           205           210
   S  R  T  Y  A  I  S  S  V  I  S  F  Y  I  P  V  A  I  M  I  V
                    DRD1A mouse-human codon optimized                →
```

FIGURE 1 Continued

```
ACATACACCCGGATCTATCGCATCGCCCAGAAGCAGATCAGGAGAATCGCCGCCCTGGAGAGGGC
TGTATGTGGGCCTAGATAGCGTAGCGGGTCTTCGTCTAGTCCTCTTAGCGGCGGGACCTCTCCCG
       215         220         225         230
   T  Y  T  R  I  Y  R  I  A  Q  K  Q  I  R  R  I  A  A  L  E  R  A
                    DRD1A mouse-human codon optimized                     >
                                                                        2795

AGCAGTGCACGCCAAGAATTGCCAGACCACAACCGGCAACGGCAAGCCTGTGGAGTGTTCTCAGC
TCGTCACGTGCGGTTCTTAACGGTCTGGTGTTGGCCGTTGCCGTTCGGACACCTCACAAGAGTCG
     235         240         245         250         255
   A  V  H  A  K  N  C  Q  T  T  T  G  N  G  K  P  V  E  C  S  Q
                    DRD1A mouse-human codon optimized                     >
                                                                        2860

CAGAGTCCTCTTTCAAGATGAGCTTTAAGAGAGAGACAAAGGTGCTGAAGACCCTGTCCGTGATC
GTCTCAGGAGAAAGTTCTACTCGAAATTCTCTCTCTGTTTCCACGACTTCTGGGACAGGCACTAG
       260         265         270         275
   P  E  S  S  F  K  M  S  F  K  R  E  T  K  V  L  K  T  L  S  V  I
                    DRD1A mouse-human codon optimized                     >
                                                                        2925

ATGGGCGTGTTCGTGTGCTGTTGGCTGCCTTTCTTTATCCTGAATTGCATCCTGCCATTTTGTGG
TACCCGCACAAGCACACGACAACCGACGGAAAGAAATAGGACTTAACGTAGGACGGTAAAACACC
         280         285         290         295
   M  G  V  F  V  C  C  W  L  P  F  F  I  L  N  C  I  L  P  F  C  G
                    DRD1A mouse-human codon optimized                     >
                                                                        2990

CTCCGGCGAGACACAGCCCTTCTGCATCGATTCTAACACCTTTGACGTGTTCGTGTGGTTTGGCT
GAGGCCGCTCTGTGTCGGGAAGACGTAGCTAAGATTGTGGAAACTGCACAAGCACACCAAACCGA
     300         305         310         315         320
   S  G  E  T  Q  P  F  C  I  D  S  N  T  F  D  V  F  V  W  F  G
                    DRD1A mouse-human codon optimized                     >
                                                                        3055

GGGCCAATAGCTCCCTGAACCCTATCATCTACGCCTTCAATGCCGATTTTCGGAAGGCCTTCAGC
CCCGGTTATCGAGGGACTTGGGATAGTAGATGCGGAAGTTACGGCTAAAAGCCTTCCGGAAGTCG
       325         330         335         340
   W  A  N  S  S  L  N  P  I  I  Y  A  F  N  A  D  F  R  K  A  F  S
                    DRD1A mouse-human codon optimized                     >
                                                                        3120

ACCCTGCTGGGCTGCTATCGCCTGTGCCCAGCCACAAACAATGCCATCGAGACCGTGTCCATCAA
TGGGACGACCCGACGATAGCGGACACGGGTCGGTGTTTGTTACGGTAGCTCTGGCACAGGTAGTT
     345         350         355         360
   T  L  L  G  C  Y  R  L  C  P  A  T  N  N  A  I  E  T  V  S  I  N
                    DRD1A mouse-human codon optimized                     >
                                                                        3185

CAATAACGGCGCCGCCATGTTCTCTAGCCACCACGAGCCCCGGGGCTCTATCAGCAAGGAGTGTA
GTTATTGCCGCGGCGGTACAAGAGATCGGTGGTGCTCGGGGCCCCGAGATAGTCGTTCCTCACAT
     365         370         375         380         385
   N  N  G  A  A  M  F  S  S  H  H  E  P  R  G  S  I  S  K  E  C
                    DRD1A mouse-human codon optimized                     >
                                                                        3250

SexAI*
ACCTGGTGTACCTGATCCCTCACGCCGTGGGCTCCTCTGAGGACCTGAAGAAGGAGGAGGCAGCA
TGGACCACATGGACTAGGGAGTGCGGCACCCGAGGAGACTCCTGGACTTCTTCCTCCTCCGTCGT
       390         395         400         405
   N  L  V  Y  L  I  P  H  A  V  G  S  S  E  D  L  K  K  E  E  A  A
                    DRD1A mouse-human codon optimized                     >
                                                                        3315
```

FIGURE 1 Continued

```
GGAATCGCAAGGCCCCTGGAGAAGCTGTCCCCTGCCCTGTCTGTGATCCTGGACTACGATACCGA
CCTTAGCGTTCCGGGGACCTCTTCGACAGGGGACGGGACAGACACTAGGACCTGATGCTATGGCT
         410           415            420            425
    G  I  A  R  P  L  E  K  L  S  P  A  L  S  V  I  L  D  Y  D  T  D
              DRD1A mouse-human codon optimized                        >
                                                                              3380

CGTGAGCCTGGAGAAGATCCAGCCAATCACACAGAACGGCCAGCACCCAACCTACCCCTATGATG
GCACTCGGACCTCTTCTAGGTCGGTTAGTGTGTCTTGCCGGTCGTGGGTTGGATGGGGATACTAC
    430           435            440            445
 V  S  L  E  K  I  Q  P  I  T  Q  N  G  Q  H  P  T  Y  P  Y  D
              DRD1A mouse-human codon optimized              >      >
                                                                              3445

XbaI
TGCCCGACTATGCCTGACTCTAGAAtaatcaacctctggattacaaaatttgtgaaagattgact
ACGGGCTGATACGGACTGAGATCTTattagttggagacctaatgtttaaacactttctaactga
   5
 V  P  D  Y  A    ☒
                        [  XbaI  ]    [              WPRE              ]
                                                                              3510 ggtattcttaactatgttgctccttttacgctatgtggatacgctgctttaatgcctttgtatca
ccataagaattgatacaacgaggaaaatgcgatacacctatgcgacgaaattacggaaacatagt
                              WPRE
                                                                              3575 tgctattgcttccgtatggctttcattttctcctccttgtataaatcctggttgctgtctcttt
acgataacgaagggcataccgaaagtaaagaggaggaacatatttaggaccaacgacagagaaa
                              WPRE
                                                                              3640 atgaggagttgtggcccgttgtcaggcaacgtggcgtggtgtgcactgtgtttgctgacgcaacc
tactcctcaacaccgggcaacagtccgttgcaccgcaccacacgtgacacaaacgactgcgttgg
                              WPRE
                                                                              3705 cccactggttggggcattgccaccacctgtcagctcctttccgggactttcgctttccccctccc
gggtgaccaacccgtaacggtggtggacagtcgaggaaaggccctgaaagcgaaaggggagggg
                              WPRE
                                                                              3770 tattgccacggcggaactcatcgccgcctgccttgcccgctgctggacaggggctcggctgttgg
ataacggtgccgccttgagtagcggcggacggaacgggcgacgacctgtcccgagccgacaacc
                              WPRE
                                                                              3835 gcactgacaattccgtggtgttgtcggggaaatcatcgtcctttccttggctgctcgcctgtgtt
cgtgactgttaaggcaccacaacagccccttagtagcaggaaaggaaccgacgagcggacacaa
                        ☒ R  G  K  R  P  Q  E  G  T  N
                        ◄─── (in frame with Factor Xa site) ────►
                              WPRE
                                                                              3900
```

FIGURE 1 Continued

```
gccacctggattctgcgcgggacgtccttctgctacgtcccttcggccctcaatccagcggacct
                                                                                    3965
cggtggacctaagacgcgccctgcaggaagacgatgcagggaagccgggagttaggtcgcctgga G  G  P  N  Q  A  P  R  G  E  A  V  D  R   R  G  E  I
←----------- (in frame with Factor Xa site) -----------◄ Factor Xa site
                            WPRE
```

```
tccttcccgcggcctgctgccggctctgcggcctcttccgcgtcttcgccttcgccctcagacga
                                                                                    4030
aggaagggcgccggacgacggccgagacgccggagaaggcgcagaagcggaagcgggagtctgct
                            WPRE
```

```
                                    HindIII                    BglII
gtcggatctcccttttgggccgcctccccgcctAAGCTTATCGATACCGTCGAGATCTAACTTGTT
                                                                                    4095
cagcctagagggaaacccggcggaggggcggaTTCGAATAGCTATGGCAGCTCTAGATTGAACAA
             WPRE                                            SV40 poly(A) signal
```

```
TATTGCAGCTTATAATGGTTACAAATAAAGCAATAGCATCACAAATTTCACAAATAAAGCATTTT
                                                                                    4160
ATAACGTCGAATATTACCAATGTTTATTTCGTTATCGTAGTGTTTAAAGTGTTTATTTCGTAAAA
                            SV40 poly(A) signal
```

```
  BsmI
TTTCACTGCATTCTAGTTGTGGTTTGTCCAAACTCATCAATGTATCTTATCATGTCTGGATCTCG
                                                                                    4225
AAAGTGACGTAAGATCAACACCAAACAGGTTTGAGTAGTTACATAGAATAGTACAGACCTAGAGC
                            SV40 poly(A) signal
```

```
ACCTCGACTAGAGCATGGCTACGTAGATAAGTAGCATGGCGGGTTAATCATTAACTACAAGGAAC
                                                                                    4290
TGGAGCTGATCTCGTACCGATGCATCTATTCATCGTACCGCCCAATTAGTAATTGATGTTCCTTG
```

```
CCCTAGTGATGGAGTTGGCCACTCCCTCTCTGCGCGCTCGCTCGCTCACTGAGGCCGGGCGACCA
                                                                                    4355
GGGATCACTACCTCAACCGGTGAGGGAGAGACGCGCGAGCGAGCGAGTGACTCCGGCCCGCTGGT
```

```
AAGGTCGCCCGACGCCCGGGCTTTGCCCGGGCGGCCTCAGTGAGCGAGCGAGCGCGCCAGCTGGC
                                                                                    4420
TTCCAGCGGGCTGCGGGCCCGAAACGGGCCCGCCGGAGTCACTCGCTCGCTCGCGCGGTCGACCG
```

```
GTAATAGCGAAGAGGCCCGCACCGATCGCCCTTCCCAACAGTTGCGCAGCCTGAATGGCGAATGG
                                                                                    4485
CATTATCGCTTCTCCGGGCGTGGCTAGCGGGAAGGGTTGTCAACGCGTCGGACTTACCGCTTACC
```

```
AATTCCAGACGATTGAGCGTCAAAATGTAGGTATTTCCATGAGCGTTTTTCCTGTTGCAATGGCT
                                                                                    4550
TTAAGGTCTGCTAACTCGCAGTTTTACATCCATAAAGGTACTCGCAAAAAGGACAACGTTACCGA
```

FIGURE 1 Continued

```
GGCGGTAATATTGTTCTGGATATTACCAGCAAGGCCGATAGTTTGAGTTCTTCTACTCAGGCAAG
                                                                            4615
CCGCCATTATAACAAGACCTATAATGGTCGTTCCGGCTATCAAACTCAAGAAGATGAGTCCGTTC

TGATGTTATTACTAATCAAAGAAGTATTGCGACAACGGTTAATTTGCGTGATGGACAGACTCTTT
                                                                            4680
ACTACAATAATGATTAGTTTCTTCATAACGCTGTTGCCAATTAAACGCACTACCTGTCTGAGAAA

TACTCGGTGGCCTCACTGATTATAAAAACACTTCTCAGGATTCTGGCGTACCGTTCCTGTCTAAA
                                                                            4745
ATGAGCCACCGGAGTGACTAATATTTTTGTGAAGAGTCCTAAGACCGCATGGCAAGGACAGATTT

ATCCCTTTAATCGGCCTCCTGTTTAGCTCCCGCTCTGATTCTAACGAGGAAAGCACGTTATACGT
                                                                            4810
TAGGGAAATTAGCCGGAGGACAAATCGAGGGCGAGACTAAGATTGCTCCTTTCGTGCAATATGCA

GCTCGTCAAAGCAACCATAGTACGCGCCCTGTAGCGGCGCATTAAGCGCGGCGGGTGTGGTGGTT
                                                                            4875
CGAGCAGTTTCGTTGGTATCATGCGCGGGACATCGCCGCGTAATTCGCGCCGCCCACACCACCAA
                                     ├──────── f1 ori ────────>

ACGCGCAGCGTGACCGCTACACTTGCCAGCGCCCTAGCGCCCGCTCCTTTCGCTTTCTTCCCTTC
                                                                            4940
TGCGCGTCGCACTGGCGATGTGAACGGTCGCGGGATCGCGGGCGAGGAAAGCGAAAGAAGGGAAG
─────────────────────────── f1 ori ───────────────────────────>

CTTTCTCGCCACGTTCGCCGGCTTTCCCCGTCAAGCTCTAAATCGGGGGCTCCCTTTAGGGTTCC
                                                                            5005
GAAAGAGCGGTGCAAGCGGCCGAAAGGGGCAGTTCGAGATTTAGCCCCCGAGGGAAATCCCAAGG
─────────────────────────── f1 ori ───────────────────────────>

GATTTAGTGCTTTACGGCACCTCGACCCCAAAAAACTTGATTAGGGTGATGGTTCACGTAGTGGG
                                                                            5070
CTAAATCACGAAATGCCGTGGAGCTGGGGTTTTTGAACTAATCCCACTACCAAGTGCATCACCC
─────────────────────────── f1 ori ───────────────────────────>

CCATCGCCCTGATAGACGGTTTTTCGCCCTTTGACGTTGGAGTCCACGTTCTTTAATAGTGGACT
                                                                            5135
GGTAGCGGGACTATCTGCCAAAAAGCGGGAAACTGCAACCTCAGGTGCAAGAAATTATCACCTGA
─────────────────────────── f1 ori ───────────────────────────>

CTTGTTCCAAACTGGAACAACACTCAACCCTATCTCGGTCTATTCTTTTGATTTATAAGGGATTT
                                                                            5200
GAACAAGGTTTGACCTTGTTGTGAGTTGGGATAGAGCCAGATAAGAAAACTAAATATTCCCTAAA
─────────────────────────── f1 ori ───────────────────────────>

TGCCGATTTCGGCCTATTGGTTAAAAAATGAGCTGATTTAACAAAATTTAACGCGAATTTTAAC
                                                                            5265
ACGGCTAAAGCCGGATAACCAATTTTTTACTCGACTAAATTGTTTTAAATTGCGCTTAAATTG
─────────────────────────── f1 ori ───────────────────────────>

SwaI
AAAATATTAACGTTTACAATTTAAATATTTGCTTATACAATCTTCCTGTTTTTGGGGCTTTTCTG
                                                                            5330
TTTTATAATTGCAAATGTTAAATTTATAAACGAATATGTTAGAAGGACAAAAACCCCGAAAAGAC
────── f1 ori ──────>
```

FIGURE 1 Continued

```
ATTATCAACCGGGGTACATATGATTGACATGCTAGTTTTACGATTACCGTTCATCGATTCTCTTG
                                                                                    5395
TAATAGTTGGCCCCATGTATACTAACTGTACGATCAAAATGCTAATGGCAAGTAGCTAAGAGAAC

TTTGCTCCAGACTCTCAGGCAATGACCTGATAGCCTTTGTAGAGACCTCTCAAAAATAGCTACCC
                                                                                    5460
AAACGAGGTCTGAGAGTCCGTTACTGGACTATCGGAAACATCTCTGGAGAGTTTTTATCGATGGG

TCTCCGGCATGAATTTATCAGCTAGAACGGTTGAATATCATATTGATGGTGATTTGACTGTCTCC
                                                                                    5525
AGAGGCCGTACTTAAATAGTCGATCTTGCCAACTTATAGTATAACTACCACTAAACTGACAGAGG

GGCCTTTCTCACCCGTTTGAATCTTTACCTACACATTACTCAGGCATTGCATTTAAAATATATGA
                                                                                    5590
CCGGAAAGAGTGGGCAAACTTAGAAATGGATGTGTAATGAGTCCGTAACGTAAATTTTATATACT

GGGTTCTAAAAATTTTTATCCTTGCGTTGAAATAAAGGCTTCTCCCGCAAAAGTATTACAGGGTC
                                                                                    5655
CCCAAGATTTTTAAAAATAGGAACGCAACTTTATTTCCGAAGAGGGCGTTTTCATAATGTCCCAG

ATAATGTTTTTGGTACAACCGATTTAGCTTTATGCTCTGAGGCTTTATTGCTTAATTTTGCTAAT
                                                                                    5720
TATTACAAAACCATGTTGGCTAAATCGAAATACGAGACTCCGAAATAACGAATTAAAACGATTA

TCTTTGCCTTGCCTGTATGATTTATTGGATGTTGGAATTCCTGATGCGGTATTTTCTCCTTACGC
                                                                                    5785
AGAAACGGAACGGACATACTAAATAACCTACAACCTTAAGGACTACGCCATAAAAGAGGAATGCG

ATCTGTGCGGTATTTCACACCGCATATGGTGCACTCTCAGTACAATCTGCTCTGATGCCGCATAG
                                                                                    5850
TAGACACGCCATAAAGTGTGGCGTATACCACGTGAGAGTCATGTTAGACGAGACTACGGCGTATC

TTAAGCCAGCCCCGACACCCGCCAACACCCGCTGACGCGCCCTGACGGGCTTGTCTGCTCCCGGC
                                                                                    5915
AATTCGGTCGGGGCTGTGGGCGGTTGTGGGCGACTGCGCGGGACTGCCCGAACAGACGAGGGCCG

ATCCGCTTACAGACAAGCTGTGACCGTCTCCGGGAGCTGCATGTGTCAGAGGTTTTCACCGTCAT
                                                                                    5980
TAGGCGAATGTCTGTTCGACACTGGCAGAGGCCCTCGACGTACACAGTCTCCAAAAGTGGCAGTA

CACCGAAACGCGCGAGACGAAAGGGCCTCGTGATACGCCTATTTTTATAGGTTAATGTCATGATA
                                                                                    6045
GTGGCTTTGCGCGCTCTGCTTTCCCGGAGCACTATGCGGATAAAAATATCCAATTACAGTACTAT

ATAATGGTTTCTTAGACGTCAGGTGGCACTTTTCGGGGAAATGTGCGCGGAACCCCTATTTGTTT
                                                                                    6110
TATTACCAAAGAATCTGCAGTCCACCGTGAAAAGCCCCTTTACACGCGCCTTGGGGATAAACAAA
                                                                     AmpR promoter >

ATTTTTCTAAATACATTCAAATATGTATCCGCTCATGAGACAATAACCCTGATAAATGCTTCAAT
                                                                                    6175
TAAAAGATTTATGTAAGTTTATACATAGGCGAGTACTCTGTTATTGGACTATTTACGAAGTTA
                              AmpR promoter >
```

FIGURE 1 Continued

```
AATATTGAAAAAGGAAGAGTATGAGTATTCAACATTTCCGTGTCGCCCTTATTCCCTTTTTTGCG
||||||||||||||||||||||||||||||||||||||||||||||||||||||||||||||||          6240
TTATAACTTTTTCCTTCTCATACTCATAAGTTGTAAAGGCACAGCGGGAATAAGGGAAAAAACGC
                                  1       5              10              15
                                  M  S  I  Q  H  F  R  V  A  L  I  P  F  F  A
......AmpR promoter.......>[..............................signal sequence..................
                                                     AmpR GCATTTTGCCTTCCTGTTTTTGCTCACCCAGAAACGCTGGTGAAAGTAAAAGATGCTGAAGATCA
||||||||||||||||||||||||||||||||||||||||||||||||||||||||||||||||          6305
CGTAAAACGGAAGGACAAAAACGAGTGGGTCTTTGCGACCACTTTCATTTTCTACGACTTCTAGT
        20                25                 30                35
 A  F  C  L  P  V  F  A  H  P  E  T  L  V  K  V  D  A  E  D  Q
......signal sequence..........|................................................>
                              AmpR GTTGGGTGCACGAGTGGGTTACATCGAACTGGATCTCAACAGCGGTAAGATCCTTGAGAGTTTTC
||||||||||||||||||||||||||||||||||||||||||||||||||||||||||||||||          6370
CAACCCACGTGCTCACCCAATGTAGCTTGACCTAGAGTTGTCGCCATTCTAGGAACTCTCAAAAG
        40                45                50                  55
 L  G  A  R  V  G  Y  I  E  L  D  L  N  S  G  K  I  L  E  S  F
                                   AmpR GCCCCGAAGAACGTTTTCCAATGATGAGCACTTTTAAAGTTCTGCTATGTGGCGCGGTATTATCC
||||||||||||||||||||||||||||||||||||||||||||||||||||||||||||||||          6435
CGGGGCTTCTTGCAAAAGGTTACTACTCGTGAAAATTTCAAGACGATACACCGCGCCATAATAGG
       60                65                70                 75            80
 R  P  E  E  R  F  P  M  M  S  T  F  K  V  L  L  C  G  A  V  L  S
                                   AmpR CGTATTGACGCCGGGCAAGAGCAACTCGGTCGCCGCATACACTATTCTCAGAATGACTTGGTTGA
||||||||||||||||||||||||||||||||||||||||||||||||||||||||||||||||          6500
GCATAACTGCGGCCCGTTCTCGTTGAGCCAGCGGCGTATGTGATAAGAGTCTTACTGAACCAACT
        85                90                95                 100
 R  I  D  A  G  Q  E  Q  L  G  R  R  I  H  Y  S  Q  N  D  L  V  E
                                   AmpR ScaI
 |
GTACTCACCAGTCACAGAAAAGCATCTTACGGATGGCATGACAGTAAGAGAATTATGCAGTGCTG
||||||||||||||||||||||||||||||||||||||||||||||||||||||||||||||||          6565
CATGAGTGGTCAGTGTCTTTTCGTAGAATGCCTACCGTACTGTCATTCTCTTAATACGTCACGAC
          105              110                115                120
 Y  S  P  V  T  E  K  H  L  T  D  G  M  T  V  R  E  L  C  S  A
                                   AmpR CCATAACCATGAGTGATAACACTGCGGCCAACTTACTTCTGACAACGATCGGAGGACCGAAGGAG
||||||||||||||||||||||||||||||||||||||||||||||||||||||||||||||||          6630
GGTATTGGTACTCACTATTGTGACGCCGGTTGAATGAAGACTGTTGCTAGCCTCCTGGCTTCCTC
        125               130              135                140             145
 A  I  T  M  S  D  N  T  A  A  N  L  L  L  T  I  G  P  K  E
                                   AmpR CTAACCGCTTTTTTGCACAACATGGGGGATCATGTAACTCGCCTTGATCGTTGGGAACCGGAGCT
||||||||||||||||||||||||||||||||||||||||||||||||||||||||||||||||          6695
GATTGGCGAAAAAACGTGTTGTACCCCCTAGTACATTGAGCGGAACTAGCAACCCTTGGCCTCGA
            150                155               160                165
 L  T  A  F  L  H  N  M  G  D  H  V  T  R  L  D  R  W  E  P  E  L
                                   AmpR
```

FIGURE 1 Continued

```
GAATGAAGCCATACCAAACGACGAGCGTGACACCACGATGCCTGTAGCAATGGCAACAACGTTGC
++++++++++++++++++++++++++++++++++++++++++++++++++++++++++++++++    6760
CTTACTTCGGTATGGTTTGCTGCTCGCACTGTGGTGCTACGGACATCGTTACCGTTGTTGCAACG
      170         175         180         185
   N  E  A  I  P  N  D  E  R  D  T  T  M  P  V  A  M  A  T  T  L   >
                              AmpR

GCAAACTATTAACTGGCGAACTACTTACTCTAGCTTCCCGGCAACAATTAATAGACTGGATGGAG
++++++++++++++++++++++++++++++++++++++++++++++++++++++++++++++++    6825
CGTTTGATAATTGACCGCTTGATGAATGAGATCGAAGGGCCGTTGTTAATTATCTGACCTACCTC
      190         195         200         205         210
   R  K  L  L  T  G  E  L  L  T  L  A  S  R  Q  Q  L  I  D  W  M  E >
                              AmpR

GCGGATAAAGTTGCAGGACCACTTCTGCGCTCGGCCCTTCCGGCTGGCTGGTTTATTGCTGATAA
++++++++++++++++++++++++++++++++++++++++++++++++++++++++++++++++    6890
CGCCTATTTCAACGTCCTGGTGAAGACGCGAGCCGGGAAGGCCGACCGACCAAATAACGACTATT
      215         220         225         230
   A  D  K  V  A  G  P  L  L  R  S  A  L  P  A  G  W  F  I  A  D  K >
                              AmpR

ATCTGGAGCCGGTGAGCGTGGGTCTCGCGGTATCATTGCAGCACTGGGGCCAGATGGTAAGCCCT
++++++++++++++++++++++++++++++++++++++++++++++++++++++++++++++++    6955
TAGACCTCGGCCACTCGCACCCAGAGCGCCATAGTAACGTCGTGACCCCGGTCTACCATTCGGGA
      235         240         245         250
   S  G  A  G  E  R  G  S  R  G  I  I  A  A  L  G  P  D  G  K  P   >
                              AmpR

CCCGTATCGTAGTTATCTACACGACGGGGAGTCAGGCAACTATGGATGAACGAAATAGACAGATC
++++++++++++++++++++++++++++++++++++++++++++++++++++++++++++++++    7020
GGGCATAGCATCAATAGATGTGCTGCCCCTCAGTCCGTTGATACCTACTTGCTTTATCTGTCTAG
      255         260         265         270         275
   S  R  I  V  V  I  Y  T  T  G  S  Q  A  T  M  D  E  R  N  R  Q  I >
                              AmpR

GCTGAGATAGGTGCCTCACTGATTAAGCATTGGTAACTGTCAGACCAAGTTTACTCATATATACT
++++++++++++++++++++++++++++++++++++++++++++++++++++++++++++++++    7085
CGACTCTATCCACGGAGTGACTAATTCGTAACCATTGACAGTCTGGTTCAAATGAGTATATATGA
      280         285
   A  E  I  G  A  S  L  I  K  H  W   *
                              AmpR

TTAGATTGATTTAAAACTTCATTTTTAATTTAAAAGGATCTAGGTGAAGATCCTTTTTGATAATC
++++++++++++++++++++++++++++++++++++++++++++++++++++++++++++++++    7150
AATCTAACTAAATTTTGAAGTAAAAATTAAATTTTCCTAGATCCACTTCTAGGAAAAACTATTAG

TCATGACCAAAATCCCTTAACGTGAGTTTTCGTTCCACTGAGCGTCAGACCCCGTAGAAAGATC
++++++++++++++++++++++++++++++++++++++++++++++++++++++++++++++++    7215
AGTACTGGTTTTAGGGAATTGCACTCAAAAGCAAGGTGACTCGCAGTCTGGGGCATCTTTCTAG

AAAGGATCTTCTTGAGATCCTTTTTTTCTGCGCGTAATCTGCTGCTTGCAAACAAAAAAACCACC
++++++++++++++++++++++++++++++++++++++++++++++++++++++++++++++++    7280
TTTCCTAGAAGAACTCTAGGAAAAAAAGACGCGCATTAGACGACGAACGTTTGTTTTTTTGGTGG
                              ori                                 >
```

FIGURE 1 Continued

```
GCTACCAGCGGTGGTTTGTTTGCCGGATCAAGAGCTACCAACTCTTTTTCCGAAGGTAACTGGCT
                                                                                    7345
CGATGGTCGCCACCAAACAAACGGCCTAGTTCTCGATGGTTGAGAAAAAGGCTTCCATTGACCGA
                                ori >

TCAGCAGAGCGCAGATACCAAATACTGTCCTTCTAGTGTAGCCGTAGTTAGGCCACCACTTCAAG
                                                                                    7410
AGTCGTCTCGCGTCTATGGTTTATGACAGGAAGATCACATCGGCATCAATCCGGTGGTGAAGTTC
                                ori >

AACTCTGTAGCACCGCCTACATACCTCGCTCTGCTAATCCTGTTACCAGTGGCTGCTGCCAGTGG
                                                                                    7475
TTGAGACATCGTGGCGGATGTATGGAGCGAGACGATTAGGACAATGGTCACCGACGACGGTCACC
                                ori >

CGATAAGTCGTGTCTTACCGGGTTGGACTCAAGACGATAGTTACCGGATAAGGCGCAGCGGTCGG
                                                                                    7540
GCTATTCAGCACAGAATGGCCCAACCTGAGTTCTGCTATCAATGGCCTATTCCGCGTCGCCAGCC
                                ori >

GCTGAACGGGGGGTTCGTGCACACAGCCCAGCTTGGAGCGAACGACCTACACCGAACTGAGATAC
                                                                                    7605
CGACTTGCCCCCCAAGCACGTGTGTCGGGTCGAACCTCGCTTGCTGGATGTGGCTTGACTCTATG
                                ori >

CTACAGCGTGAGCTATGAGAAAGCGCCACGCTTCCCGAAGGGAGAAAGGCGGACAGGTATCCGGT
                                                                                    7670
GATGTCGCACTCGATACTCTTTCGCGGTGCGAAGGGCTTCCCTCTTTCCGCCTGTCCATAGGCCA
                                ori >

AAGCGGCAGGGTCGGAACAGGAGAGCGCACGAGGGAGCTTCCAGGGGGAAACGCCTGGTATCTTT
                                                                                    7735
TTCGCCGTCCCAGCCTTGTCCTCTCGCGTGCTCCCTCGAAGGTCCCCCTTTGCGGACCATAGAAA
                                ori >

ATAGTCCTGTCGGGTTTCGCCACCTCTGACTTGAGCGTCGATTTTTGTGATGCTCGTCAGGGGGG
                                                                                    7800
TATCAGGACAGCCCAAAGCGGTGGAGACTGAACTCGCAGCTAAAACACTACGAGCAGTCCCCCC
                                ori >

CGGAGCCTATGGAAAAACGCCAGCAACGCGGCCTTTTTACGGTTCCTGGCCTTTTGCTGGCCTTT
                                                                                    7865
GCCTCGGATACCTTTTTGCGGTCGTTGCGCCGGAAAAATGCCAAGGACCGGAAAACGACCGGAAA
    ori >

PciI
TGCTCACATGTTCTTTCCTGCGTTATCCCCTGATTCTGTGGATAACCGTATTACCGCCTTTGAGT
                                                                                    7930
ACGAGTGTACAAGAAAGGACGCAATAGGGGACTAAGACACCTATTGGCATAATGGCGGAAACTCA

SapI
                                                                   BspQI
GAGCTGATACCGCTCGCCGCAGCCGAACGACCGAGCGCAGCGAGTCAGTGAGCGAGGAAGCGGAA
                                                                                    7995
CTCGACTATGGCGAGCGGCGTCGGCTTGCTGGCTCGCGTCGCTCAGTCACTCGCTCCTTCGCCTT
```

FIGURE 1 Concluded

```
GAGCGCCCAATACGCAAACCGCCTCTCCCCGCGCGTTGGCCGATTCATTAATG    3'
                                                          ***  8048
CTCGCGGGTTATGCGTTTGGCGGAGAGGGGCGCGCAACCGGCTAAGTAATTAC    5'
```

SEQ ID NO:12

FIGURE 2    Sequence: pACASI-GFP-F2A-5HRT4-HA-optimized.dna

```
5' CAGCAGCTGCGCGCTCGCTCGCTCACTGAGGCCGCCCGGGCAAAGCCCGGGCGTCGGGCGACCTT
3' GTCGTCGACGCGCGAGCGAGCGAGTGACTCCGGCGGGCCCGTTTCGGGCCCGCAGCCCGCTGGAA    65
                                      RRE

TGGTCGCCCGGCCTCAGTGAGCGAGCGAGCGCGCAGAGAGGGAGTGGCCAACTCCATCACTAGGG
   ACCAGCGGGCCGGAGTCACTCGCTCGCTCGCGCGTCTCTCCCTCACCGGTTGAGGTAGTGATCCC    130
                                      RRE

GTTCCTTGTAGTTAATGATTAACCCGCCATGCTACTTATCTACGTAGCCATGCTCTAGGACATTG
   CAAGGAACATCAATTACTAATTGGGCGGTACGATGAATAGATGCATCGGTACGAGATCCTGTAAC    195
                                                                       CMV enhancer SpeI
   ATTATTGACTAGTggagttccgcgttacataacttacggtaaatggcccgcctggctgaccgccc
   TAATAACTGATCAcctcaaggcgcaatgtattgaatgccatttaccgggcggaccgactggcggg    260
   CMV enhancer          CASI promoter
                         CMV enhancer aacgaccccgcccattgacgtcaataatgacgtatgttcccatagtaacgccaatagggactt
   ttgctggggcgggtaactgcagttattactgcatacaagggtatcattgcggttatccctgaaa    325
                         CASI promoter
                         CMV enhancer ccattgacgtcaatgggtggagtatttacggtaaactgcccacttggcagtacatcaagtgtatc
   ggtaactgcagttacccacctcataaatgccatttgacgggtgaaccgtcatgtagttcacatag    390
                         CASI promoter
                         CMV enhancer atatgccaagtacgcccctattgacgtcaatgacggtaaatggcccgcctggcattatgccag
   tatacggttcatgcggggataactgcagttactgccatttaccgggcggaccgtaatacgggtc    455
                         CASI promoter
                         CMV enhancer tacatgaccttatgggactttcctacttggcagtacatctacgtattagtcatcgctattaccat
   atgtactggaataccctgaaaggatgaaccgtcatgtagatgcataatcagtagcgataatggta    520
                         CASI promoter
                         CMV enhancer
```

FIGURE 2 Continued

```
ggtcgaggtgagccccacgttctgcttcactctccccatctccccccctcccaccccaattt
ccagctccactcggggtgcaagacgaagtgagaggggtagagggggggaggggtgggggttaaa    585
```
CASI promoter
chicken β-actin promoter
CMV enhancer

```
tgtatttatttattttaattattttgtgcagcgatggggggcggggggggggggggggcgcgcgc
acataaataaataaaaattaataaaacacgtcgctaccccgcccccccccccccgcgcgcg      650
```
CASI promoter
chicken β-actin promoter

```
caggcggggcggggcggggcgaggggcggggcggggcgaggcggagaggtgcggcggcagccaat
gtccgccccgccccgccccgctccccgccccgccccgctccgcctctccacgccgccgtcggtta   715
```
CASI promoter
chicken β-actin promoter

```
cagagcggcgcgctccgaaagtttccttttatggcgaggcggcggcggcggcggccctataaaaa
gtctcgccgcgcgaggctttcaaaggaaaataccgctccgccgccgccgccgggatatttttt    780
```
CASI promoter
chicken β-actin promoter

```
gcgaagcgcgcggcgggcgggagtcgctgcgcgctgccttcgcccgtgccccgctccgccgccg
cgcttcgcgcgccgcccgccctcagcgacgcgcgacggaagcggggcacggggcgaggcggcggc   845
```
CASI promoter
chicken β-actin promoter

```
cctcgcgccgcccgccccggctctgactgaccgcgttactaaaacaggtaagtccggcctccgcg
ggagcgcggcgggcggggccgagactgactggcgcaatgattttgtccattcaggccggaggcgc    910
```
CASI promoter AfeI
```
ccgggttttggcgcctccgcgggcgcccccctcctcacggcgagcgctgccacgtcagacgaag
ggcccaaaaccgcggagggcgcccgcgggggggaggagtgccgctcgcgacggtgcagtctgcttc   975
```
CASI promoter

```
ggcgcagcgagcgtcctgatccttccgcccggacgctcaggacagcggcccgctgctcataagac
ccgcgtcgctcgcaggactaggaaggcgggcctgcgagtcctgtcgccgggcgacgagtattctg   1040
```
CASI promoter

```
tcggccttagaaccccagtatcagcagaaggacatttaggacgggacttgggtgactctagggc
agccggaatcttggggtcatagtcgtcttcctgtaaaatcctgccctgaacccactgagatcccg   1105
```
CASI promoter

FIGURE 2 Continued

```
actggttttctttccagagagcggaacaggcgaggaaaagtagtcccttctcggcgattctgcgg         1170
tgaccaaaagaaaggtctctcgccttgtccgctccttttcatcagggaagagccgctaagacgc
                                    CAS1 promoter agggatctccgtgggcggtgaacgccgatgatgcctctactaaccatgttcatgttttctttt          1235
tccctagaggcaccccgccacttgcggctactacggagatgattggtacaagtacaaaagaaaa
                                    CAS1 promoter Acc65I    KpnI
ttttctacaggtcctgggtgacgaacagGGTACCGCCACCATGGTGTCCAAGGGAGAGGAGCTGT        1300
aaaagatgtccaggacccactgcttgtcCCATGGCGGTGGTACCACAGGTTCCCTCTCCTCGACA
                                                    M  V  S  K  G  E  E  L
                          CAS1 promoter    KpnI   kozak   eGFP mouse-human codon optimized TCACCGGAGTGGTGCCCATCCTGGTGGAGCTGGACGGCGATGTGAATGGCCACAAGTTTAGCGTG        1365
AGTGGCCTCACCACGGGTAGGACCACCTCGACCTGCCGCTACACTTACCGGTGTTCAAATCGCAC
  10            15           20            25           30
  F  T  G  V  V  P  I  L  V  E  L  D  G  D  V  N  G  H  K  F  S  V
                          eGFP mouse-human codon optimized BspEI
TCCGGAGAGGGAGAGGGCGACGCAACCTACGGCAAGCTGACACTGAAGTTCATCTGCACCACAGG      1430
AGGCCTCTCCCTCTCCCGCTGCGTTGGATGCCGTTCGACTGTGACTTCAAGTAGACGTGGTGTCC
        35            40           45            50
  S  G  E  G  E  G  D  A  T  Y  G  K  L  T  L  K  F  I  C  T  T  G
                          eGFP mouse-human codon optimized BstEII
CAAGCTGCCCGTGCCTTGGCCAACCCTGGTGACCACACTGACATACGGCGTGCAGTGTTTTTCTC      1495
GTTCGACGGGCACGGAACCGGTTGGGACCACTGGTGTGACTGTATGCCGCACGTCACAAAAAGAG
      55            60           65            70
  K  L  P  V  P  W  P  T  L  V  T  T  L  T  Y  G  V  Q  C  F  S
                          eGFP mouse-human codon optimized GGTATCCAGACCACATGAAGCAGCACGATTTCTTTAAGAGCGCCATGCCCGAGGGCTACGTGCAG      1560
CCATAGGTCTGGTGTACTTCGTCGTGCTAAAGAAATTCTCGCGGTACGGGCTCCCGATGCACGTC
    75            80           85           90           95
  R  Y  P  D  H  M  K  Q  H  D  F  F  K  S  A  M  P  E  G  Y  V  Q
                          eGFP mouse-human codon optimized GAGAGGACAATCTTCTTTAAGGACGATGGCAACTATAAGACCAGAGCCGAGGTGAAGTTCGAGGG      1625
CTCTCCTGTTAGAAGAAATTCCTGCTACCGTTGATATTCTGGTCTCGGCTCCACTTCAAGCTCCC
          100            105            110            115
  E  R  T  I  F  F  K  D  D  G  N  Y  K  T  R  A  E  V  K  F  E  G
                          eGFP mouse-human codon optimized CGACACACTGGTGAACCGGATCGAGCTGAAGGGCATCGACTTTAAGGAGGATGGCAATATCCTGG      1690
GCTGTGTGACCACTTGGCCTAGCTCGACTTCCCGTAGCTGAAATTCCTCCTACCGTTATAGGACC
        120           125           130           135
  D  T  L  V  N  R  I  E  L  K  G  I  D  F  K  E  D  G  N  I  L
                          eGFP mouse-human codon optimized
```

```
GGTCATGGTGGCCGTGTGCTGGGACAGGCAGCTGCGCAAGATCAAGACAAACTACTTCATCGTGT
CCAGTACCACCGGCACACGACCCTGTCCGTCGACGCGTTCTAGTTCTGTTTGATGAAGTAGCACA   2275
     40        45        50        55        60
    V  M  V  A  V  C  W  D  R  Q  L  R  K  I  K  T  N  Y  F  I  V
                    5-HTR4 mouse-human codon optimized CTCTGGCCTTTGCCGATCTGCTGGTGAGCGTGCTGGTCATGCCTTTCGGCGCCATCGAGCTGGTG
GAGACCGGAAACGGCTAGACGACCACTCGCACGACCAGTACGGAAAGCCGCGGTAGCTCGACCAC   2340
         65        70        75        80
     S  L  A  F  A  D  L  L  V  S  V  L  V  M  P  F  G  A  I  E  L  V
                    5-HTR4 mouse-human codon optimized CAGGACATCTGGATCTATGGCGAGGTGTTTGCCTGGTGCGGACCAGCCTGGATGTGCTGCTGAC
GTCCTGTAGACCTAGATACCGCTCCACAAACGGACCACGCCTGGTCGGACCTACACGACGACTG   2405
     85        90        95        100
    Q  D  I  W  I  Y  G  E  V  F  C  L  V  R  T  S  L  D  V  L  L  T
                    5-HTR4 mouse-human codon optimized CACAGCCAGCATCTTCCACCTGTGCTGTATCTCCCTGGACCGCTACTATGCCATCTGCTGTCAGC
GTGTCGGTCGTAGAAGGTGGACACGACATAGAGGGACCTGGCGATGATACGGTAGACGACAGTCG   2470
    105       110       115       120       125
    T  A  S  I  F  H  L  C  C  I  S  L  D  R  Y  Y  A  I  C  C  Q
                    5-HTR4 mouse-human codon optimized CTCTGGTGTACCGGAATAAGATGACACCACTGAGGATCGCCCTGATGCTGGGAGGATGTTGGGTC
GAGACCACATGGCCTTATTCTACTGTGGTGACTCCTAGCGGGACTACGACCCTCCTACAACCCAG   2535
        130       135       140       145
    P  L  V  Y  R  N  K  M  T  P  L  R  I  A  L  M  L  G  G  C  W  V
                    5-HTR4 mouse-human codon optimized ATCCCTACCTTCATCTCTTTTCTGCCAATCATGCAGGGCTGGAACAATATCGGCATCATCGATCT
TAGGGATGGAAGTAGAGAAAAGACGGTTAGTACGTCCCGACCTTGTTATAGCCGTAGTAGCTAGA   2600
        150       155       160       165
    I  P  T  F  I  S  F  L  P  I  M  Q  G  W  N  N  I  G  I  I  D  L
                    5-HTR4 mouse-human codon optimized GATCGAGAAGAGGAAGTTCAACCAGAATTCCAACTCTACATACTGCGTGTTCATGGTGAACAAGC
CTAGCTCTTCTCCTTCAAGTTGGTCTTAAGGTTGAGATGTATGACGCACAAGTACCACTTGTTCG   2665
    170       175       180       185       190
    I  E  K  R  K  F  N  Q  N  S  N  S  T  Y  C  V  F  M  V  N  K
                    5-HTR4 mouse-human codon optimized CCTATGCCATCACCTGCAGCGTGGTGGCCTTCTACATCCCTTTTCTGCTGATGGTGCTGGCCTAC
GGATACGGTAGTGGACGTCGCACCACCGGAAGATGTAGGGAAAAGACGACTACCACGACCGGATG   2730
         195       200       205       210
    P  Y  A  I  T  C  S  V  V  A  F  Y  I  P  F  L  L  M  V  L  A  Y
                    5-HTR4 mouse-human codon optimized TATCGGATCTATGTGACAGCCAAGGAGCACGCCCACCAGATCCAGATGCTGCAGAGGGCAGGAGC
ATAGCCTAGATACACTGTCGGTTCCTCGTGCGGGTGGTCTAGGTCTACGACGTCTCCCGTCCTCG   2795
     215       220       225       230
    Y  R  I  Y  V  T  A  K  E  H  A  H  Q  I  Q  M  L  Q  R  A  G  A
                    5-HTR4 mouse-human codon optimized
```

FIGURE 2 Continued

```
         CTCTAGCGAGAGCAGGCCACAGAGCGCCGACCAGCACTCCACACACAGGATGAGAACAGAGACCA
         GAGATCGCTCTCGTCCGGTGTCTCGCGGCTGGTCGTGAGGTGTGTGTCCTACTCTTGTCTCTGGT      2860
              235         240         245         250         255
              S  S  E  S  R  P  Q  S  A  D  Q  H  S  T  H  R  M  R  T  E  T
              5-HTR4 mouse-human codon optimized                            >

PspOMI    ApaI
         AGGCCGCCAAGACCCTGTGCATCATCATGGGCTGCTTCTGTCTGTGCTGGGCCCCCTTCTTTGTG
         TCCGGCGGTTCTGGGACACGTAGTAGTACCCGACGAAGACAGACACGACCCGGGGGAAGAAACAC     2925
              260         265         270         275
              K  A  A  K  T  L  C  I  I  M  G  C  F  C  L  C  W  A  P  F  F  V
              5-HTR4 mouse-human codon optimized                            >

ACCAATATCGTGGACCCCTTCATCGATTACACAGTGCCTGGCCAAGTGTGGACCGCCTTTCTGTG
         TGGTTATAGCACCTGGGGAAGTAGCTAATGTGTCACGGACCGGTTCACACCTGGCGGAAAGACAC     2990
              280         285         290         295
              T  N  I  V  D  P  F  I  D  Y  T  V  P  G  Q  V  W  T  A  F  L  W
              5-HTR4 mouse-human codon optimized                            >

GCTGGGCTACATCAATAGCGGCCTGAACCCCTTCCTGTATGCCTTTCTGAACAAGTCCTTCAGGA
         CGACCCGATGTAGTTATCGCCGGACTTGGGGAAGGACATACGGAAAGACTTGTTCAGGAAGTCCT     3055
              300         305         310         315         320
              L  G  Y  I  N  S  G  L  N  P  F  L  Y  A  F  L  N  K  S  F  R
              5-HTR4 mouse-human codon optimized                            >

GAGCCTTTCTGATCATCCTGTGCTGTGACGATGAGAGGTACAGGAGGCCCTCTATCCTGGGCCAG
         CTCGGAAAGACTAGTAGGACACGACACTGCTACTCTCCATGTCCTCCGGGAGATAGGACCCGGTC     3120
              325         330         335         340
              R  A  F  L  I  I  L  C  C  D  D  E  R  Y  R  R  P  S  I  L  G  Q
              5-HTR4 mouse-human codon optimized                            >

PmlI     BbvCI       BstZ17I
         ACCGTGCCCTGTTCCACCACAACCATCAATGGCTCTACACACGTGCTGAGGTATACCGTGCTGCA
         TGGCACGGGACAAGGTGGTGTTGGTAGTTACCGAGATGTGTGCACGACTCCATATGGCACGACGT     3185
              345         350         355         360
              T  V  P  C  S  T  T  T  I  N  G  S  T  H  V  L  R  Y  T  V  L  H
              5-HTR4 mouse-human codon optimized                            >

CAGAGGCCACCACCAGGAGCTGGAGAAGCTGCCAATCCACAACGATCCCGAGAGCCTGGAGTCCT
         GTCTCCGGTGGTGGTCCTCGACCTCTTCGACGGTTAGGTGTTGCTAGGGCTCTCGGACCTCAGGA     3250
              365         370         375         380         385
              R  G  H  H  Q  E  L  E  K  L  P  I  H  N  D  P  E  S  L  E  S
              5-HTR4 mouse-human codon optimized                            >

Xbal
         GCTTTTACCCCTATGACGTGCCTGATTATGCCTGACTCTAGAAtaatcaacctctggattacaaa
         CGAAAATGGGGATACTGCACGGACTAATACGGACTGAGATCTTattagttggagacctaatgttt     3315
              1                5
              C  F  Y  P  Y  D  V  P  D  Y  A  *
              5-H>           HA                 >   XbaI        WPRE
```

FIGURE 2 Continued

```
atttgtgaaagattgactggtattcttaactatgttgctccttttacgctatgtggatacgctgc
taaacactttctaactgaccataagaattgatacaacgaggaaaatgcgatacacctatgcgacg
                                    WPRE                                          3380 tttaatgcctttgtatcatgctattgcttcccgtatggctttcattttctcctccttgtataaat
aaattacggaaacatagtacgataacgaagggcataccgaaagtaaaagaggaggaacatattta
                                    WPRE                                          3445 cctggttgctgtctcttatgaggagttgtggcccgttgtcaggcaacgtggcgtggtgtgcact
ggaccaacgacagagaaatactcctcaacaccgggcaacagtccgttgcaccgcaccacacgtga
                                    WPRE                                          3510 gtgtttgctgacgcaaccccactggttggggcattgccaccacctgtcagctcctttccgggac
cacaaacgactgcgttgggggtgaccaaccccgtaacggtggtggacagtcgaggaaaggccctg
                                    WPRE                                          3575 tttcgcttccccctccctattgccacggcggaactcatcgccgcctgccttgcccgctgctgga
aaagcgaaaggggagggataacggtgccgccttgagtagcggcggacggaacgggcgacgacct
                                    WPRE                                          3640 caggggctcggctgttgggcactgacaattccgtggtgttgtcggggaaatcatcgtcctttcct
gtccccgagccgacaacccgtgactgttaaggcaccacaacagcccctttagtagcaggaaagga
                                                                 ※ R   G   K   R
                                    WPRE                                          3705 tggctgctcgcctgtgttgccacctggattctgcgcgggacgtccttctgctacgtcccttcggc
accgacgagcggacacaacggtggacctaagacgcgccctgcaggaagacgatgcaggaagccg
  P    Q    E    G    T    N    G    G    P    N    Q    A    P    R    G    E    A    V    D    R    R    G
              (in frame with Factor Xa site)                                 Factor Xa site
                                    WPRE                                          3770

BbsI
cctcaatccagcggaccttccttcccgcggcctgctgccggctctgcggcctcttccgcgtcttc
ggagttaggtcgcctggaaggaagggcgccggacgacggccgagacgccggagaaggcgcagaag
  E   I
Factor Xa site
                                    WPRE HindIII
gccttcgccctcagacgagtcggatctcccttttgggccgcctccccgcctAAGCTTATCGATACC
cggaagcgggagtctgctcagcctagagggaaaccccggcggaggggcggaTTCGAATAGCTATGG
                                    WPRE                                          3900
```

FIGURE 2 Continued

```
        BglII
GTCGAGATCTAACTTGTTTATTGCAGCTTATAATGGTTACAAATAAAGCAATAGCATCACAAATT
|||||||||||||||||||||||||||||||||||||||||||||||||||||||||||||||||    3965
CAGCTCTAGATTGAACAAATAACGTCGAATATTACCAATGTTTATTTCGTTATCGTAGTGTTTAA
                          SV40 poly(A) signal BsmI
TCACAAATAAAGCATTTTTTTCACTGCATTCTAGTTGTGGTTTGTCCAAACTCATCAATGTATCT
|||||||||||||||||||||||||||||||||||||||||||||||||||||||||||||||||    4030
AGTGTTTATTTCGTAAAAAAAGTGACGTAAGATCAACACCAAACAGGTTTGAGTAGTTACATAGA
                          SV40 poly(A) signal TATCATGTCTGGATCTCGACCTCGACTAGAGCATGGCTACGTAGATAAGTAGCATGGCGGGTTAA
|||||||||||||||||||||||||||||||||||||||||||||||||||||||||||||||||    4095
ATAGTACAGACCTAGAGCTGGAGCTGATCTCGTACCGATGCATCTATTCATCGTACCGCCCAATT
     SV40 poly(A) signal TCATTAACTACAAGGAACCCCTAGTGATGGAGTTGGCCACTCCCTCTCTGCGCGCTCGCTCGCTC
|||||||||||||||||||||||||||||||||||||||||||||||||||||||||||||||||    4160
AGTAATTGATGTTCCTTGGGGATCACTACCTCAACCGGTGAGGGAGAGACGCGCGAGCGAGCGAG
                                                           RBE ACTGAGGCCGGGCGACCAAAGGTCGCCCGACGCCCGGGCTTTGCCCGGGCGGCCTCAGTGAGCGA
|||||||||||||||||||||||||||||||||||||||||||||||||||||||||||||||||    4225
TGACTCCGGCCCGCTGGTTTCCAGCGGGCTGCGGGCCCGAAACGGGCCCGCCGGAGTCACTCGCT
                                                           RBE GCGAGCGCGCCAGCTGGCGTAATAGCGAAGAGGCCCGCACCGATCGCCCTTCCCAACAGTTGCGC
|||||||||||||||||||||||||||||||||||||||||||||||||||||||||||||||||    4290
CGCTCGCGCGGTCGACCGCATTATCGCTTCTCCGGGCGTGGCTAGCGGGAAGGGTTGTCAACGCG

RBE

AGCCTGAATGGCGAATGGAATTCCAGACGATTGAGCGTCAAAATGTAGGTATTTCCATGAGCGTT
|||||||||||||||||||||||||||||||||||||||||||||||||||||||||||||||||    4355
TCGGACTTACCGCTTACCTTAAGGTCTGCTAACTCGCAGTTTTACATCCATAAAGGTACTCGCAA

TTTCCTGTTGCAATGGCTGGCGGTAATATTGTTCTGGATATTACCAGCAAGGCCGATAGTTTGAG
|||||||||||||||||||||||||||||||||||||||||||||||||||||||||||||||||    4420
AAAGGACAACGTTACCGACCGCCATTATAACAAGACCTATAATGGTCGTTCCGGCTATCAAACTC

TTCTTCTACTCAGGCAAGTGATGTTATTACTAATCAAAGAAGTATTGCGACAACGGTTAATTTGC
|||||||||||||||||||||||||||||||||||||||||||||||||||||||||||||||||    4485
AAGAAGATGAGTCCGTTCACTACAATAATGATTAGTTTCTTCATAACGCTGTTGCCAATTAAACG

GTGATGGACAGACTCTTTTACTCGGTGGCCTCACTGATTATAAAAACACTTCTCAGGATTCTGGC
|||||||||||||||||||||||||||||||||||||||||||||||||||||||||||||||||    4550
CACTACCTGTCTGAGAAAATGAGCCACCGGAGTGACTAATATTTTTGTGAAGAGTCCTAAGACCG

GTACCGTTCCTGTCTAAAATCCCTTTAATCGGCCTCCTGTTTAGCTCCCGCTCTGATTCTAACGA
|||||||||||||||||||||||||||||||||||||||||||||||||||||||||||||||||    4615
CATGGCAAGGACAGATTTTAGGGAAATTAGCCGGAGGACAAATCGAGGGCGAGACTAAGATTGCT
```

FIGURE 2 Continued

```
GGAAAGCACGTTATACGTGCTCGTCAAAGCAACCATAGTACGCGCCCTGTAGCGGCGCATTAAGC
CCTTTCGTGCAATATGCACGAGCAGTTTCGTTGGTATCATGCGCGGGACATCGCCGCGTAATTCG     4680
                                                    fl_ori >

GCGGCGGGTGTGGTGGTTACGCGCAGCGTGACCGCTACACTTGCCAGCGCCCTAGCGCCCGCTCC
CGCCGCCCACACCACCAATGCGCGTCGCACTGGCGATGTGAACGGTCGCGGGATCGCGGGCGAGG     4745
                                fl_ori >

TTTCGCTTTCTTCCCTTCCTTTCTCGCCACGTTCGCCGGCTTTCCCCGTCAAGCTCTAAATCGGG
AAAGCGAAAGAAGGGAAGGAAAGAGCGGTGCAAGCGGCCGAAAGGGGCAGTTCGAGATTTAGCCC     4810
                                fl_ori >

GGCTCCCTTTAGGGTTCCGATTTAGTGCTTTACGGCACCTCGACCCCAAAAAACTTGATTAGGGT
CCGAGGGAAATCCCAAGGCTAAATCACGAAATGCCGTGGAGCTGGGGTTTTTTGAACTAATCCCA     4875
                                fl_ori >

GATGGTTCACGTAGTGGGCCATCGCCCTGATAGACGGTTTTTCGCCCTTTGACGTTGGAGTCCAC
CTACCAAGTGCATCACCCGGTAGCGGGACTATCTGCCAAAAAGCGGGAAACTGCAACCTCAGGTG     4940
                                fl_ori >

GTTCTTTAATAGTGGACTCTTGTTCCAAACTGGAACAACACTCAACCCTATCTCGGTCTATTCTT
CAAGAAATTATCACCTGAGAACAAGGTTTGACCTTGTTGTGAGTTGGGATAGAGCCAGATAAGAA     5005
                                fl_ori >

TTGATTTATAAGGGATTTTGCCGATTTCGGCCTATTGGTTAAAAAATGAGCTGATTTAACAAAAA
AACTAAATATTCCCTAAAACGGCTAAAGCCGGATAACCAATTTTTTACTCGACTAAATTGTTTTT     5070
                                fl_ori >

Swal
TTTAACGCGAATTTTAACAAAATATTAACGTTTACAATTTAAATATTTGCTTATACAATCTTCCT
AAATTGCGCTTAAAATTGTTTTATAATTGCAAATGTTAAATTTATAAACGAATATGTTAGAAGGA     5135
       fl_ori >

GTTTTTGGGGCTTTTCTGATTATCAACCGGGGTACATATGATTGACATGCTAGTTTTACGATTAC
CAAAAACCCCGAAAAGACTAATAGTTGGCCCCATGTATACTAACTGTACGATCAAAATGCTAATG     5200

CGTTCATCGATTCTCTTGTTTGCTCCAGACTCTCAGGCAATGACCTGATAGCCTTTGTAGAGACC
GCAAGTAGCTAAGAGAACAAACGAGGTCTGAGAGTCCGTTACTGGACTATCGGAAACATCTCTGG     5265

TCTCAAAAATAGCTACCCTCTCCGGCATGAATTTATCAGCTAGAACGGTTGAATATCATATTGAT
AGAGTTTTATCGATGGGAGAGGCCGTACTTAAATAGTCGATCTTGCCAACTTATAGTATAACTA     5330

GGTGATTTGACTGTCTCCGGCCTTTCTCACCCGTTTGAATCTTTACCTACACATTACTCAGGCAT
CCACTAAACTGACAGAGGCCGGAAAGAGTGGGCAAACTTAGAAATGGATGTGTAATGAGTCCGTA     5395
```

FIGURE 2 Continued

```
TGCATTTAAAATATATGAGGGTTCTAAAAATTTTTATCCTTGCGTTGAAATAAAGGCTTCTCCG
                                                                          5460
ACGTAAATTTTATATACTCCCAAGATTTTTAAAAATAGGAACGCAACTTTATTTCCGAAGAGGGC

CAAAAGTATTACAGGGTCATAATGTTTTTGGTACAACCGATTTAGCTTTATGCTCTGAGGCTTTA
                                                                          5525
GTTTTCATAATGTCCCAGTATTACAAAAACCATGTTGGCTAAATCGAAATACGAGACTCCGAAAT

TTGCTTAATTTTGCTAATTCTTTGCCTTGCCTGTATGATTTATTGGATGTTGGAATTCCTGATGC
                                                                          5590
AACGAATTAAAACGATTAAGAAACGGAACGGACATACTAAATAACCTACAACCTTAAGGACTACG

GGTATTTTCTCCTTACGCATCTGTGCGGTATTTCACACCGCATATGGTGCACTCTCAGTACAATC
                                                                          5655
CCATAAAAGAGGAATGCGTAGACACGCCATAAAGTGTGGCGTATACCACGTGAGAGTCATGTTAG

TGCTCTGATGCCGCATAGTTAAGCCAGCCCCGACACCCGCCAACACCCGCTGACGCGCCCTGACG
                                                                          5720
ACGAGACTACGGCGTATCAATTCGGTCGGGGCTGTGGGCGGTTGTGGGCGACTGCGCGGGACTGC

GGCTTGTCTGCTCCCGGCATCCGCTTACAGACAAGCTGTGACCGTCTCCGGGAGCTGCATGTGTC
                                                                          5785
CCGAACAGACGAGGGCCGTAGGCGAATGTCTGTTCGACACTGGCAGAGGCCCTCGACGTACACAG

AGAGGTTTTCACCGTCATCACCGAAACGCGCGAGACGAAAGGGCCTCGTGATACGCCTATTTTA
                                                                          5850
TCTCCAAAAGTGGCAGTAGTGGCTTTGCGCGCTCTGCTTTCCCGGAGCACTATGCGGATAAAAAT

TAGGTTAATGTCATGATAATAATGGTTTCTTAGACGTCAGGTGGCACTTTTCGGGGAAATGTGCG
                                                                          5915
ATCCAATTACAGTACTATTATTACCAAAGAATCTGCAGTCCACCGTGAAAAGCCCCTTTACACGC
                                                                     AmpR promoter CGGAACCCCTATTTGTTTATTTTTCTAAATACATTCAAATATGTATCCGCTCATGAGACAATAAC
                                                                          5980
GCCTTGGGGATAAACAAATAAAAAGATTTATGTAAGTTTATACATAGGCGAGTACTCTGTTATTG
                                        AmpR promoter CCTGATAAATGCTTCAATAATATTGAAAAAGGAAGAGTATGAGTATTCAACATTTCCGTGTCGCC
                                                                          6045
GGACTATTTACGAAGTTATTATAACTTTTTCCTTCTCATACTCATAAGTTGTAAAGGCACAGCGG
                                                      1        5
                                                      M S I Q H F R V A
                                 AmpR promoter         signal sequence
                                                            AmpR CTTATTCCCTTTTTTGCGGCATTTTGCCTTCCTGTTTTTGCTCACCCAGAAACGCTGGTGAAAGT
                                                                          6110
GAATAAGGGAAAAAACGCCGTAAAACGGAAGGACAAAAACGAGTGGGTCTTTGCGACCACTTTCA
   10           15            20           25            30
   L I P F F A A F C L P V F A K P E T L V K V
        signal sequence
                         AmpR AAAAGATGCTGAAGATCAGTTGGGTGCACGAGTGGGTTACATCGAACTGGATCTCAACAGCGGTA
                                                                          6175
TTTTCTACGACTTCTAGTCAACCCACGTGCTCACCCAATGTAGCTTGACCTAGAGTTGTCGCCAT
    35            40            45            50
  K D A E D Q L G A R V G Y I E L D L N S G
                         AmpR
```

FIGURE 2 Continued

```
       AGATCCTTGAGAGTTTTCGCCCCGAAGAACGTTTTCCAATGATGAGCACTTTTAAAGTTCTGCTA
                                                                                        6240
       TCTAGGAACTCTCAAAAGCGGGGCTTCTTGCAAAAGGTTACTACTCGTGAAAATTTCAAGACGAT
            55         60          65         70
        K  I  L  E  S  F  R  P  E  E  R  F  P  M  M  S  T  F  K  V  L  L
                                       AmpR
```

```
       TGTGGCGCGGTATTATCCCGTATTGACGCCGGGCAAGAGCAACTCGGTCGCCGCATACACTATTC
                                                                                        6305
       ACACCGCGCCATAATAGGGCATAACTGCGGCCCGTTCTCGTTGAGCCAGCGGCGTATGTGATAAG
            75         80          85         90         95
        C  G  A  V  L  S  R  I  D  A  G  Q  E  Q  L  G  R  R  I  H  Y  S
                                       AmpR
```

```
                        ScaI
       TCAGAATGACTTGGTTGAGTACTCACCAGTCACAGAAAAGCATCTTACGGATGGCATGACAGTAA
                                                                                        6370
       AGTCTTACTGAACCAACTCATGAGTGGTCAGTGTCTTTTCGTAGAATGCCTACCGTACTGTCATT
            100        105         110        115
        Q  N  D  L  V  E  Y  S  P  V  T  E  K  H  L  T  D  G  M  T  V
                                       AmpR
```

```
       GAGAATTATGCAGTGCTGCCATAACCATGAGTGATAACACTGCGGCCAACTTACTTCTGACAACG
                                                                                        6435
       CTCTTAATACGTCACGACGGTATTGGTACTCACTATTGTGACGCCGGTTGAATGAAGACTGTTGC
            120        125         130        135
        R  E  L  C  S  A  A  I  T  M  S  D  N  T  A  A  N  L  L  L  T  T
                                       AmpR
```

```
       ATCGGAGGACCGAAGGAGCTAACCGCTTTTTTGCACAACATGGGGGATCATGTAACTCGCCTTGA
                                                                                        6500
       TAGCCTCCTGGCTTCCTCGATTGGCGAAAAAACGTGTTGTACCCCCTAGTACATTGAGCGGAACT
            140        145         150        155        160
        I  G  G  P  K  E  L  T  A  F  L  H  N  M  G  D  H  V  T  R  L  D
                                       AmpR
```

```
       TCGTTGGGAACCGGAGCTGAATGAAGCCATACCAAACGACGAGCGTGACACCACGATGCCTGTAG
                                                                                        6565
       AGCAACCCTTGGCCTCGACTTACTTCGGTATGGTTTGCTGCTCGCACTGTGGTGCTACGGACATC
            165        170         175        180
        R  W  E  P  E  L  N  E  A  I  P  N  D  E  R  D  T  T  M  P  V
                                       AmpR
```

```
       CAATGGCAACAACGTTGCGCAAACTATTAACTGGCGAACTACTTACTCTAGCTTCCCGGCAACAA
                                                                                        6630
       GTTACCGTTGTTGCAACGCGTTTGATAATTGACCGCTTGATGAATGAGATCGAAGGGCCGTTGTT
            185        190         195        200
        A  M  A  T  T  L  R  K  L  L  T  G  E  L  L  T  L  A  S  R  Q  Q
                                       AmpR
```

```
       TTAATAGACTGGATGGAGGCGGATAAAGTTGCAGGACCACTTCTGCGCTCGGCCCTTCCGGCTGG
                                                                                        6695
       AATTATCTGACCTACCTCCGCCTATTTCAACGTCCTGGTGAAGACGCGAGCCGGGAAGGCCGACC
            205        210         215        220        225
        L  I  D  W  M  E  A  D  K  V  A  G  P  L  L  R  S  A  L  P  A  G
                                       AmpR
```

FIGURE 2 Continued

```
CTGGTTTATTGCTGATAAATCTGGAGCCGGTGAGCGTGGGTCTCGCGGTATCATTGCAGCACTGG        6760
GACCAAATAACGACTATTTAGACCTCGGCCACTCGCACCCAGAGCGCCATAGTAACGTCGTGACC
              230       235       240       245
      W  F  I  A  D  K  S  G  A  G  E  R  G  S  R  G  I  I  A  A  L
                                    AmpR

GGCCAGATGGTAAGCCCTCCCGTATCGTAGTTATCTACACGACGGGGAGTCAGGCAACTATGGAT        6825
CCGGTCTACCATTCGGGAGGGCATAGCATCAATAGATGTGCTGCCCCTCAGTCCGTTGATACCTA
          250       255       260       265
    G  P  D  G  K  P  S  R  I  V  V  I  Y  T  T  G  S  Q  A  T  M  D
                                    AmpR

GAACGAAATAGACAGATCGCTGAGATAGGTGCCTCACTGATTAAGCATTGGTAACTGTCAGACCA        6890
CTTGCTTTATCTGTCTAGCGACTCTATCCACGGAGTGACTAATTCGTAACCATTGACAGTCTGGT
      270       275       280       285
    E  R  N  R  Q  I  A  E  I  G  A  S  L  I  K  H  W  *
                                    AmpR

AGTTTACTCATATATACTTTAGATTGATTTAAAACTTCATTTTTAATTTAAAAGGATCTAGGTGA        6955
TCAAATGAGTATATATGAAATCTAACTAAATTTTGAAGTAAAAATTAAATTTTCCTAGATCCACT

AGATCCTTTTTGATAATCTCATGACCAAAATCCCTTAACGTGAGTTTTCGTTCCACTGAGCGTCA        7020
TCTAGGAAAAACTATTAGAGTACTGGTTTTAGGGAATTGCACTCAAAAGCAAGGTGACTCGCAGT

GACCCCGTAGAAAAGATCAAAGGATCTTCTTGAGATCCTTTTTTTCTGCGCGTAATCTGCTGCTT        7085
CTGGGGCATCTTTTCTAGTTTCCTAGAAGAACTCTAGGAAAAAAAGACGCGCATTAGACGACGAA
                                            ori GCAAACAAAAAACCACCGCTACCAGCGGTGGTTTGTTTGCCGGATCAAGAGCTACCAACTCTTT        7150
CGTTTGTTTTTTGGTGGCGATGGTCGCCACCAAACAAACGGCCTAGTTCTCGATGGTTGAGAAA
                                            ori TTCCGAAGGTAACTGGCTTCAGCAGAGCGCAGATACCAAATACTGTCCTTCTAGTGTAGCCGTAG        7215
AAGGCTTCCATTGACCGAAGTCGTCTCGCGTCTATGGTTTATGACAGGAAGATCACATCGGCATC
                                            ori TTAGGCCACCACTTCAAGAACTCTGTAGCACCGCCTACATACCTCGCTCTGCTAATCCTGTTACC        7280
AATCCGGTGGTGAAGTTCTTGAGACATCGTGGCGGATGTATGGAGCGAGACGATTAGGACAATGG
                                            ori AGTGGCTGCTGCCAGTGGCGATAAGTCGTGTCTTACCGGGTTGGACTCAAGACGATAGTTACCGG        7345
TCACCGACGACGGTCACCGCTATTCAGCACAGAATGGCCCAACCTGAGTTCTGCTATCAATGGCC
                                            ori
```

FIGURE 2 Concluded

```
ATAAGGCGCAGCGGTCGGGCTGAACGGGGGGTTCGTGCACACAGCCCAGCTTGGAGCGAACGACC
                                                                          7410
TATTCCGCGTCGCCAGCCCGACTTGCCCCCCAAGCACGTGTGTCGGGTCGAACCTCGCTTGCTGG
                                 ori TACACCGAACTGAGATACCTACAGCGTGAGCTATGAGAAAGCGCCACGCTTCCCGAAGGGAGAAA
                                                                          7475
ATGTGGCTTGACTCTATGGATGTCGCACTCGATACTCTTTCGCGGTGCGAAGGGCTTCCCTCTTT
                                 ori GGCGGACAGGTATCCGGTAAGCGGCAGGGTCGGAACAGGAGAGCGCACGAGGGAGCTTCCAGGGG
                                                                          7540
CCGCCTGTCCATAGGCCATTCGCCGTCCCAGCCTTGTCCTCTCGCGTGCTCCCTCGAAGGTCCCC
                                 ori GAAACGCCTGGTATCTTTATAGTCCTGTCGGGTTTCGCCACCTCTGACTTGAGCGTCGATTTTTG
                                                                          7605
CTTTGCGGACCATAGAAATATCAGGACAGCCCAAAGCGGTGGAGACTGAACTCGCAGCTAAAAAC
                                 ori TGATGCTCGTCAGGGGGCGGAGCCTATGGAAAAACGCCAGCAACGCGGCCTTTTTACGGTTCCT
                                                                          7670
ACTACGAGCAGTCCCCCCGCCTCGGATACCTTTTTGCGGTCGTTGCGCCGGAAAAATGCCAAGGA
              ori PciI
GGCCTTTTGCTGGCCTTTTGCTCACATGTTCTTTCCTGCGTTATCCCCTGATTCTGTGGATAACC
                                                                          7735
CCGGAAAACGACCGGAAAACGAGTGTACAAGAAAGGACGCAATAGGGACTAAGACACCTATTGG GTATTACCGCCTTTGAGTGAGCTGATACCGCTCGCCGCAGCCGAACGACCGAGCGCAGCGAGTCA
                                                                          7800
CATAATGGCGGAAACTCACTCGACTATGGCGAGCGGCGTCGGCTTGCTGGCTCGCGTCGCTCAGT SapI
            BspQI
GTGAGCGAGGAAGCGGAAGAGCGCCCAATACGCAAACCGCCTCTCCCCGCGCGTTGGCCGATTCA
                                                                          7865
CACTCGCTCCTTCGCCTTCTCGCGGGTTATGCGTTTGGCGGAGAGGGGCGCGCAACCGGCTAAGT

TTAATG       3'
         ***   7871
AATTAC       5'
```

SEQ ID NO:13

FIGURE 3    Sequence: pACASI-GFP-F2A-GPR139-HA-optimized.dna

```
5'  CAGCAGCTGCGCGCTCGCTCGCTCACTGAGGCCGCCCGGGCAAAGCCCGGGCGTCGGGCGACCTT
                                                                              65
3'  GTCGTCGACGCGCGAGCGAGCGAGTGACTCCGGCGGGCCCGTTTCGGGCCCGCAGCCCGCTGGAA

TGGTCGCCCGGCCTCAGTGAGCGAGCGAGCGCGCAGAGAGGGAGTGGCCAACTCCATCACTAGGG
                                                                              130
    ACCAGCGGGCCGGAGTCACTCGCTCGCTCGCGCGTCTCTCCCTCACCGGTTGAGGTAGTGATCCC

GTTCCTTGTAGTTAATGATTAACCCGCCATGCTACTTATCTACGTAGCCATGCTCTAGGACATTG
                                                                              195
    CAAGGAACATCAATTACTAATTGGGCGGTACGATGAATAGATGCATCGGTACGAGATCCTGTAAC
                                                                CMV enhancer SpeI
    ATTATTGACTAGTggagttccgcgttacataacttacggtaaatggcccgcctggctgaccgcc
                                                                              260
    TAATAACTGATCAccctcaaggcgcaatgtattgaatgccatttaccgggcggaccgactggcggg
    CMV enhancer                       CASI promoter
                                   CMV enhancer aacgaccccgcccattgacgtcaataatgacgtatgttcccatagtaacgccaatagggactt t
                                                                              325
    ttgctgggggcgggtaactgcagttattactgcatacaagggtatcattgcggttatccctgaaa
                                       CASI promoter
                               CMV enhancer ccattgacgtcaatgggtggagtatttacggtaaactgcccacttggcagtacatcaagtgtatc
                                                                              390
    ggtaactgcagttacccacctcataaatgccatttgacgggtgaaccgtcatgtagttcacatag
                                       CASI promoter
                               CMV enhancer atatgccaagtacgcccctattgacgtcaatgacggtaaatggcccgcctggcattatgcccag
                                                                              455
    tatacggttcatgcgggggataactgcagttactgccatttaccgggcggaccgtaatacgggtc
                                       CASI promoter
                               CMV enhancer tacatgaccttatgggactttcctacttggcagtacatctacgtattagtcatcgctattaccat
                                                                              520
    atgtactggaataccctgaaaggatgaaccgtcatgtagatgcataatcagtagcgataatggta
                                       CASI promoter
                               CMV enhancer
```

FIGURE 3 Continued

```
ggtcgaggtgagccccacgttctgcttcactctccccatctcccccccctccccaccccaattt
ccagctccactcgggGtgcaagacgaagtgagaggggtagagggggggaggggtggggttaaa      585
                                   CASI promoter
                             chicken β-actin promoter                  >
CMV enhancer tgtatttatttattttttaattattttgtgcagcgatggGggcggggggggggggggcgcgcgc
acataaataaaaaattaataaaacacgtcgctaccccgccccccccccccccgcgcgcg           650
                                   CASI promoter
                             chicken β-actin promoter                  > caggcggggcggggcggggcgagggcgGggcggggcgaggcggagaggtgcggcggcagccaat
gtccgccccgccccgccccgctcccgccccgccccgctccgcctctccacgccgccgtcggtta      715
                                   CASI promoter
                             chicken β-actin promoter                  > cagagcggcgcgctccgaaagttttccttttatggcgaggcggcggcggcggcggccctataaaaa
gtctcgccgcgcgaggctttcaaaggaaaataccgctccgccgccgccgccgggatatttttt      780
                                   CASI promoter
                             chicken β-actin promoter                  > gcgaagcgcgcggcgggcgggagtcgctgcgcgctgccttcgccccgtgccccgctccgccgccg
cgcttcgcgcgccgcccgccctcagcgacgcgcgacggaagcggggcacggggcgaggcggcggc      845
                                   CASI promoter
chicken β-actin promoter > cctcgcgccgcccgccccggctctgactgaccgcgttactaaaacaggtaagtccggcctccgcg
ggagcgcggcgggcggggccgagactgactggcgcaatgattttgtccattcaggccggaggcgc    910
                                   CASI promoter AfeI
ccgggttttggcgcctccgcgggcgcccccctcctcacggcgagcgctgccacgtcagacgaag
ggcccaaaaccgcggagggcgcccgcgggggggaggagtgccgctcgcgacggtgcagtctgcttc    975
                                   CASI promoter ggcgcagcgagcgtcctgatccttccgcccggacgctcaggacagcggcccgctgctcataagac
ccgcgtcgctcgcaggactaggaaggcgggcctgcgagtcctgtcgccgggcgacgagtattctg    1040
                                   CASI promoter tcggccttagaaccccagtatcagcagaaggacattttaggacgggacttgggtgactctagggc
agccggaatcttggggtcatagtcgtcttcctgtaaaatcctgccctgaacccactgagatcccg    1105
                                   CASI promoter
```

FIGURE 3 Continued

```
actggttttctttccagagagcggaacaggcgaggaaaagtagtcccttctcggcgattctgcgg          1170
tgaccaaaagaaaggtctctcgccttgtccgctccttttcatcagggaagagccgctaagacgc
                              CASI promoter agggatctccgtggggcggtgaacgccgatgatgcctctactaaccatgttcatgttttcttttt          1235
tcctagaggcaccccgccacttgcggctactacggagatgattggtacaagtacaaaagaaaaa
                              CASI promoter Acc65I    KpnI
ttttctacaggtcctgggtgacgaacagGGTACCGCCACCATGGTGTCCAAGGGAGAGGAGCTGT          1300
aaaagatgtccaggaccactgcttgtcCCATGGCGGTGGTACCACAGGTTCCCTCTCCTCGACA
                                                  M  V  S  K  G  E  E  L
        CASI promoter              KpnI   Kozak    eGFP mouse-human codon optimized TCACCGGAGTGGTGCCCATCCTGGTGGAGCTGGACGGCGATGTGAATGGCCACAAGTTTAGCGTG         1365
AGTGGCCTCACCACGGGTAGGACCACCTCGACCTGCCGCTACACTTACCGGTGTTCAAATCGCAC
      10              15              20              25              30
 F  T  G  V  V  P  I  L  V  E  L  D  G  D  V  N  G  H  K  F  S  V
                       eGFP mouse-human codon optimized BspEI
TCCGGAGAGGGAGAGGGCGACGCAACCTACGGCAAGCTGACACTGAAGTTCATCTGCACCACAGG         1430
AGGCCTCTCCCTCTCCCGCTGCGTTGGATGCCGTTCGACTGTGACTTCAAGTAGACGTGGTGTCC
       35              40              45              50
 S  G  E  G  E  G  D  A  T  Y  G  K  L  T  L  K  F  I  C  T  T  G
                       eGFP mouse-human codon optimized BstEII
CAAGCTGCCCGTGCCTTGGCCAACCCTGGTGACCACACTGACATACGGCGTGCAGTGTTTTCTC         1495
GTTCGACGGGCACGGAACCGGTTGGGACCACTGGTGTGACTGTATGCCGCACGTCACAAAAGAG
         55              60              65              70
 K  L  P  V  P  W  P  T  L  V  T  T  L  T  Y  G  V  Q  C  F  S
                       eGFP mouse-human codon optimized GGTATCCAGACCACATGAAGCAGCACGATTTCTTTAAGAGCGCCATGCCCGAGGGCTACGTGCAG         1560
CCATAGGTCTGGTGTACTTCGTCGTGCTAAAGAAATTCTCGCGGTACGGGCTCCCGATGCACGTC
      75              80              85              90              95
 R  Y  P  D  H  M  K  Q  H  D  F  F  K  S  A  M  P  E  G  Y  V  Q
                       eGFP mouse-human codon optimized GAGAGGACAATCTTCTTTAAGGACGATGGCAACTATAAGACCAGAGCCGAGGTGAAGTTCGAGGG         1625
CTCTCCTGTTAGAAGAAATTCCTGCTACCGTTGATATTCTGGTCTCGGCTCCACTTCAAGCTCCC
          100             105             110             115
 E  R  T  I  F  F  K  D  D  G  N  Y  K  T  R  A  E  V  K  F  E  G
                       eGFP mouse-human codon optimized CGACACACTGGTGAACCGGATCGAGCTGAAGGGCATCGACTTTAAGGAGGATGGCAATATCCTGG         1690
GCTGTGTGACCACTTGGCCTAGCTCGACTTCCCGTAGCTGAAATTCCTCCTACCGTTATAGGACC
         120             125             130             135
 D  T  L  V  N  R  I  E  L  K  G  I  D  F  K  E  D  G  N  I  L
                       eGFP mouse-human codon optimized
```

FIGURE 3 Continued

```
GCCACAAGCTGGAGTACAACTATAATTCCCACAACGTGTACATCATGGCCGATAAGCAGAAGAAC
CGGTGTTCGACCTCATGTTGATATTAAGGGTGTTGCACATGTAGTACCGGCTATTCGTCTTCTTG
       140         145         150         155         160
  G  H  K  L  E  Y  N  Y  N  S  H  N  V  Y  I  M  A  D  K  Q  K  N
                          eGFP mouse-human codon optimized                  >
```
1755

```
GGCATCAAGGTGAACTTCAAGATCCGCCACAATATCGAGGACGGCTCTGTGCAGCTGGCCGATCA
CCGTAGTTCCACTTGAAGTTCTAGGCGGTGTTATAGCTCCTGCCGAGACACGTCGACCGGCTAGT
       165         170         175         180
  G  I  K  V  N  F  K  I  R  H  N  I  E  D  G  S  V  Q  L  A  D  H
                          eGFP mouse-human codon optimized                  >
```
1820

```
                                                              AccI
CTACCAGCAGAACACCCCTATCGGCGACGGACCCGTGCTGCTGCCTGATAATCACTATCTGTCTA
GATGGTCGTCTTGTGGGGATAGCCGCTGCCTGGGCACGACGACGGACTATTAGTGATAGACAGAT
       185         190         195         200
  Y  Q  Q  N  T  P  I  G  D  G  P  V  L  L  P  D  N  H  Y  L  S
                          eGFP mouse-human codon optimized                  >
```
1885

```
         EcoNI
CACAGAGCGCCCTGTCCAAGGACCCAAACGAGAAGAGGGATCACATGGTGCTGCTGGAGTTCGTG
GTGTCTCGCGGGACAGGTTCCTGGGTTTGCTCTTCTCCCTAGTGTACCACGACGACCTCAAGCAC
       205         210         215         220         225
  T  Q  S  A  L  S  K  D  P  N  E  K  R  D  H  M  V  L  L  E  F  V
                          eGFP mouse-human codon optimized                  >
```
1950

```
ACCGCAGCAGGCATCACACTGGGCATGGATGAGCTGTATAAGcgaaaaagaagatcaggttcggg
TGGCGTCGTCCGTAGTGTGACCCGTACCTACTCGACATATTCgcttttcttctagtccaagccc
       230         235                    1         5
  T  A  A  G  I  T  L  G  M  D  E  L  Y  K  R  K  R  S  G  S  G
           eGFP mouse-human codon optimized            F2A optimized        >
```
2015

```
                    AarI
                    BfuAI
                    BspMI
tgcgccagtaaagcagacattaaactttgatttgctgaaacttgcaggtgatgtagagtcaaatc
acgcggtcatttcgtctgtaatttgaaactaaacgactttgaacgtccactacatctcagtttag
     10          15          20          25
  A  P  V  K  Q  T  L  N  F  D  L  L  K  L  A  G  D  V  E  S  N
                              F2A optimized                                 >
```
2080

```
       BamHI
caggtccaggGATCCATGGAGCACACCCACGCACACCTGGCAGCAAACAGCTCCCTGTCCTGGTGG
gtccaggtCCTAGGTACCTCGTGTGGGTGCGTGTGGACCGTCGTTTGTCGAGGGACAGGACCACC
    30      1           1         5          10          15
  P  G  P  G  S  M  E  H  T  H  A  H  L  A  A  N  S  S  L  S  W  W
  F2A optimized  BamHI        GPR-139 mouse-human codon optimized           >
```
2145

```
TCTCCTGGCAGCGCCTGCGGACTGGGCTTCGTGCCAGTGGTGTACTATAGCCTGCTGCTGTGCCT
AGAGGACCGTCGCGGACGCCTGACCCGAAGCACGGTCACCACATGATATCGGACGACGACACGGA
       20          25          30          35
  S  P  G  S  A  C  G  L  G  F  V  P  V  V  Y  Y  S  L  L  L  C  L
                     GPR-139 mouse-human codon optimized                    >
```
2210

FIGURE 3 Continued

```
                                   EcoR*                                                                PshAI
GGGACTGCCAGCAAACATCCTGACAGTGATCATCCTGTCCCAGCTGGTGGCCAGGAGACAGAAGT
                                                                                                              2275
CCCTGACGGTCGTTTGTAGGACTGTCACTAGTAGGACAGGGTCGACCACCGGTCCTCTGTCTTCA
      40           45          50          55          60
   G  L  P  A  N  I  L  T  V  I  L  S  Q  L  V  A  R  R  Q  K
                    GPR-139 mouse-human codon optimized CTAGCTACAATTATCTGCTGGCCCTGGCAGCAGCAGACATCCTGGTGCTGTTCTTTATCGTGTTC
                                                                                                              2340
GATCGATGTTAATAGACGACCGGGACCGTCGTCGTCTGTAGGACCACGACAAGAAATAGCACAAG
           65          70          75          80
   S  S  Y  N  Y  L  L  A  L  A  A  A  D  I  L  V  L  F  F  I  V  F
                    GPR-139 mouse-human codon optimized GTGGACTTTCTGCTGGAGGATTTCATCCTGAACATGCAGATGCCACAGGTGCCCGACAAGATCAT
                                                                                                              2405
CACCTGAAAGACGACCTCCTAAAGTAGGACTTGTACGTCTACGGTGTCCACGGGCTGTTCTAGTA
      85          90          95          100
   V  D  F  L  L  E  D  F  I  L  N  M  Q  M  P  Q  V  P  D  K  I  I
                    GPR-139 mouse-human codon optimized CGAGGTGCTGGAGTTTTCCTCTATCCACACCTCCATCTGGATCACCGTGCCTCTGACAATCGATA
                                                                                                              2470
GCTCCACGACCTCAAAAGGAGATAGGTGTGGAGGTAGACCTAGTGGCACGGAGACTGTTAGCTAT
      105         110         115         120         125
   E  V  L  E  F  S  S  I  H  T  S  I  W  I  T  V  P  L  T  I  D
                    GPR-139 mouse-human codon optimized GGTACATCGCCGTGTGCCACCCACTGAAGTACCACACCGTGTCTTATCCCGCCAGGACAAGAAAA
                                                                                                              2535
CCATGTAGCGGCACACGGTGGGTGACTTCATGGTGTGGCACAGAATAGGGCGGTCCTGTTCTTTT
           130         135         140         145
   R  Y  I  A  V  C  H  P  L  K  Y  H  T  V  S  Y  P  A  R  T  R  K
                    GPR-139 mouse-human codon optimized GTGATCGTGAGCGTGTACATCACCTGTTTCCTGACATCTATCCCCTACTATTGGTGGCCTAATAT
                                                                                                              2600
CACTAGCACTCGCACATGTAGTGGACAAAGGACTGTAGATAGGGGATGATAACCACCGGATTATA
      150         155         160         165
   V  I  V  S  V  Y  I  T  C  F  L  T  S  I  P  Y  Y  W  W  P  N  I
                    GPR-139 mouse-human codon optimized PmlI
CTGGACCGAGGATTACATCTCTACAAGCGTGCACCACGTGCTGATCTGGATTCACTGCTTCACAG
                                                                                                              2665
GACCTGGCTCCTAATGTAGAGATGTTCGCACGTGGTGCACGACTAGACCTAAGTGACGAAGTGTC
      170         175         180         185         190
   W  T  E  D  Y  I  S  T  S  V  H  H  V  L  I  W  I  H  C  F  T
                    GPR-139 mouse-human codon optimized TGTATCTGGTGCCATGTAGCATCTTCTTTATCCTGAACTCCATCATCGTGTACAAGCTGCGGCGC
                                                                                                              2730
ACATAGACCACGGTACATCGTAGAAGAAATAGGACTTGAGGTAGTAGCACATGTTCGACGCCGCG
           195         200         205         210
   V  Y  L  V  P  C  S  I  F  F  I  L  N  S  I  I  V  Y  K  L  R  R
                    GPR-139 mouse-human codon optimized
```

FIGURE 3 Continued

```
           AAGTCTAATTTTCGGCTGCGCGGCTATAGCACCGGCAAGACCACAGCCATCCTGTTCACCATCAC
                                                                                                  2795
           TTCAGATTAAAAGCCGACGCGCCGATATCGTGGCCGTTCTGGTGTCGGTAGGACAAGTGGTAGTG
                215       220        225        230
             K  S  N  F  R  L  R  G  Y  S  T  G  K  T  T  A  I  L  F  T  I  T
                        GPR-139 mouse-human codon optimized           >

PspOMI    ApaI
           ATCCATCTTTGCCACACTGTGGGCCCCACGGATCATCATGATCCTGTACCACCTGTATGGAGCAC
                                                                                                  2860
           TAGGTAGAAACGGTGTGACACCCGGGGTGCCTAGTAGTACTAGGACATGGTGGACATACCTCGTG
              235        240        245        250        255
             S  I  F  A  T  L  W  A  P  R  I  I  M  I  L  Y  H  L  Y  G  A
                        GPR-139 mouse-human codon optimized           >

CAATCCAGAACAGGTGGCTGGTGCACATCATGTCTGACATCGCCAATATGCTGGCCCTGCTGAAC
                                                                                                  2925
           GTTAGGTCTTGTCCACCGACCACGTGTAGTACAGACTGTAGCGGTTATACGACCGGGACGACTTG
                260        265        270        275
             P  I  Q  N  R  W  L  V  H  I  M  S  D  I  A  N  M  L  A  L  L  N
                        GPR-139 mouse-human codon optimized           >

ACCGCCATCAATTTCTTTCTGTACTGCTTCATCAGCAAGAGGTTTAGAACCATGGCCGCCGCCAC
                                                                                                  2990
           TGGCGGTAGTTAAAGAAAGACATGACGAAGTAGTCGTTCTCCAAATCTTGGTACCGGCGGCGGTG
              280        285        290        295
             T  A  I  N  F  F  L  Y  C  F  I  S  K  R  F  R  T  M  A  A  A  T
                        GPR-139 mouse-human codon optimized           >

StuI
           ACTGAAGGCCTTCTTTAAGTGTCAGAAGCAGCCTGTGCAGTTCTACACCAACCACAATTTTTCCA
                                                                                                  3055
           TGACTTCCGGAAGAAATTCACAGTCTTCGTCGGACACGTCAAGATGTGGTTGGTGTTAAAAAGGT
                300        305        310        315         320
             L  K  A  F  F  K  C  Q  K  Q  P  V  Q  F  Y  T  N  H  N  F  S
                        GPR-139 mouse-human codon optimized           >

TCACAAGCTCCCCTTGGATCTCCCCAGCCAACTCTCACTGCATCAAGATGCTGGTGTACCAGTAT
                                                                                                  3120
           AGTGTTCGAGGGGAACCTAGAGGGGTCGGTTGAGAGTGACGTAGTTCTACGACCACATGGTCATA
                325        330        335        340
             T  S  P  W  I  S  P  A  N  S  H  C  I  K  M  L  V  Y  Q  Y
                        GPR-139 mouse-human codon optimized           >

GATAAGAATGGCAAGCCCATCAAGGTGAGCCCCTACCCTTATGACGTGCCTGATTACGCCTGAAT
                                                                                                  3185
           CTATTCTTACCGTTCGGGTAGTTCCACTCGGGGATGGGAATACTGCACGGACTAATGCGGACTTA
                345        350            1      5
             D  K  N  G  K  P  I  K  V  S  P  Y  P  Y  D  V  P  D  Y  A
                 GPR-139 mouse-human codon optimized     >               HA
                                                                                    XbaI XbaI
           CTAGAAtaatcaacctctggattacaaaatttgtgaaagattgactggtattcttaactatgttg
                                                                                                  3250
           GATCTTattagttggagacctaatgttttaaacactttctaactgaccataagaattgatacaac
             XbaI                              WPRE ctccttttacgctatgtggatacgctgctttaatgcctttgtatcatgctattgcttcccgtatg
                                                                                                  3315
           gaggaaaatgcgatacacctatgcgacgaaattacggaaacatagtacgataacgaagggcatac
                                        WPRE
```

FIGURE 3 Continued

```
gctttcattttctcctccttgtataaatcctggttgctgtctctttatgaggagttgtggcccgt
|-|-|-|-|-|-|-|-|-|-|-|-|-|-|-|-|-|-|-|-|-|-|-|-|-|-|-|-|-|-|-|-|-|    3380
cgaaagtaaaagaggaggaacatatttaggaccaacgacagagaaatactcctcaacaccgggca
                                 WPRE tgtcaggcaacgtggcgtggtgtgcactgtgtttgctgacgcaaccccactggttggggcattg
|-|-|-|-|-|-|-|-|-|-|-|-|-|-|-|-|-|-|-|-|-|-|-|-|-|-|-|-|-|-|-|-|-|    3445
acagtccgttgcaccgcaccacacgtgacacaaacgactgcgttggggggtgaccaacccgtaac
                                 WPRE ccaccacctgtcagctcctttccgggactttcgctttcccctccctattgccacggcggaactc
|-|-|-|-|-|-|-|-|-|-|-|-|-|-|-|-|-|-|-|-|-|-|-|-|-|-|-|-|-|-|-|-|-|    3510
ggtggtggacagtcgaggaaaggccctgaaagcgaaaggggagggataacggtgccgccttgag
                                 WPRE atcgccgcctgccttgcccgctgctggacaggggctcggctgttgggcactgacaattccgtggt
|-|-|-|-|-|-|-|-|-|-|-|-|-|-|-|-|-|-|-|-|-|-|-|-|-|-|-|-|-|-|-|-|-|    3575
tagcggcggacggaacgggcgacgacctgtccccgagccgacaacccgtgactgttaaggcacca
                                 WPRE gttgtcggggaaatcatcgtcctttccttggctgctcgcctgtgttgccacctggattctgcgcg
|-|-|-|-|-|-|-|-|-|-|-|-|-|-|-|-|-|-|-|-|-|-|-|-|-|-|-|-|-|-|-|-|-|    3640
caacagccccttttagtagcaggaaaggaaccgacgagcggacacaacggtggacctaagacgcgc
                R  G  K  R  P  Q  E  G  T  N  G  G  P  N  Q  A
              ← (in frame with Factor Xa site)
                                 WPRE ggacgtccttctgctacgtcccttcggccctcaatccagcggaccttccttccgcggcctgctg
|-|-|-|-|-|-|-|-|-|-|-|-|-|-|-|-|-|-|-|-|-|-|-|-|-|-|-|-|-|-|-|-|-|    3705
cctgcaggaagacgatgcagggaagccgggagttaggtcgcctggaaggaagggcgccggacgac
P  R  G  E  A  V  D  R  G  E  I
← (in frame with Factor Xa site)
                                 WPRE BbsI
ccggctctgcggcctcttccgcgtcttcgccttcgccctcagacgagtcggatctccctttgggc
|-|-|-|-|-|-|-|-|-|-|-|-|-|-|-|-|-|-|-|-|-|-|-|-|-|-|-|-|-|-|-|-|-|    3770
ggccgagacgccggagaaggcgcagaagcggaagcgggagtctgctcagcctagagggaaaccccg
                                 WPRE HindIII              BglII
cgcctccccgcctAAGCTTATCGATACCGTCGAGATCTAACTTGTTTATTGCAGCTTATAATGGT
|-|-|-|-|-|-|-|-|-|-|-|-|-|-|-|-|-|-|-|-|-|-|-|-|-|-|-|-|-|-|-|-|-|    3835
gcggaggggcggaTTCGAATAGCTATGGCAGCTCTAGATTGAACAAATAACGTCGAATATTACCA
      WPRE                         SV40 poly(A) signal BsmI
TACAAATAAAGCAATAGCATCACAAATTTCACAAATAAAGCATTTTTTTCACTGCATTCTAGTTG
|-|-|-|-|-|-|-|-|-|-|-|-|-|-|-|-|-|-|-|-|-|-|-|-|-|-|-|-|-|-|-|-|-|    3900
ATGTTTATTTCGTTATCGTAGTGTTTAAAGTGTTTATTTCGTAAAAAAAGTGACGTAAGATCAAC
                        SV40 poly(A) signal
```

FIGURE 3 Continued

```
TGGTTTGTCCAAACTCATCAATGTATCTTATCATGTCTGGATCTCGACCTCGACTAGAGCATGGC
                                                                        3965
ACCAAACAGGTTTGAGTAGTTACATAGAATAGTACAGACCTAGAGCTGGAGCTGATCTCGTACCG
                            SV40 poly(A) signal TACGTAGATAAGTAGCATGGCGGGTTAATCATTAACTACAAGGAACCCCTAGTGATGGAGTTGGC
                                                                        4030
ATGCATCTATTCATCGTACCGCCCAATTAGTAATTGATGTTCCTTGGGGATCACTACCTCAACCG CACTCCCTCTCTGCGCGCTCGCTCGCTCACTGAGGCCGGGCGACCAAAGGTCGCCCGACGCCCGG
                                                                        4095
GTGAGGGAGAGACGCGCGAGCGAGCGAGTGACTCCGGCCCGCTGGTTTCCAGCGGGCTGCGGGCC
                    RBE GCTTTGCCCGGGCGGCCTCAGTGAGCGAGCGAGCGCGCCAGCTGGCGTAATAGCGAAGAGGCCCG
                                                                        4160
CGAAACGGGCCCGCCGGAGTCACTCGCTCGCTCGCGCGGTCGACCGCATTATCGCTTCTCCGGGC
                                RBE CACCGATCGCCCTTCCCAACAGTTGCGCAGCCTGAATGGCGAATGGAATTCCAGACGATTGAGCG
                                                                        4225
GTGGCTAGCGGGAAGGGTTGTCAACGCGTCGGACTTACCGCTTACCTTAAGGTCTGCTAACTCGC TCAAAATGTAGGTATTTCCATGAGCGTTTTTCCTGTTGCAATGGCTGGCGGTAATATTGTTCTGG
                                                                        4290
AGTTTTACATCCATAAAGGTACTCGCAAAAAGGACAACGTTACCGACCGCCATTATAACAAGACC ATATTACCAGCAAGGCCGATAGTTTGAGTTCTTCTACTCAGGCAAGTGATGTTATTACTAATCAA
                                                                        4355
TATAATGGTCGTTCCGGCTATCAAACTCAAGAAGATGAGTCCGTTCACTACAATAATGATTAGTT AGAAGTATTGCGACAACGGTTAATTTGCGTGATGGACAGACTCTTTTACTCGGTGGCCTCACTGA
                                                                        4420
TCTTCATAACGCTGTTGCCAATTAAACGCACTACCTGTCTGAGAAAATGAGCCACCGGAGTGACT TTATAAAACACTTCTCAGGATTCTGGCGTACCGTTCCTGTCTAAAATCCCTTTAATCGGCCTCC
                                                                        4485
AATATTTTGTGAAGAGTCCTAAGACCGCATGGCAAGGACAGATTTTAGGGAAATTAGCCGGAGG TGTTAGCTCCCGCTCTGATTCTAACGAGGAAAGCACGTTATACGTGCTCGTCAAAGCAACCATA
                                                                        4550
ACAAATCGAGGGCGAGACTAAGATTGCTCCTTTCGTGCAATATGCACGAGCAGTTTCGTTGGTAT GTACGCGCCCTGTAGCGGCGCATTAAGCGCGGCGGGTGTGGTGGTTACGCGCAGCGTGACCGCTA
                                                                        4615
CATGCGCGGGACATCGCCGCGTAATTCGCGCCGCCCACACCACCAATGCGCGTCGCACTGGCGAT
                                    f1 ori CACTTGCCAGCGCCCTAGCGCCCGCTCCTTTCGCTTTCTTCCCTTCCTTTCTCGCCACGTTCGCC
                                                                        4680
GTGAACGGTCGCGGGATCGCGGGCGAGGAAAGCGAAAGAAGGGAAGGAAAGAGCGGTGCAAGCGG
                                    f1 ori
```

FIGURE 3 Continued

```
GGCTTTCCCCGTCAAGCTCTAAATCGGGGGCTCCCTTTAGGGTTCCGATTTAGTGCTTTACGGCA
                                                                                4745
CCGAAAGGGGCAGTTCGAGATTTAGCCCCCGAGGGAAATCCCAAGGCTAAATCACGAAATGCCGT
                              f1 ori                                          >

CCTCGACCCCAAAAAACTTGATTAGGGTGATGGTTCACGTAGTGGGCCATCGCCCTGATAGACGG
                                                                                4810
GGAGCTGGGGTTTTTTGAACTAATCCCACTACCAAGTGCATCACCCGGTAGCGGGACTATCTGCC
                              f1 ori                                          >

TTTTTCGCCCTTTGACGTTGGAGTCCACGTTCTTTAATAGTGGACTCTTGTTCCAAACTGGAACA
                                                                                4875
AAAAAGCGGGAAACTGCAACCTCAGGTGCAAGAAATTATCACCTGAGAACAAGGTTTGACCTTGT
                              f1 ori                                          >

ACACTCAACCCTATCTCGGTCTATTCTTTTGATTTATAAGGGATTTTGCCGATTTCGGCCTATTG
                                                                                4940
TGTGAGTTGGGATAGAGCCAGATAAGAAAACTAAATATTCCCTAAAACGGCTAAAGCCGGATAAC
                              f1 ori                                          >

GTTAAAAAATGAGCTGATTTAACAAAAATTTAACGCGAATTTTAACAAAATATTAACGTTTACAA
                                                                                5005
CAATTTTTTACTCGACTAAATTGTTTTTAAATTGCGCTTAAAATTGTTTTATAATTGCAAATGTT
                              f1 ori                                          >

SwaI
TTTAAATATTTGCTTATACAATCTTCCTGTTTTTGGGGCTTTTCTGATTATCAACCGGGGTACAT
                                                                                5070
AAATTTATAAACGAATATGTTAGAAGGACAAAAACCCCGAAAAGACTAATAGTTGGCCCCATGTA
 >
f1 ori ATGATTGACATGCTAGTTTTACGATTACCGTTCATCGATTCTCTTGTTTGCTCCAGACTCTCAGG
                                                                                5135
TACTAACTGTACGATCAAAATGCTAATGGCAAGTAGCTAAGAGAACAAACGAGGTCTGAGAGTCC CAATGACCTGATAGCCTTTGTAGAGACCTCTCAAAAATAGCTACCCTCTCCGGCATGAATTTATC
                                                                                5200
GTTACTGGACTATCGGAAACATCTCTGGAGAGTTTTATCGATGGGAGAGGCCGTACTTAAATAG AGCTAGAACGGTTGAATATCATATTGATGGTGATTTGACTGTCTCCGGCCTTTCTCACCCGTTTG
                                                                                5265
TCGATCTTGCCAACTTATAGTATAACTACCACTAAACTGACAGAGGCCGGAAAGAGTGGGCAAAC AATCTTTACCTACACATTACTCAGGCATTGCATTTAAAATATATGAGGGTTCTAAAAATTTTTAT
                                                                                5330
TTAGAAATGGATGTGTAATGAGTCCGTAACGTAAATTTTATATACTCCCAAGATTTTTAAAAATA CCTTGCGTTGAAATAAAGGCTTCTCCCGCAAAAGTATTACAGGGTCATAATGTTTTTGGTACAAC
                                                                                5395
GGAACGCAACTTTATTTCCGAAGAGGGCGTTTTCATAATGTCCCAGTATTACAAAAACCATGTTG CGATTTAGCTTTATGCTCTGAGGCTTTATTGCTTAATTTTGCTAATTCTTTGCCTTGCCTGTATG
                                                                                5460
GCTAAATCGAAATACGAGACTCCGAAATAACGAATTAAAACGATTAAGAAACGGAACGGACATAC
```

FIGURE 3 Continued

```
ATTTATTGGATGTTGGAATTCCTGATGCGGTATTTTCTCCTTACGCATCTGTGCGGTATTTCACA
                                                                        5525
TAAATAACCTACAACCTTAAGGACTACGCCATAAAAGAGGAATGCGTAGACACGCCATAAAGTGT

CCGCATATGGTGCACTCTCAGTACAATCTGCTCTGATGCCGCATAGTTAAGCCAGCCCCGACACC
                                                                        5590
GGCGTATACCACGTGAGAGTCATGTTAGACGAGACTACGGCGTATCAATTCGGTCGGGGCTGTGG

CGCCAACACCCGCTGACGCGCCCTGACGGGCTTGTCTGCTCCCGGCATCCGCTTACAGACAAGCT
                                                                        5655
GCGGTTGTGGGCGACTGCGCGGGACTGCCCGAACAGACGAGGGCCGTAGGCGAATGTCTGTTCGA

GTGACCGTCTCCGGGAGCTGCATGTGTCAGAGGTTTTCACCGTCATCACCGAAACGCGCGAGACG
                                                                        5720
CACTGGCAGAGGCCCTCGACGTACACAGTCTCCAAAAGTGGCAGTAGTGGCTTTGCGCGCTCTGC

AAAGGGCCTCGTGATACGCCTATTTTTATAGGTTAATGTCATGATAATAATGGTTTCTTAGACGT
                                                                        5785
TTTCCCGGAGCACTATGCGGATAAAAATATCCAATTACAGTACTATTATTACCAAAGAATCTGCA

CAGGTGGCACTTTTCGGGGAAATGTGCGCGGAACCCCTATTTGTTTATTTTTCTAAATACATTCA
                                                                        5850
GTCCACCGTGAAAAGCCCCTTTACACGCGCCTTGGGGATAAACAAATAAAAGATTTATGTAAGT
                                           [————— AmpR promoter ————>

AATATGTATCCGCTCATGAGACAATAACCCTGATAAATGCTTCAATAATATTGAAAAAGGAAGAG
                                                                        5915
TTATACATAGGCGAGTACTCTGTTATTGGGACTATTTACGAAGTTATTATAACTTTTTCCTTCTC
————————————— AmpR promoter —————————————>

TATGAGTATTCAACATTTCCGTGTCGCCCTTATTCCCTTTTTTGCGGCATTTTGCCTTCCTGTTT
                                                                        5980
ATACTCATAAGTTGTAAAGGCACAGCGGGAATAAGGGAAAAAACGCCGTAAAACGGAAGGACAAA
     1         5        10         15        20
     M  S  I  Q  H  F  R  V  A  L  I  P  F  F  A  A  F  C  L  P  V
———————————————— signal sequence ———————————————>
                    AmpR
AmpR promoter TTGCTCACCCAGAAACGCTGGTGAAAGTAAAAGATGCTGAAGATCAGTTGGGTGCACGAGTGGGT
                                                                        6045
AACGAGTGGGTCTTTGCGACCACTTTCATTTTCTACGACTTCTAGTCAACCCACGTGCTCACCCA
        25        30        35        40
  F  A  H  P  E  T  L  V  K  V  K  D  A  E  D  Q  L  G  A  R  V  G
 signal |
                    AmpR TACATCGAACTGGATCTCAACAGCGGTAAGATCCTTGAGAGTTTTCGCCCCGAAGAACGTTTTCC
                                                                        6110
ATGTAGCTTGACCTAGAGTTGTCGCCATTCTAGGAACTCTCAAAAGCGGGGCTTCTTGCAAAAGG
    45        50        55        60        65
  Y  I  E  L  D  L  N  S  G  K  I  L  E  S  F  R  P  E  E  R  F  P
                    AmpR AATGATGAGCACTTTTAAAGTTCTGCTATGTGGCGCGGTATTATCCCGTATTGACGCCGGGCAAG
                                                                        6175
TTACTACTCGTGAAAATTTCAAGACGATACACCGCGCCATAATAGGGCATAACTGCGGCCCGTTC
        70        75        80        85
  M  M  S  T  F  K  V  L  L  C  G  A  V  L  S  R  I  D  A  G  Q
                    AmpR
```

FIGURE 3 Continued

```
CACGACGGGGAGTCAGGCAACTATGGATGAACGAAATAGACAGATCGCTGAGATAGGTGCCTCAC
                                                                          6760
GTGCTGCCCCTCAGTCCGTTGATACCTACTTGCTTTATCTGTCTAGCGACTCTATCCACGGAGTG
          265       270         275        280
     T  T  G  S  Q  A  T  M  D  E  R  N  R  Q  I  A  E  I  G  A  S
                              AmpR

TGATTAAGCATTGGTAACTGTCAGACCAAGTTTACTCATATATACTTTAGATTGATTTAAAACTT
                                                                          6825
ACTAATTCGTAACCATTGACAGTCTGGTTCAAATGAGTATATATGAAATCTAACTAAATTTTGAA
           285
     L  I  K  H  W  *
              AmpR

CATTTTTAATTTAAAAGGATCTAGGTGAAGATCCTTTTTGATAATCTCATGACCAAAATCCCTTA
                                                                          6890
GTAAAAATTAAATTTTCCTAGATCCACTTCTAGGAAAAACTATTAGAGTACTGGTTTTAGGGAAT

ACGTGAGTTTTCGTTCCACTGAGCGTCAGACCCCGTAGAAAAGATCAAAGGATCTTCTTGAGATC
                                                                          6955
TGCACTCAAAAGCAAGGTGACTCGCAGTCTGGGGCATCTTTTCTAGTTTCCTAGAAGAACTCTAG
                                                                  ori CTTTTTTTCTGCGCGTAATCTGCTGCTTGCAAACAAAAAAACCACCGCTACCAGCGGTGGTTTGT
                                                                          7020
GAAAAAAGACGCGCATTAGACGACGAACGTTTGTTTTTTGGTGGCGATGGTCGCCACCAAACA
                                  ori TTGCCGGATCAAGAGCTACCAACTCTTTTTCCGAAGGTAACTGGCTTCAGCAGAGCGCAGATACC
                                                                          7085
AACGGCCTAGTTCTCGATGGTTGAGAAAAAGGCTTCCATTGACCGAAGTCGTCTCGCGTCTATGG
                                  ori AAATACTGTCCTTCTAGTGTAGCCGTAGTTAGGCCACCACTTCAAGAACTCTGTAGCACCGCCTA
                                                                          7150
TTTATGACAGGAAGATCACATCGGCATCAATCCGGTGGTGAAGTTCTTGAGACATCGTGGCGGAT
                                  ori CATACCTCGCTCTGCTAATCCTGTTACCAGTGGCTGCTGCCAGTGGCGATAAGTCGTGTCTTACC
                                                                          7215
GTATGGAGCGAGACGATTAGGACAATGGTCACCGACGACGGTCACCGCTATTCAGCACAGAATGG
                                  ori GGGTTGGACTCAAGACGATAGTTACCGGATAAGGCGCAGCGGTCGGGCTGAACGGGGGGTTCGTG
                                                                          7280
CCCAACCTGAGTTCTGCTATCAATGGCCTATTCCGCGTCGCCAGCCCGACTTGCCCCCCAAGCAC
                                  ori CACACAGCCCAGCTTGGAGCGAACGACCTACACCGAACTGAGATACCTACAGCGTGAGCTATGAG
                                                                          7345
GTGTGTCGGGTCGAACCTCGCTTGCTGGATGTGGCTTGACTCTATGGATGTCGCACTCGATACTC
                                  ori AAAGCGCCACGCTTCCCGAAGGGAGAAAGGCGGACAGGTATCCGGTAAGCGGCAGGGTCGGAACA
                                                                          7410
TTTCGCGGTGCGAAGGGCTTCCCTCTTTCCGCCTGTCCATAGGCCATTCGCCGTCCCAGCCTTGT
                                  ori
```

FIGURE 3 Concluded

```
GGAGAGCGCACGAGGGAGCTTCCAGGGGGAAACGCCTGGTATCTTTATAGTCCTGTCGGGTTTCG
CCTCTCGCGTGCTCCCTCGAAGGTCCCCCTTTGCGGACCATAGAAATATCAGGACAGCCCAAAGC         7475
                                  ori                                  >

CCACCTCTGACTTGAGCGTCGATTTTTGTGATGCTCGTCAGGGGGGCGGAGCCTATGGAAAAACG
GGTGGAGACTGAACTCGCAGCTAAAAACACTACGAGCAGTCCCCCCGCCTCGGATACCTTTTTGC         7540
                                  ori                                  >

PciI
CCAGCAACGCGGCCTTTTTACGGTTCCTGGCCTTTTGCTGGCCTTTTGCTCACATGTTCTTTCCT
GGTCGTTGCGCCGGAAAAATGCCAAGGACCGGAAAACGACCGGAAAACGAGTGTACAAGAAAGGA         7605

GCGTTATCCCCTGATTCTGTGGATAACCGTATTACCGCCTTTGAGTGAGCTGATACCGCTCGCCG
CGCAATAGGGGACTAAGACACCTATTGGCATAATGGCGGAAACTCACTCGACTATGGCGAGCGGC         7670

SapI
                                      BspQI
CAGCCGAACGACCGAGCGCAGCGAGTCAGTGAGCGAGGAAGCGGAAGAGCGCCCAATACGCAAAC
GTCGGCTTGCTGGCTCGCGTCGCTCAGTCACTCGCTCCTTCGCCTTCTCGCGGGTTATGCGTTTG         7735

CGCCTCTCCCCGCGCGTTGGCCGATTCATTAATG        3'
GCGGAGAGGGGCGCGCAACCGGCTAAGTAATTAC   ***  7769
                                          5'
```

SEQ ID NO:14

SEQUENCE LISTING

<160> NUMBER OF SEQ ID NOS: 14

<210> SEQ ID NO 1
<211> LENGTH: 1338
<212> TYPE: DNA
<213> ORGANISM: Artificial Sequence
<220> FEATURE:
<223> OTHER INFORMATION: Synthetic polynucleotide

<400> SEQUENCE: 1

| | |
|---|---|
| atgaggacac tgaatacctc tgccatggat ggcacaggcc tggtggtgga gagggacttt | 60 |
| agcgtgagaa tcctgaccgc ctgcttcctg agcctgctga tcctgtccac actgctgggc | 120 |
| aatacccttgg tgtgcgccgc cgtgatccgg tttcgccacc tgagatccaa ggtgacaaac | 180 |
| ttctttgtga tcagcctggc cgtgtccgat ctgctggtgg ccgtgctggt catgccttgg | 240 |
| aaggcagtgg cagagatcgc aggattctgg ccatttggct cttttctgcaa tatctgggtg | 300 |
| gccttcgata tcatgtgctc caccgcctct atcctgaacc tgtgcgtgat cagcgtggac | 360 |
| cggtactggg ccatcagctc ccccttcagg tacgagagaa agatgacacc caaggccgcc | 420 |
| ttcatcctga tcagcgtggc ctggaccctg tctgtgctga tcagctttat ccccgtgcag | 480 |
| ctgtcctggc acaaggccaa gcccacaagc ccttccgacg gcaatgccac atctctggcc | 540 |
| gagaccatcg ataactgtga ctctagcctg agccgcacct acgccatctc ctctagcgtg | 600 |
| atctccttct atatccctgt ggccatcatg atcgtgacat acacccggat ctatcgcatc | 660 |
| gcccagaagc agatcaggag aatcgccgcc ctggagaggg cagcagtgca cgccaagaat | 720 |
| tgccagacca caaccggcaa cggcaagcct gtggagtgtt ctcagccaga gtcctctttc | 780 |
| aagatgagct ttaagagaga gacaaaggtg ctgaagaccc tgtccgtgat catgggcgtg | 840 |
| ttcgtgtgct gttggctgcc tttctttatc ctgaattgca tcctgccatt tgtggctcc | 900 |
| ggcgagacac agcccttctg catcgattct aacacctttg acgtgttcgt gtggtttggc | 960 |
| tgggccaata gctccctgaa ccctatcatc tacgccttca atgccgattt tcggaaggcc | 1020 |
| ttcagcaccc tgctgggctg ctatcgcctg tgcccagcca caaacaatgc catcgagacc | 1080 |
| gtgtccatca caataacgg cgccgccatg ttctctagcc accacgagcc ccggggctct | 1140 |
| atcagcaagg agtgtaacct ggtgtacctg atccctcacg ccgtgggctc ctctgaggac | 1200 |
| ctgaagaagg aggaggcagc aggaatcgca aggcccctgg agaagctgtc ccctgccctg | 1260 |
| tctgtgatcc tggactacga taccgacgtg agcctggaga agatccagcc aatcacacag | 1320 |
| aacggccagc acccaacc | 1338 |

<210> SEQ ID NO 2
<211> LENGTH: 1055
<212> TYPE: DNA
<213> ORGANISM: Artificial Sequence
<220> FEATURE:
<223> OTHER INFORMATION: Synthetic polynucleotide

<400> SEQUENCE: 2

| | |
|---|---|
| ggagttccgc gttacataac ttacggtaaa tggcccgcct ggctgaccgc ccaacgaccc | 60 |
| ccgcccattg acgtcaataa tgacgtatgt tcccatagta acgccaatag ggactttcca | 120 |
| ttgacgtcaa tgggtggagt atttacggta aactgcccac ttggcagtac atcaagtgta | 180 |
| tcatatgcca agtacgcccc ctattgacgt caatgacggt aaatggcccg cctggcatta | 240 |
| tgcccagtac atgaccttat gggactttcc tacttggcag tacatctacg tattagtcat | 300 |
| cgctattacc atggtcgagg tgagccccac gttctgcttc actctcccca tctcccccc | 360 |

```
ctccccaccc ccaatttgt atttatttat tttttaatta ttttgtgcag cgatggggc      420 ggggggggg ggggcgcgc gccaggcggg gcggggcggg gcgaggggcg gggcggggcg      480
aggcggagag gtgcggcggc agccaatcag agcggcgcgc tccgaaagtt tccttttatg   540
gcgaggcggc ggcggcggcg gccctataaa aagcgaagcg cgcggcgggc gggagtcgct   600
gcgcgctgcc ttcgccccgt gccccgctcc gccgccgcct cgcgccgccc gccccggctc   660
tgactgaccg cgttactaaa acaggtaagt ccggcctccg cgccgggttt tggcgcctcc   720
cgcgggcgcc cccctcctca cggcgagcgc tgccacgtca gacgaagggc gcagcgagcg   780
tcctgatcct tccgcccgga cgctcaggac agccggcccgc tgctcataag actcggcctt   840
agaaccccag tatcagcaga aggacatttt aggacgggac ttgggtgact ctagggcact   900
ggttttcttt ccagagagcg gaacaggcga ggaaaagtag tcccttctcg gcgattctgc   960
ggagggatct ccgtggggcg gtgaacgccg atgatgcctc tactaaccat gttcatgttt   1020 tcttttttt tctacaggtc ctgggtgacg aacag                              1055
```

```
<210> SEQ ID NO 3
<211> LENGTH: 589
<212> TYPE: DNA
<213> ORGANISM: Artificial Sequence
<220> FEATURE:
<223> OTHER INFORMATION: Woodchuck hepatitis virus posttranscriptional
      regulatory element

<400> SEQUENCE: 3
```

```
aatcaacctc tggattacaa aatttgtgaa agattgactg gtattcttaa ctatgttgct     60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact   240 ggttggggca ttgccaccac ctgtcagctc ctttccggga cttttgcttt ccccctcctt   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgc                589
```

```
<210> SEQ ID NO 4
<211> LENGTH: 130
<212> TYPE: DNA
<213> ORGANISM: Artificial Sequence
<220> FEATURE:
<223> OTHER INFORMATION: AAV 5' ITR sequence

<400> SEQUENCE: 4
```

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct                                                          130
```

```
<210> SEQ ID NO 5
<211> LENGTH: 128
<212> TYPE: DNA
<213> ORGANISM: Artificial Sequence
<220> FEATURE:
<223> OTHER INFORMATION: AAV2 3' ITR sequence
```

<400> SEQUENCE: 5

```
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgc                                                            128
```

<210> SEQ ID NO 6
<211> LENGTH: 4406
<212> TYPE: DNA
<213> ORGANISM: Artificial Sequence
<220> FEATURE:
<223> OTHER INFORMATION: DRD1 expression cassette sequence

<400> SEQUENCE: 6

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct tgtagttaat gattaacccg ccatgctact tatctacgta gccatgctct   180
aggacattga ttattgacta gtggagttcc gcgttacata acttacggta aatggcccgc   240
ctggctgacc gcccaacgac ccccgcccat tgacgtcaat aatgacgtat gttcccatag   300
taacgccaat agggactttc cattgacgtc aatgggtgga gtatttacgg taaactgccc   360
acttggcagt acatcaagtg tatcatatgc caagtacgcc ccctattgac gtcaatgacg   420
gtaaatggcc cgcctggcat tatgcccagt acatgacctt atgggacttt cctacttggc   480
agtacatcta cgtattagtc atcgctatta ccatggtcga ggtgagcccc acgttctgct   540
tcactctccc catctccccc cctccccac ccccaatttt gtatttattt attttttaat    600
tattttgtgc agcgatgggg gcgggggggg ggggggcgc gcgccaggcg gggcggggcg    660
gggcgagggg cggggcgggg cgaggcggag aggtgcggcg gcagccaatc agagcggcgc   720
gctccgaaag tttccttttta tggcgaggcg gcggcggcgg cggccctata aaaagcgaag   780
cgcgcggcgg gcgggagtcg ctgcgcgctg ccttcgcccc gtgccccgct ccgccgccgc   840
ctcgcgccgc ccgccccggc tctgactgac cgcgttacta aaacaggtaa gtccggcctc   900
cgcgccgggt tttggcgcct cccgcgggcg ccccctcct cacggcgagc gctgccacgt    960
cagacgaagg gcgcagcgag cgtcctgatc cttccgcccg gacgctcagg acagcggccc   1020
gctgctcata agactcggcc ttagaacccc agtatcagca aaggacatt ttaggacggg    1080
acttgggtga ctctagggca ctggttttct ttccagagag cggaacaggc gaggaaaagt   1140
agtcccttct cggcgattct gcggagggat ctccgtgggg cggtgaacgc cgatgatgcc   1200
tctactaacc atgttcatgt tttctttttt tttctacagg tcctgggtga cgaacagggt   1260
accgccacca tggtgtccaa gggagaggag ctgttcaccg agtggtgcc catcctggtg    1320
gagctggacg gcgatgtgaa tggccacaag tttagcgtgt ccggagaggg agagggcgac   1380
gcaacctacg gcaagctgac actgaagttc atctgcacca caggcaagct gcccgtgcct   1440
tggccaaccc tggtgaccac actgacatac ggcgtgcagt gttttttctcg gtatccagac   1500
cacatgaagc agcacgattt ctttaagagc gccatgcccg agggctacgt gcaggagagg   1560
acaatcttct ttaaggacga tggcaactat aagaccagcc gaggtgaa gttcgagggc    1620
gacacactgg tgaaccggat cgagctgaag ggcatcgact ttaaggagga tggcaatatc   1680
ctgggccaca gctggagtta caactataat tcccacaacg tgtacatcat ggccgataag   1740
cagaagaacg gcatcaaggt gaacttcaag atccgccaca atatcgagga cggctctgtg   1800
```

```
cagctggccg atcactacca gcagaacacc cctatcggcg acggacccgt gctgctgcct      1860
gataatcact atctgtctac acagagcgcc ctgtccaagg acccaaacga aagagggat       1920 cacatggtgc tgctggagtt cgtgaccgca gcaggcatca cactgggcat ggatgagctg     1980
tataagcgaa aaagaagatc aggttcgggt gcgccagtaa agcagacatt aaactttgat    2040
ttgctgaaac ttgcaggtga tgtagagtca atccaggtc caggatccat gaggacactg     2100
aatacctctg ccatggatgg cacaggcctg gtggtggaga gggactttag cgtgagaatc    2160
ctgaccgcct gcttcctgag cctgctgatc ctgtccacac tgctgggcaa taccctggtg   2220
tgcgccgccg tgatccggtt cgccacctg agatccaagg tgacaaactt ctttgtgatc     2280
agcctggccg tgtccgatct gctggtggcc gtgctggtca tgccttggaa ggcagtggca    2340
gagatcgcag gattctggcc atttggctct tctgcaata tctgggtggc cttcgatatc     2400
atgtgctcca ccgcctctat cctgaacctg tgcgtgatca gcgtggaccg gtactgggcc   2460
atcagctccc ccttcaggta cgagagaaag atgacaccca aggccgcctt catcctgatc   2520
agcgtggcct ggaccctgtc tgtgctgatc agctttatcc ccgtgcagct gtcctggcac   2580
aaggccaagc ccacaagccc ttccgacggc aatgccacat ctctggccga gaccatcgat  2640
aactgtgact ctagcctgag ccgcacctac gccatctcct ctagcgtgat ctccttctat   2700
atccctgtgg ccatcatgat cgtgacatac acccggatct atcgcatcgc ccagaagcag  2760
atcaggagaa tcgccgccct ggagagggca gcagtgcacg ccaagaattg ccagaccaca   2820
accggcaacg gcaagcctgt ggagtgttct cagccagagt cctctttcaa gatgagcttt    2880
aagagagaga caaaggtgct gaagaccctg tccgtgatca tgggcgtgtt cgtgtgctgt  2940 tggctgccttt tctttatcct gaattgcatc ctgccatttt gtggctccgg cgagacacag  3000
cccttctgca tcgattctaa caccctttgac gtgttcgtgt ggtttggctg ggccaatagc  3060
tccctgaacc ctatcatcta cgccttcaat gccgattttc ggaaggcctt cagcaccctg   3120
ctgggctgct atcgcctgtg cccagccaca aacaatgcca tcgagaccgt gtccatcaac   3180
aataacggcg ccgccatgtt ctctagccac acgagccccc ggggctctat cagcaaggag  3240
tgtaacctgg tgtacctgat ccctcacgcc gtgggctcct ctgaggacct gaagaaggag  3300
gaggcagcag gaatcgcaag gcccctggag aagctgtccc ctgccctgtc tgtgatcctg  3360
gactacgata ccgacgtgag cctggagaag atccagccaa tcacacagaa cggccagcac  3420
ccaacctacc cctatgatgt gcccgactat gcctgactct agaataatca acctctggat  3480
tacaaaattt gtgaaagatt gactggtatt cttaactatg ttgctccttt tacgctatgt   3540
ggatacgctg cttttaatgcc tttgtatcat gctattgctt cccgtatggc tttcattttc  3600
tcctccttgt ataaatcctg gttgctgtct ctttatgagg agttgtggcc cgttgtcagg  3660
caacgtggcg tggtgtgcac tgtgtttgct gacgcaaccc ccactggttg gggcattgcc  3720
accacctgtc agctccttc cgggactttc gctttccccc tccctattgc cacggcggaa   3780
ctcatcgccg cctgccttgc ccgctgctgg acaggggctc ggctgttggg cactgacaat  3840
tccgtggtgt tgtcggggaa atcatcgtcc tttccttggc tgctcgcctg tgttgccacc   3900
tggattctgc gcgggacgtc cttctgctac gtcccttcgg ccctcaatcc agcggaccctt  3960 ccttcccgcg gcctgctgcc ggctctgcgg cctcttccgc gtcttcgcct tcgccctcag  4020
acgagtcgga tctcccttttg ggccgcctcc ccgcctaagc ttatcgatac cgtcgagatc  4080
taacttgttt attgcagctt ataatggtta caaataaagc aatagcatca caaatttcac  4140
aaataaagca ttttttttcac tgcattctag ttgtggtttg tccaaactca tcaatgtatc  4200
```

| | | |
|---|---|---|
| ttatcatgtc tggatctcga cctcgactag agcatggcta cgtagataag tagcatggcg | 4260 | |
| ggttaatcat taactacaag gaaccccctag tgatggagtt ggccactccc tctctgcgcg | 4320 | |
| ctcgctcgct cactgaggcc gggcgaccaa aggtcgcccg acgcccgggc tttgcccggg | 4380 | |
| cggcctcagt gagcgagcga gcgcgc | 4406 | |

```
<210> SEQ ID NO 7
<211> LENGTH: 1161
<212> TYPE: DNA
<213> ORGANISM: Artificial Sequence
<220> FEATURE:
<223> OTHER INFORMATION: Synthetic polynucleotide

<400> SEQUENCE: 7
```

| | |
|---|---|
| atggacaagc tggatgccaa tgtgagctcc gaggagggct tcggctccgt ggagaaggtg | 60 |
| gtgctgctga catttctgtc taccgtgatc ctgatggcca tcctgggcaa tctgctggtc | 120 |
| atggtggccg tgtgctggga caggcagctg cgcaagatca agacaaacta cttcatcgtg | 180 |
| tctctggcct tgccgatct gctggtgagc gtgctggtca tgcctttcgg cgccatcgag | 240 |
| ctggtgcagg acatctggat ctatggcgag gtgttttgcc tggtgcggac cagcctggat | 300 |
| gtgctgctga ccacagccag catcttccac ctgtgctgta tctccctgga ccgctactat | 360 |
| gccatctgct gtcagcctct ggtgtaccgg aataagatga ccactgag atcgccctg | 420 |
| atgctgggag gatgttgggt catccctacc ttcatctctt ttctgccaat catgcagggc | 480 |
| tggaacaata tcggcatcat cgatctgatc gagaagagga gttcaacca gaattccaac | 540 |
| tctacatact gcgtgttcat ggtgaacaag ccctatgcca tcacctgcag cgtggtggcc | 600 |
| ttctacatcc cttttctgct gatggtgctg ctatctactatc ggatctatgt gacagccaag | 660 |
| gagcacgccc accagatcca gatgctgcag agggcaggag cctctagcga gagcaggcca | 720 |
| cagagcgccg accagcactc cacacacagg atgagaacag agaccaaggc cgccaagacc | 780 |
| ctgtgcatca tcatgggctg cttctgtctg tgctgggccc ccttctttgt gaccaatatc | 840 |
| gtggaccct tcatcgatta cacagtgcct ggccaagtgt ggaccgcctt tctgtggctg | 900 |
| ggctacatca atagcggcct gaaccccttc ctgtatgcct ttctgaacaa gtccttcagg | 960 |
| agagcctttc tgatcatcct gtgctgtgac gatgagaggt acaggaggcc ctctatcctg | 1020 |
| ggccagaccg tgcccgttc caccacaacc atcaatggct ctacacacgt gctgaggtat | 1080 |
| accgtgctgc acagaggcca ccaccaggag ctggagaagc tgccaatcca caacgatccc | 1140 |
| gagagcctgg agtcctgctt t | 1161 |

```
<210> SEQ ID NO 8
<211> LENGTH: 4229
<212> TYPE: DNA
<213> ORGANISM: Artificial Sequence
<220> FEATURE:
<223> OTHER INFORMATION: 5HTR4 expression cassette sequence

<400> SEQUENCE: 8
```

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctacgta gccatgctct | 180 |
| aggacattga ttattgacta gtggagtcc gcgttacata acttacgta aatggcccgc | 240 |
| ctggctgacc gcccaacgac ccccgcccat tgacgtcaat aatgacgtat gttcccatag | 300 |

-continued

```
taacgccaat agggactttc cattgacgtc aatgggtgga gtatttacgg taaactgccc    360
acttggcagt acatcaagtg tatcatatgc caagtacgcc ccctattgac gtcaatgacg    420
gtaaatggcc cgcctggcat tatgcccagt acatgacctt atgggacttt cctacttggc    480
agtacatcta cgtattagtc atcgctatta ccatggtcga ggtgagcccc acgttctgct    540
tcactctccc catctccccc cctccccac ccccaatttt gtatttattt atttttaat     600
tattttgtgc agcgatgggg gcggggggg ggggggcgc gcgccaggcg gggcggggcg     660
gggcgagggg cggggcgggg cgaggcggag aggtgcggcg gcagccaatc agagcggcgc    720
gctccgaaag tttccttta tggcgaggcg gcggcggcgg cggccctata aaaagcgaag     780
cgcgcggcg gcgggagtcg ctgcgcgctg ccttcgcccc gtccccgct ccgccgccgc     840
ctcgcgccgc ccgccccggc tctgactgac cgcgttacta aaacaggtaa gtccggcctc    900
cgcgccgggt tttggcgcct cccgcgggcg ccccctcct cacggcgagc gctgccacgt    960
cagacgaagg gcgcagcgag cgtcctgatc cttcgcccg gacgctcagg acagcggccc    1020
gctgctcata agactcggcc ttagaacccc agtatcagca aaggacatt ttaggacggg    1080
acttgggtga ctctagggca ctggttttct ttccagagag cggaacaggc gaggaaaagt    1140
agtcccttct cggcgattct gcggagggat ctccgtgggg cggtaacgc cgatgatgcc    1200
tctactaacc atgttcatgt tttctttttt tttctacagg tcctgggtga cgaacagggt    1260
accgccacca tggtgtccaa gggagaggag ctgttcaccg gagtggtgcc catcctggtg    1320
gagctggacg gcgatgtgaa tggccacaag tttagcgtgt ccggagaggg agagggcgac    1380
gcaacctacg gcaagctgac actgaagttc atctgcacca caggcaagct gcccgtgcct    1440
tggccaaccc tggtgaccac actgacatac ggcgtgcagt gttttctcg gtatccagac    1500
cacatgaagc agcacgattt ctttaagagc gccatgcccg agggctacgt gcaggagagg    1560
acaatcttct ttaaggacga tggcaactat aagaccagag ccgaggtgaa gttcgagggc    1620
gacacactg tgaaccggat cgagctgaag ggcatcgact ttaaggagga tggcaatatc    1680
ctgggccaca agctggagta caactataat tcccacaacg tgtacatcat ggccgataag    1740
cagaagaacg gcatcaaggt gaacttcaag atccgccaca atatcgagga cggctctgtg    1800
cagctggccg atcactacca gcagaacacc cctatcggcg acggacccgt gctgctgcct    1860
gataatcact atctgtctac acagagcgcc ctgtccaagg acccaaacga gaagagggat    1920
cacatggtgc tgctggagtt cgtgaccgca gcaggcatca cactgggcat ggatgagctg    1980
tataagcgaa aaagaagatc aggttcgggt gcgccagtaa agcagacatt aaactttgat    2040
ttgctgaaac ttgcaggtga tgtagagtca atccaggtc caggatccat ggacaagctg    2100
gatgccaatg tgagctccga ggagggcttc ggctccgtgg agaaggtggt gctgctgaca    2160
tttctgtcta ccgtgatcct gatggccatc ctgggcaatc tgctggtcat ggtggccgtg    2220
tgctgggaca gcagctgcg caagatcaag acaaactact catcgtgtc tctggccttt    2280
gccgatctgc tggtgagcgt gctggtcatg ccttcggcg ccatcgagct ggtgcaggac    2340
atctggatct atggcgaggt gttttgcctg gtgcggacca gcctggatgt gctgctgacc    2400
acagccagca tcttccacct gtgctgtatc tccctggacc gctactatgc catctgctgt    2460
cagcctctgg tgtaccggaa taagatgaca ccactgagga tcgccctgat gctgggagga    2520
tgttgggtca tccctacctt catctctttt ctgccaatca tgcagggctg gaacaatatc    2580
ggcatcatcg atctgatcga aagaggaag ttcaaccaga attccaactc tacatactgc    2640
gtgttcatgg tgaacaagcc ctatgccatc acctgcagcg tggtggcctt ctacatccct    2700
```

```
tttctgctga tggtgctggc ctactatcgg atctatgtga cagccaagga gcacgcccac    2760
cagatccaga tgctgcagag ggcaggagcc tctagcgaga gcaggccaca gagcgccgac    2820
cagcactcca cacacaggat gagaacagag accaaggccg ccaagaccct gtgcatcatc    2880
atgggctgct ctgtctgtg ctgggccccc ttctttgtga ccaatatcgt ggacccccttc   2940 atcgattaca cagtgcctgg ccaagtgtgg accgcctttc tgtggctggg ctacatcaat    3000
agcggcctga accccttcct gtatgccttt ctgaacaagt ccttcaggag agcctttctg    3060
atcatcctgt gctgtgacga tgagaggtac aggaggccct ctatcctggg ccagaccgtg    3120
ccctgttcca ccacaaccat caatggctct acacacgtgc tgaggtatac cgtgctgcac    3180
agaggccacc accaggagct ggagaagctg ccaatcccaca acgatcccga gagcctggag    3240
tcctgctttt accccatga cgtgcctgat tatgcctgac tctagaataa tcaacctctg    3300
gattacaaaa tttgtgaaag attgactggt attcttaact atgttgctcc ttttacgcta    3360
tgtggatacg ctgctttaat gcctttgtat catgctattg cttcccgtat ggctttcatt    3420
ttctcctcct tgtataaatc ctggttgctg tctctttatg aggagttgtg gcccgttgtc    3480
aggcaacgtg gcgtggtgtg cactgtgttt gctgacgcaa cccccactgg ttggggcatt    3540
gccaccacct gtcagctcct ttccgggact ttcgctttcc ccctccctat tgccacggcg    3600
gaactcatcg ccgcctgcct tgcccgctgc tggacagggg ctcggctgtt gggcactgac    3660
aattccgtgg tgttgtcggg gaaatcatcg tcctttcctt ggctgctcgc ctgtgttgcc    3720
acctggattc tgcgcgggac gtccttctgc tacgtcccctt cggccctcaa tccagcggac    3780
cttccttccc gcggcctgct gccggctctg cggcctcttc cgcgtcttcg ccttcgccct    3840
cagacgagtc ggatctccct ttgggccgcc tccccgccta gcttatcga taccgtcgag    3900 atctaacttg tttattgcag cttataatgg ttacaaataa agcaatagca tcacaaattt    3960
cacaaataaa gcattttttt cactgcattc tagttgtggt ttgtccaaac tcatcaatgt    4020
atcttatcat gtctggatct cgacctcgac tagagcatgg ctacgtagat aagtagcatg    4080
gcgggttaat cattaactac aaggaacccc tagtgatgga gttggccact ccctctctgc    4140
gcgctcgctc gctcactgag gccgggcgac caaaggtcgc ccgacgcccg gctttgccc    4200 gggcggcctc agtgagcgag cgagcgcgc                                     4229
```

<210> SEQ ID NO 9
<211> LENGTH: 1059
<212> TYPE: DNA
<213> ORGANISM: Artificial Sequence
<220> FEATURE:
<223> OTHER INFORMATION: Synthetic polynucleotide

<400> SEQUENCE: 9

```
atggagcaca cccacgcaca cctggcagca aacagctccc tgtcctggtg gtctcctggc      60
agcgcctgcg gactgggctt cgtgccagtg gtgtactata gctgctgct gtgcctggga     120 ctgccagcaa acatcctgac agtgatcatc ctgtcccagc tggtggccag agacagaag     180 tctagctaca attatctgct ggccctggca gcagcagaca tcctggtgct gttctttatc    240
gtgttcgtgg actttctgct ggaggattc atcctgaaca tgcagatgcc acaggtgccc     300
gacaagatca tcgaggtgct ggagttttcc tctatccaca cctccatctg gatcaccgtg     360
cctctgacaa tcgataggta catcgccgtg tgccacccac tgaagtacca caccgtgtct    420
tatcccgcca ggacaagaaa agtgatcgtg agcgtgtaca tcacctgttt cctgacatct    480
```

| | |
|---|---|
| atcccctact attggtggcc taatatctgg accgaggatt acatctctac aagcgtgcac | 540 |
| cacgtgctga tctggattca ctgcttcaca gtgtatctgg tgccatgtag catcttcttt | 600 |
| atcctgaact ccatcatcgt gtacaagctg cggcgcaagt ctaattttcg gctgcgcggc | 660 |
| tatagcaccg gcaagaccac agccatcctg ttcaccatca catccatctt tgccacactg | 720 |
| tgggccccac ggatcatcat gatcctgtac cacctgtatg gagcaccaat ccagaacagg | 780 |
| tggctggtgc acatcatgtc tgacatcgcc aatatgctgg ccctgctgaa caccgccatc | 840 |
| aatttctttc tgtactgctt catcagcaag aggtttagaa ccatggccgc cgccacactg | 900 |
| aaggccttct ttaagtgtca gaagcagcct gtgcagttct acaccaacca caattttttcc | 960 |
| atcacaagct ccccttggat ctccccagcc aactctcact gcatcaagat gctggtgtac | 1020 |
| cagtatgata agaatggcaa gcccatcaag gtgagcccc | 1059 |

<210> SEQ ID NO 10
<211> LENGTH: 4127
<212> TYPE: DNA
<213> ORGANISM: Artificial Sequence
<220> FEATURE:
<223> OTHER INFORMATION: GPR139 expression cassette

<400> SEQUENCE: 10

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctacgta gccatgctct | 180 |
| aggacattga ttattgacta gtggagttcc gcgttacata acttacggta aatggcccgc | 240 |
| ctggctgacc gcccaacgac ccccgcccat tgacgtcaat aatgacgtat gttcccatag | 300 |
| taacgccaat agggactttc cattgacgtc aatgggtgga gtatttacgg taaactgccc | 360 |
| acttggcagt acatcaagtg tatcatatgc caagtacgcc ccctattgac gtcaatgacg | 420 |
| gtaaatggcc cgcctggcat tatgcccagt acatgacctt atgggacttt cctacttggc | 480 |
| agtacatcta cgtattagtc atcgctatta ccatggtcga ggtgagcccc acgttctgct | 540 |
| tcactctccc catctccccc ccctccccac cccaatttt gtatttattt attttttaat | 600 |
| tattttgtgc agcgatgggg gcggggggg ggggggcgc gcgccaggcg ggcggggcg | 660 |
| gggcgagggg cggggcgggg cgaggcgag aggtgcggcg gcagccaatc agagcggcgc | 720 |
| gctccgaaag tttcctttta tggcgaggcg gcggcggcgg cggccctata aaaagcgaag | 780 |
| cgcgcggcgg gcgggagtcg ctgcgcgctg ccttcgcccc gtgccccgct ccgccgccgc | 840 |
| ctcgcgccgc ccgccccggc tctgactgac cgcgttacta aaacaggtaa gtccggcctc | 900 |
| cgcgccgggt tttggcgcct cccgcgggcg ccccctcct cacggcgagc gctgccacgt | 960 |
| cagacgaagg gcgcagcgag cgtcctgatc cttccgcccg gacgctcagg acagcggccc | 1020 |
| gctgctcata agactcggcc ttagaacccc agtatcagca gaaggacatt ttaggacggg | 1080 |
| acttgggtga ctctagggca ctggttttct ttccagagag cggaacaggc gaggaaaagt | 1140 |
| agtcccttct cggcgattct gcggagggat ctccgtgggg cggtgaacgc cgatgatgcc | 1200 |
| tctactaacc atgttcatgt tttctttttt tttctacagg tcctgggtga cgaacagggt | 1260 |
| accgccacca tggtgtccaa gggagaggag ctgttcaccg gagtggtgcc catcctggtg | 1320 |
| gagctggacg gcgatgtgaa tggccacaag tttagcgtgt ccggagaggg agagggcgac | 1380 |
| gcaacctacg gcaagctgac actgaagttc atctgcacca caggcaagct gcccgtgcct | 1440 |
| tggccaaccc tggtgaccac actgacatac ggcgtgcagt gttttctcg gtatccagac | 1500 |

```
cacatgaagc agcacgattt ctttaagagc gccatgcccg agggctacgt gcaggagagg    1560
acaatcttct ttaaggacga tggcaactat aagaccagag ccgaggtgaa gttcgagggc    1620
gacacactgg tgaaccggat cgagctgaag ggcatcgact ttaaggagga tggcaatatc    1680
ctgggccaca agctggagta caactataat tcccacaacg tgtacatcat ggccgataag    1740
cagaagaacg gcatcaaggt gaacttcaag atccgccaca atatcgagga cggctctgtg    1800
cagctggccg atcactacca gcagaacacc cctatcggcg acggacccgt gctgctgcct    1860
gataatcact atctgtctac acagagcgcc ctgtccaagg acccaaacga agagggat     1920 cacatggtgc tgctggagtt cgtgaccgca gcaggcatca cactgggcat ggatgagctg    1980
tataagcgaa aagaagatc aggttcgggt gcgccagtaa agcagacatt aaactttgat    2040
ttgctgaaac ttgcaggtga tgtagagtca aatccaggtc caggatccat ggagcacacc    2100
cacgcacacc tggcagcaaa cagctccctg tcctggtggt ctcctggcag cgcctgcgga    2160
ctgggcttcg tgccagtggt gtactatagc ctgctgctgt gcctgggact gccagcaaac    2220
atcctgacag tgatcatcct gtcccagctg gtggccagga gacagaagtc tagctacaat    2280
tatctgctgg ccctggcagc agcagacatc ctggtgctgt tctttatcgt gttcgtggac    2340
tttctgctgg aggatttcat cctgaacatg cagatgccac aggtgcccga caagatcatc    2400
gaggtgctga gttttcctc tatccacacc tccatctgga tcaccgtgcc tctgacaatc    2460
gataggtaca tcgccgtgtg ccaccactg aagtaccaca ccgtgtctta tccgccagg    2520 acaagaaaag tgatcgtgag cgtgtacatc acctgtttcc tgacatctat cccctactat    2580
tggtggccta atatctggac cgaggattac atctctacaa gcgtgcacca cgtgctgatc    2640
tggattcact gcttcacagt gtatctggtg ccatgtagca tcttctttat cctgaactcc    2700
atcatcgtgt acaagctgcg cgcaagtct aattttcggc tgcgcggcta tagcaccggc    2760
aagaccacag ccatcctgtt caccatcaca tccatctttg ccacactgtg gcccccacgg    2820
atcatcatga tcctgtacca cctgtatgga gcaccaatcc agaacaggtg gctggtgcac    2880
atcatgtctg acatcgccaa tatgctggcc ctgctgaaca ccgccatcaa tttctttctg    2940
tactgcttca tcagcaagag gtttagaacc atggccgccg ccacactgaa ggccttcttt    3000
aagtgtcaga agcagcctgt gcagttctac accaaccaca attttttccat cacaagctcc    3060 ccttggatct ccccagccaa ctctcactgc atcaagatgc tggtgtacca gtatgataag    3120
aatggcaagc ccatcaaggt gagcccctac ccttatgacg tgcctgatta cgcctgaatc    3180
tagaataatc aacctctgga ttacaaaatt tgtgaaagat tgactggtat tcttaactat    3240
gttgctcctt ttacgctatg tggatacgct gctttaatgc ctttgtatca tgctattgct    3300
tcccgtatgg ctttcattt ctcctccttg tataaatcct ggttgctgtc tctttatgag    3360
gagttgtggc ccgttgtcag gcaacgtggc gtggtgtgca ctgtgtttgc tgacgcaacc    3420
cccactggtt ggggcattgc caccacctgt cagctccttt ccgggacttt cgctttcccc    3480
ctccctattg ccacggcgga actcatcgcc gcctgccttg cccgctgctg acagggggct    3540
cggctgttgg gcactgacaa ttccgtggtg ttgtcgggga atcatcgtc ctttccttgg    3600 ctgctcgcct gtgttgccac ctggattctg cgcgggacgt ccttctgcta cgtcccttcg    3660
gccctcaatc cagcggacct tccttcccgc ggcctgctgc cggctctgcg gcctcttccg    3720
cgtcttcgcc ttcgccctca gacgagtcgg atctcccttt gggccgcctc cccgcctaag    3780
cttatcgata ccgtcgagat ctaacttgtt tattgcagct tataatggtt acaaataaag    3840
```

```
caatagcatc acaaatttca caaataaagc attttttttca ctgcattcta gttgtggttt      3900
gtccaaactc atcaatgtat cttatcatgt ctggatctcg acctcgacta gagcatggct      3960
acgtagataa gtagcatggc gggttaatca ttaactacaa ggaacccta gtgatggagt       4020 tggccactcc ctctctgcgc gctcgctcgc tcactgaggc cgggcgacca aaggtcgccc      4080
gacgcccggg ctttgcccgg cggcctcag tgagcgagcg agcgcgc                     4127
```

<210> SEQ ID NO 11
<211> LENGTH: 135
<212> TYPE: DNA
<213> ORGANISM: Artificial Sequence
<220> FEATURE:
<223> OTHER INFORMATION: SV40 polyadenylation sequence

<400> SEQUENCE: 11

```
aacttgttta ttgcagctta taatggttac aaataaagca atagcatcac aaatttcaca       60
aataaagcat ttttttcact gcattctagt tgtggtttgt ccaaactcat caatgtatct      120
tatcatgtct ggatc                                                       135
```

<210> SEQ ID NO 12
<211> LENGTH: 8048
<212> TYPE: DNA
<213> ORGANISM: Artificial Sequence
<220> FEATURE:
<223> OTHER INFORMATION: DRD1 expression plasmid

<400> SEQUENCE: 12

```
cagcagctgc gcgctcgctc gctcactgag gccgcccggg caaagcccgg gcgtcgggcg       60
acctttggtc gcccggcctc agtgagcgag cgagcgcgca gagagggagt ggccaactcc      120
atcactaggg gttccttgta gttaatgatt aacccgccat gctacttatc tacgtagcca      180
tgctctagga cattgattat tgactagtgg agttccgcgt tacataactt acggtaaatg      240
gcccgcctgg ctgaccgccc aacgaccccc gcccattgac gtcaataatg acgtatgttc      300
ccatagtaac gccaataggg actttccatt gacgtcaatg ggtggagtat ttacggtaaa      360
ctgcccactt ggcagtacat caagtgtatc atatgccaag tacgccccct attgacgtca      420
atgacggtaa atggcccgcc tggcattatg cccagtacat gaccttatgg actttccta      480 cttggcagta catctacgta ttagtcatcg ctattaccat ggtcgaggtg agccccacgt      540
tctgcttcac tctccccatc tccccccct cccacccc aattttgtat ttatttattt        600
tttaattatt ttgtgcagcg atggggcgg gggggggg gggcgcgcgc caggcggggc         660 ggggcgggc gagggcggg gcggggcgag gcggagaggt gcggcggcag ccaatcagag        720
cggcgcgctc cgaaagtttc cttttatggc gaggcggcgg cggcggcggc cctataaaaa      780
gcgaagcgcg cggcgggcgg gagtcgctgc gcgctgcctt cgccccgtgc cccgctccgc      840
cgccgcctcg cgccgcccgc cccggctctg actgaccgcg ttactaaaac aggtaagtcc      900
ggcctccgcg ccgggttttg gcgcctcccg cgggcgcccc cctcctcacg gcgagcgctg      960
ccacgtcaga cgaagggcgc agcgagcgtc ctgatccttc cgcccggacg ctcaggacag     1020
cggcccgctg ctcataagac tcggccttag aaccccagta tcagcagaag gacattttag     1080
gacgggactt gggtgactct agggcactgg ttttctttcc agagagcgga acaggcgagg     1140
aaaagtagtc ccttctcggc gattctgcgg agggatctcc gtgggcggt gaacgccgat      1200 gatgcctcta ctaaccatgt tcatgttttc tttttttttc tacaggtcct gggtgacgaa     1260
cagggtaccg ccaccatggt gtccaaggga gaggagctgt tcaccggagt ggtgcccatc     1320
```

```
ctggtggagc tggacggcga tgtgaatggc cacaagttta gcgtgtccgg agagggagag    1380
ggcgacgcaa cctacggcaa gctgacactg aagttcatct gcaccacagg caagctgccc    1440
gtgccttggc caaccctggt gaccacactg acatacggcg tgcagtgttt ttctcggtat    1500
ccagaccaca tgaagcagca cgatttcttt aagagcgcca tgcccgaggg ctacgtgcag    1560
gagaggacaa tcttctttaa ggacgatggc aactataaga ccagagccga ggtgaagttc    1620
gagggcgaca cactggtgaa ccggatcgag ctgaagggca tcgactttaa ggaggatggc    1680
aatatcctgg ccacaagct ggagtacaac tataattccc acaacgtgta catcatggcc    1740
gataagcaga agaacggcat caaggtgaac ttcaagatcc gccacaatat cgaggacggc    1800
tctgtgcagc tggccgatca ctaccagcag aacacccta tcggcgacgg acccgtgctg    1860
ctgcctgata tcactatct gtctacacag agcgccctgt ccaaggaccc aaacgagaag    1920
agggatcaca tggtgctgct ggagttcgtg accgcagcag gcatcacact gggcatggat    1980
gagctgtata gcgaaaaag aagatcaggt tcgggtgcgc cagtaaagca gacattaaac    2040
tttgatttgc tgaaacttgc aggtgatgta gagtcaaatc caggtccagg atccatgagg    2100
acactgaata cctctgccat ggatggcaca ggcctggtgg tggagaggga ctttagcgtg    2160
agaatcctga ccgcctgctt cctgagcctg ctgatcctgt ccacactgct gggcaatacc    2220
ctggtgtgcg ccgccgtgat ccggtttcgc cacctgagat ccaaggtgac aaacttcttt    2280
gtgatcagcc tggccgtgtc cgatctgctg gtggccgtgc tggtcatgcc ttggaaggca    2340
gtggcagaga tcgcaggatt ctggccattt ggctctttct gcaatatctg ggtggccttc    2400
gatatcatgt gctccaccgc ctctatcctg aacctgtgcg tgatcagcgt ggaccggtac    2460
tgggccatca gctccccctt caggtacgag agaaagatga cacccaaggc cgccttcatc    2520
ctgatcagcg tggcctggac cctgtctgtg ctgatcagct ttatccccgt gcagctgtcc    2580
tggcacaagg ccaagcccac aagcccttcc gacggcaatg ccacatctct ggccgagacc    2640
atcgataact gtgactctag cctgagccgc acctacgcca tctcctctag cgtgatctcc    2700
ttctatatcc ctgtggccat catgatcgtg acatacaccc ggatctatcg catcgcccag    2760
aagcagatca ggagaatcgc cgccctggag agggcagcag tgcacgccaa gaattgccag    2820
accacaaccg gcaacggcaa gcctgtggag tgttctcagc cagagtcctc tttcaagatg    2880
agctttaaga gagagacaaa ggtgctgaag accctgtccg tgatcatggg cgtgttcgtg    2940
tgctgttggc tgcctttctt tatcctgaat tgcatcctgc cattttgtgg ctccggcgag    3000
acacagccct ctgcatcga ttctaacacc tttgacgtgt tcgtgtggtt tggctgggcc    3060
aatagctccc tgaaccctat catctacgcc ttcaatgccg attttcggaa ggccttcagc    3120
accctgctgg gctgctatcg cctgtgccca gccacaaaca atgccatcga ccgtgtcc    3180
atcaacaata cggcgccgc catgttctct agccaccacg agccccgggg ctctatcagc    3240
aaggagtgta acctggtgta cctgatccct cacgccgtgg gctcctctga ggacctgaag    3300
aaggaggagg cagcaggaat cgcaaggccc ctggagaagc tgtcccctgc cctgtctgtg    3360
atcctggact acgataccga cgtgagcctg gagaagatcc agccaatcac acagaacggc    3420
cagcacccaa cctaccccta tgatgtgccc gactatgcct gactctagaa taatcaacct    3480
ctggattaca aaatttgtga agattgact ggtattctta actatgttgc tccttttacg    3540
ctatgtggat acgctgcttt aatgcctttg tatcatgcta ttgcttcccg tatggctttc    3600
attttctcct ccttgtataa atcctggttg ctgtctcttt atgaggagtt gtggcccgtt    3660
```

-continued

```
gtcaggcaac gtggcgtggt gtgcactgtg tttgctgacg caaccccac tggttggggc      3720 attgccacca cctgtcagct cctttccggg actttcgctt cccctccc tattgccacg       3780 gcggaactca tcgccgcctg ccttgcccgc tgctggacag gggctcggct gttgggcact     3840
gacaattccg tggtgttgtc ggggaaatca tcgtcctttc cttggctgct cgcctgtgtt     3900
gccacctgga ttctgcgcgg gacgtccttc tgctacgtcc cttcggccct caatccagcg     3960
gaccttcctt cccgcggcct gctgccggct ctgcggcctc ttccgcgtct tcgccttcgc     4020
cctcagacga gtcggatctc cctttgggcc gcctccccgc ctaagcttat cgataccgtc     4080
gagatctaac ttgtttattg cagcttataa tggttacaaa taaagcaata gcatcacaaa     4140
tttcacaaat aaagcatttt tttcactgca ttctagttgt ggtttgtcca aactcatcaa     4200
tgtatcttat catgtctgga tctcgacctc gactagagca tggctacgta gataagtagc     4260
atggcgggtt aatcattaac tacaaggaac ccctagtgat ggagttggcc actccctctc     4320
tgcgcgctcg ctcgctcact gaggccgggc gaccaaaggt cgcccgacgc ccgggctttg     4380
cccgggcggc ctcagtgagc gagcgagcgc gcagctggc gtaatagcga agaggcccgc      4440
accgatcgcc cttcccaaca gttgcgcagc ctgaatggcg aatggaattc cagacgattg     4500
agcgtcaaaa tgtaggtatt tccatgagcg ttttcctgt tgcaatggct ggcggtaata      4560
ttgttctgga tattaccagc aaggccgata gtttgagttc ttctactcag gcaagtgatg     4620
ttattactaa tcaagaagt attgcgacaa cggttaattt gcgtgatgga cagactcttt      4680
tactcggtgg cctcactgat tataaaaaca cttctcagga ttctggcgta ccgttcctgt     4740
ctaaaatccc tttaatcggc ctcctgttta gctcccgctc tgattctaac gaggaaagca     4800
cgttatacgt gctcgtcaaa gcaaccatag tacgcgccct gtagcggcgc attaagcgcg     4860
gcgggtgtgg tggttacgcg cagcgtgacc gctacacttg ccagcgccct agcgcccgct     4920
cctttcgctt tcttcccttc ctttctcgcc acgttcgccg gctttccccg tcaagctcta     4980 aatcggggc tccctttagg gttccgattt agtgctttac ggcacctcga ccccaaaaaa     5040
cttgattagg gtgatggttc acgtagtggg ccatcgccct gatagacggt ttttcgccct     5100
ttgacgttag agtccacgtt ctttaatagt ggactcttgt tccaaactgg aacaacactc     5160
aaccctatct cggtctattc ttttgattta agggatttt gccgatttc ggcctattgg       5220 ttaaaaaatg agctgattta acaaaaattt aacgcgaatt ttaacaaaat attaacgttt     5280
acaatttaaa tatttgctta tacaatcttc ctgttttgg ggcttttctg attatcaacc      5340
ggggtacata tgattgacat gctagtttta cgattaccgt tcatcgattc tcttgtttgc     5400
tccagactct caggcaatga cctgatagcc tttgtagaga cctctcaaaa atagctaccc     5460
tctccggcat gaatttatca gctagaacgg ttgaatatca tattgatggt gatttgactg     5520
tctccggcct ttctcacccg tttgaatctt tacctacaca ttactcaggc attgcattta     5580
aaatatatga gggttctaaa aattttatc cttgcgttga aataaaggct tctcccgcaa     5640
aagtattaca gggtcataat gttttggta caaccgattt agctttatgc tctgaggctt      5700
tattgcttaa ttttgctaat tctttgcctt gcctgtatga tttattggat gttggaattc     5760
ctgatgcggt attttctcct tacgcatctg tgcggtattt cacaccgcat atggtgcact     5820
ctcagtacaa tctgctctga tgccgcatag ttaagccagc ccgacaccc gccaacaccc      5880 gctgacgcgc cctgacgggc ttgtctgctc ccggcatccg cttacagaca agctgtgacc     5940
gtctccggga gctgcatgtg tcagaggttt tcaccgtcat caccgaaacg cgcgagacga     6000
aagggcctcg tgatacgcct atttttatag gttaatgtca tgataataat ggtttcttag     6060
```

```
acgtcaggtg gcacttttcg gggaaatgtg cgcggaaccc ctatttgttt attttttctaa    6120
atacattcaa atatgtatcc gctcatgaga caataaccct gataaatgct tcaataatat    6180
tgaaaaagga agagtatgag tattcaacat ttccgtgtcg cccttattcc ctttttttgcg   6240
gcatttttgcc ttcctgtttt tgctcaccca gaaacgctgg tgaaagtaaa agatgctgaa   6300
gatcagttgg gtgcacgagt gggttacatc gaactggatc tcaacagcgg taagatcctt   6360
gagagttttc gccccgaaga acgttttcca atgatgagca cttttaaagt tctgctatgt   6420
ggcgcggtat tatcccgtat tgacgccggg caagagcaac tcggtcgccg catacactat   6480
tctcagaatg acttggttga gtactcacca gtcacagaaa agcatcttac ggatggcatg   6540
acagtaagag aattatgcag tgctgccata accatgagtg ataacactgc ggccaactta   6600
cttctgacaa cgatcggagg accgaaggag ctaaccgctt ttttgcacaa catgggggat   6660
catgtaactc gccttgatcg ttgggaaccg gagctgaatg aagccatacc aaacgacgag   6720
cgtgacacca cgatgcctgt agcaatggca acaacgttgc gcaaactatt aactggcgaa   6780
ctacttactc tagcttcccg gcaacaatta atagactgga tggaggcgga taaagttgca   6840
ggaccacttc tgcgctcggc ccttccggct ggctggttta ttgctgataa atctggagcc   6900
ggtgagcgtg ggtctcgcgg tatcattgca gcactggggc cagatggtaa gccctcccgt   6960
atcgtagtta tctacacgac ggggagtcag gcaactatgg atgaacgaaa tagacagatc   7020
gctgagatag gtgcctcact gattaagcat tggtaactgt cagaccaagt ttactcatat   7080
atactttaga ttgatttaaa acttcatttt taatttaaaa ggatctaggt gaagatcctt   7140
tttgataatc tcatgaccaa aatcccttaa cgtgagtttt cgttccactg agcgtcagac   7200
cccgtagaaa agatcaaagg atcttcttga gatcctttt ttctgcgcgt aatctgctgc    7260
ttgcaaacaa aaaaaccacc gctaccagcg gtggtttgtt tgccggatca agagctacca   7320
actcttttc cgaaggtaac tggcttcagc agagcgcaga taccaaatac tgtccttcta    7380
gtgtagccgt agttaggcca ccacttcaag aactctgtag caccgcctac atacctcgct   7440
ctgctaatcc tgttaccagt ggctgctgcc agtggcgata agtcgtgtct taccgggttg   7500
gactcaagac gatagttacc ggataaggcg cagcggtcgg gctgaacggg gggttcgtgc   7560
acacagccca gcttggagcg aacgacctac accgaactga gatacctaca gcgtgagcta   7620
tgagaaagcg ccacgcttcc cgaagggaga aaggcggaca ggtatccggt aagcggcagg   7680
gtcggaacag gagagcgcac gagggagctt ccagggggaa acgcctggta tctttatagt   7740
cctgtcgggt ttcgccacct ctgacttgag cgtcgatttt tgtgatgctc gtcaggggg    7800
cggagcctat ggaaaaacgc cagcaacgcg gccttttac ggttcctggc cttttgctgg    7860
ccttttgctc acatgttctt tcctgcgtta tcccctgatt ctgtggataa ccgtattacc   7920
gcctttgagt gagctgatac cgctcgccgc agccgaacga ccgagcgcag cgagtcagtg   7980
agcgaggaag cggaagagcg cccaatacgc aaaccgcctc tccccgcgcg ttggccgatt   8040
cattaatg                                                            8048
```

<210> SEQ ID NO 13
<211> LENGTH: 7871
<212> TYPE: DNA
<213> ORGANISM: Artificial Sequence
<220> FEATURE:
<223> OTHER INFORMATION: 5HRT4 expression plasmid

<400> SEQUENCE: 13

```
cagcagctgc gcgctcgctc gctcactgag gccgcccggg caaagcccgg gcgtcgggcg      60
acctttggtc gcccggcctc agtgagcgag cgagcgcgca gagagggagt ggccaactcc     120
atcactaggg gttccttgta gttaatgatt aacccgccat gctacttatc tacgtagcca     180
tgctctagga cattgattat tgactagtgg agttccgcgt tacataactt acggtaaatg     240
gcccgcctgg ctgaccgccc aacgaccccc gcccattgac gtcaataatg acgtatgttc     300
ccatagtaac gccaataggg actttccatt gacgtcaatg ggtggagtat ttacggtaaa     360
ctgcccactt ggcagtacat caagtgtatc atatgccaag tacgcccct attgacgtca      420 atgacggtaa atggcccgcc tggcattatg cccagtacat gaccttatgg gactttccta     480
cttggcagta catctacgta ttagtcatcg ctattaccat ggtcgaggtg agccccacgt     540
tctgcttcac tctccccatc tcccccccct ccccacccc aatttttgtat ttatttattt      600 tttaattatt ttgtgcagcg atggggggcgg ggggggggg gggcgcgcgc caggcggggc     660
ggggcggggc gaggggcggg gcggggcgag gcggagaggt gcggcggcag ccaatcagag     720
cggcgcgctc cgaaagtttc cttttatggc gaggcggcgg cggcggcggc cctataaaaa     780
gcgaagcgcg cggcgggcgg gagtcgctgc gcgctgcctt cgccccgtgc cccgctccgc     840
cgccgcctcg cgccgcccgc cccggctctg actgaccgcg ttactaaaac aggtaagtcc     900
ggcctccgcg ccgggttttg gcgcctcccg cgggcgcccc cctcctcacg gcgagcgctg     960
ccacgtcaga cgaagggcgc agcgagcgtc ctgatccttc cgcccggacg ctcaggacag    1020
cggcccgctg ctcataagac tcggccttag aaccccagta tcagcagaag gacattttag    1080
gacgggactt gggtgactct agggcactgg ttttctttcc agagagcgga acaggcgagg    1140
aaaagtagtc ccttctcggc gattctgcgg agggatctcc gtgggcggt gaacgccgat      1200 gatgcctcta ctaaccatgt tcatgttttc ttttttttc tacaggtcct gggtgacgaa      1260
cagggtaccg ccaccatggt gtccaaggga gaggagctgt tcaccggagt ggtgcccatc    1320
ctggtggagc tggacggcga tgtgaatggc cacaagttta gcgtgtccgg agagggagag    1380
ggcgacgcaa cctacggcaa gctgacactg aagttcatct gcaccacagg caagctgccc    1440
gtgccttggc caaccctggt gaccacactg acatacggcg tgcagtgttt ttctcggtat    1500
ccagaccaca tgaagcagca cgatttcttt aagagcgcca tgcccgaggg ctacgtgcag    1560
gagaggacaa tcttctttaa ggacgatggc aactataaga ccagagccga ggtgaagttc    1620
gagggcgaca cactggtgaa ccggatcgag ctgaagggca tcgactttaa ggaggatggc    1680
aatatcctgg gccacaagct ggagtacaac tataattccc acaacgtgta catcatggcc    1740
gataagcaga agaacggcat caaggtgaac ttcaagatcc gccacaatat cgaggacggc    1800
tctgtgcagc tggccgatca ctaccagcag aacacccta tcggcgacgg acccgtgctg     1860
ctgcctgata atcactatct gtctacacag agcgccctgt ccaaggaccc aaacgagaag    1920
agggatcaca tggtgctgct ggagttcgtg accgcagcag gcatcacact gggcatggat    1980
gagctgtata agcgaaaaag aagatcaggt tcgggtgcgc cagtaaagca gacattaaac    2040
tttgatttgc tgaaacttgc aggtgatgta gagtcaaatc caggtccagg atccatggac    2100
aagctggatg ccaatgtgag ctccgaggag ggcttcggct ccgtggagaa ggtggtgctg    2160
ctgacatttc tgtctaccgt gatcctgatg gccatcctgg caatctgct ggtcatggtg      2220 gccgtgtgct gggacaggca gctgcgcaag atcaagacaa actacttcat cgtgtctctg    2280 gccttt gccg atctgctggt gagcgtgctg gtcatgcctt cggcgccat cgagctggtg     2340 caggacatct ggatctatgg cgaggtgttt tgcctggtgc ggaccagcct ggatgtgctg    2400
```

```
ctgaccacag ccagcatctt ccacctgtgc tgtatctccc tggaccgcta ctatgccatc    2460
tgctgtcagc ctctggtgta ccggaataag atgacaccac tgaggatcgc cctgatgctg    2520
ggaggatgtt gggtcatccc taccttcatc tcttttctgc caatcatgca gggctggaac    2580
aatatcggca tcatcgatct gatcgagaag aggaagttca accagaattc caactctaca    2640
tactgcgtgt tcatggtgaa caagccctat gccatcacct gcagcgtggt ggccttctac    2700
atcccttttc tgctgatggt gctggcctac tatcggatct atgtgacagc caaggagcac    2760
gcccaccaga tccagatgct gcagagggca ggagcctcta gcgagagcag gccacagagc    2820
gccgaccagc actccacaca caggatgaga acagagacca aggccgccaa gaccctgtgc    2880
atcatcatgg gctgcttctg tctgtgctgg gccccttct tgtgaccaa tatcgtggac      2940 cccttcatcg attacacagt gcctggccaa gtgtggaccg cctttctgtg gctgggctac    3000
atcaatagcg gcctgaaccc cttcctgtat gcctttctga caagtcctt caggagagcc     3060 tttctgatca tcctgtgctg tgacgatgag aggtacagga ggccctctat cctgggccag    3120
accgtgccct gttccaccac aaccatcaat ggctctacac acgtgctgag gtataccgtg    3180
ctgcacagag gccaccacca ggagctggag aagctgccaa tccacaacga tcccgagagc    3240
ctggagtcct gcttttaccc ctatgacgtg cctgattatg cctgactcta gaataatcaa    3300
cctctggatt acaaaatttg tgaaagattg actggtattc ttaactatgt tgctcctttt    3360
acgctatgtg gatacgctgc tttaatgcct ttgtatcatg ctattgcttc ccgtatggct    3420
ttcattttct cctccttgta taaatcctgg ttgctgtctc tttatgagga gttgtggccc    3480
gttgtcaggc aacgtggcgt ggtgtgcact gtgtttgctg acgcaacccc cactggttgg    3540
ggcattgcca ccacctgtca gctcctttcc gggactttcg ctttcccct ccctattgcc      3600 acggcggaac tcatcgccgc ctgccttgcc cgctgctgga caggggctcg gctgttgggc    3660
actgacaatt ccgtggtgtt gtcggggaaa tcatcgtcct ttccttggct gctcgcctgt    3720
gttgccacct ggattctgcg cgggacgtcc ttctgctacg tccccttcggc cctcaatcca    3780 gcggaccttc cttcccgcgg cctgctgccg gctctgcggc ctcttccgcg tcttcgcctt    3840
cgccctcaga cgagtcggat ctcccttggg ccgcctccc cgcctaagct tatcgatacc      3900
gtcgagatct aacttgttta ttgcagctta taatggttac aaataaagca atagcatcac    3960
aaatttcaca aataaagcat ttttttcact gcattctagt tgtggtttgt ccaaactcat    4020
caatgtatct tatcatgtct ggatctcgac ctcgactaga gcatggctac gtagataagt    4080
agcatggcgg gttaatcatt aactacaagg aaccccctagt gatggagttg gccactccct    4140
ctctgcgcgc tcgctcgctc actgaggccg ggcgaccaaa ggtcgcccga cgcccgggct    4200 tgcccgggc ggcctcagtg agcgagcgag cgcgccagct ggcgtaatag cgaagaggcc      4260
cgcaccgatc gcccttccca cagttgcgc agcctgaatg gcgaatggaa ttccagacga    4320
ttgagcgtca aaatgtaggt atttccatga gcgttttcc tgttgcaatg gctgcggta      4380 atattgttct ggatattacc agcaaggccg atagtttgag ttcttctact caggcaagtg    4440
atgttattac taatcaaaga agtattgcga caacggttaa tttgcgtgat ggacagactc    4500
ttttactcgg tggcctcact gattataaaa acacttctca ggattctggc gtaccgttcc    4560
tgtctaaaat ccctttaatc ggcctcctgt ttagctcccg ctctgattct aacgaggaaa    4620
gcacgttata cgtgctcgtc aaagcaacca tagtacgcgc cctgtagcgg cgcattaagc    4680
gcggcgggtg tggtggttac gcgcagcgtg accgctacac ttgccagcgc cctagcgccc    4740
```

```
gctcctttcg ctttcttccc ttcctttctc gccacgttcg ccggctttcc ccgtcaagct    4800
ctaaatcggg ggctcccttt agggttccga tttagtgctt tacggcacct cgaccccaaa    4860
aaacttgatt agggtgatgg ttcacgtagt gggccatcgc cctgatagac ggttttcgc     4920 cctttgacgt tggagtccac gttcttaat agtggactct tgttccaaac tggaacaaca    4980
ctcaacccta tctcggtcta ttcttttgat ttataaggga ttttgccgat ttcggcctat    5040
tggttaaaaa atgagctgat ttaacaaaaa tttaacgcga attttaacaa aatattaacg    5100
tttacaattt aaatatttgc ttatacaatc ttcctgtttt tggggctttt ctgattatca    5160
accggggtac atatgattga catgctagtt ttacgattac cgttcatcga ttctcttgtt    5220
tgctccagac tctcaggcaa tgacctgata gcctttgtag agacctctca aaaatagcta    5280
ccctctccgg catgaattta tcagctgaaa cggttgaata tcatattgat ggtgatttga    5340
ctgtctccgg cctttctcac ccgtttgaat ctttacctac acattactca ggcattgcat    5400
ttaaaatata tgagggttct aaaaattttt atccttgcgt tgaaataaag gcttctcccg    5460
caaaagtatt acagggtcat aatgttttg gtacaaccga tttagcttta tgctctgagg     5520
ctttattgct taattttgct aattctttgc cttgcctgta tgatttattg gatgttggaa    5580
ttcctgatgc ggtattttct ccttacgcat ctgtgcggta tttcacaccg catatggtgc    5640
actctcagta caatctgctc tgatgccgca tagttaagcc agccccgaca cccgccaaca    5700
cccgctgacg cgccctgacg ggcttgtctg ctcccggcat ccgcttacag acaagctgtg    5760
accgtctccg ggagctgcat gtgtcagagg ttttcaccgt catcaccgaa acgcgcgaga    5820
cgaaagggcc tcgtgatacg cctatttta taggttaatg tcatgataat aatggtttct     5880
tagacgtcag gtggcacttt tcggggaaat gtgcgcggaa cccctatttg tttattttc     5940 taaatacatt caaatatgta tccgctcatg agacaataac cctgataaat gcttcaataa    6000
tattgaaaaa ggaagagtat gagtattcaa catttccgtg tcgcccttat ccctttttt     6060 gcggcatttt gccttcctgt ttttgctcac ccagaaacgc tggtgaaagt aaaagatgct    6120
gaagatcagt tgggtgcacg agtgggttac atcgaactgg atctcaacag cggtaagatc    6180
cttgagagtt ttcgccccga agaacgtttt ccaatgatga gcacttttaa agttctgcta    6240
tgtggcgcgg tattatcccg tattgacgcc gggcaagagc aactcggtcg ccgcatacac    6300
tattctcaga atgacttggt tgagtactca ccagtcacag aaaagcatct tacgatggc     6360 atgacagtaa gagaattatg cagtgctgcc ataaccatga gtgataacac tgcggccaac    6420
ttacttctga caacgatcgg aggaccgaag gagctaaccg cttttttgca acacatgggg    6480
gatcatgtaa ctcgccttga tcgttgggaa ccggagctga atgaagccat accaaacgac    6540
gagcgtgaca ccacgatgcc tgtagcaatg gcaacaacgt tgcgcaaact attaactggc    6600
gaactactta ctctagcttc ccggcaacaa ttaatagact ggatggaggc ggataaagtt    6660
gcaggaccac ttctgcgctc ggcccttccg gctggctggt ttattgctga taaatctgga    6720
gccggtgagc gtgggtctcg cggtatcatt gcagcactgg ggccagatgg taagccctcc    6780
cgtatcgtag ttatctacac gacggggagt caggcaacta tggatgaacg aaatagacag    6840
atcgctgaga taggtgcctc actgattaag cattggtaac tgtcagacca agtttactca    6900
tatatacttt agattgattt aaaacttcat ttttaattta aaaggatcta ggtgaagatc    6960 cttttttgata atctcatgac caaaatccct taacgtgagt tttcgttcca ctgagcgtca    7020
gaccccgtag aaaagatcaa aggatcttct tgagatcctt ttttctgcg cgtaatctgc     7080 tgcttgcaaa caaaaaaacc accgctacca gcggtggttt gtttgccgga tcaagagcta    7140
```

```
ccaactctttt ttccgaaggt aactggcttc agcagagcgc agataccaaa tactgtcctt    7200
ctagtgtagc cgtagttagg ccaccacttc aagaactctg tagcaccgcc tacatacctc    7260
gctctgctaa tcctgttacc agtggctgct gccagtggcg ataagtcgtg tcttaccggg    7320
ttggactcaa gacgatagtt accggataag gcgcagcggt cgggctgaac ggggggttcg    7380
tgcacacagc ccagcttgga gcgaacgacc tacaccgaac tgagatacct acagcgtgag    7440
ctatgagaaa gcgccacgct tcccgaaggg agaaaggcgg acaggtatcc ggtaagcggc    7500
agggtcggaa caggagagcg cacgagggag cttccagggg gaaacgcctg gtatctttat    7560
agtcctgtcg ggtttcgcca cctctgactt gagcgtcgat ttttgtgatg ctcgtcaggg    7620 ggcggagcc tatggaaaaa cgccagcaac gcggcctttt tacggttcct ggccttttgc    7680
tggccttttg ctcacatgtt ctttcctgcg ttatccctg attctgtgga taaccgtatt    7740
accgcctttg agtgagctga taccgctcgc cgcagccgaa cgaccgagcg cagcgagtca    7800
gtgagcgagg aagcggaaga gcgcccaata cgcaaaccgc ctctccccgc gcgttggccg    7860
attcattaat g                                                          7871

<210> SEQ ID NO 14
<211> LENGTH: 7769
<212> TYPE: DNA
<213> ORGANISM: Artificial Sequence
<220> FEATURE:
<223> OTHER INFORMATION: GPR139 expression plasmid

<400> SEQUENCE: 14
cagcagctgc gcgctcgctc gctcactgag gccgcccggg caaagcccgg gcgtcgggcg      60
acctttggtc gcccggcctc agtgagcgag cgagcgcgca gagagggagt ggccaactcc     120
atcactaggg gttccttgta gttaatgatt aacccgccat gctacttatc tacgtagcca     180
tgctctagga cattgattat tgactagtgg agttccgcgt tacataactt acggtaaatg     240
gcccgcctgg ctgaccgccc aacgaccccc gcccattgac gtcaataatg acgtatgttc     300
ccatagtaac gccaataggg actttccatt gacgtcaatg ggtggagtat ttacggtaaa     360
ctgcccactt ggcagtacat caagtgtatc atatgccaag tacgccccct attgacgtca     420
atgacggtaa atggcccgcc tggcattatg cccagtacat gaccttatgg gactttccta     480
cttggcagta catctacgta ttagtcatcg ctattaccat ggtcgaggtg agccccacgt     540
tctgcttcac tctccccatc tccccccct cccaccccc aattttgtat ttatttattt     600
tttaattatt ttgtgcagcg atgggggcgg gggggggggg gggcgcgcgc caggcggggc     660 ggggcgggc gagggcggg gcggggcgag gcggagaggt gcggcggcag ccaatcagag     720
cggcgcgctc cgaaagtttc cttttatggc gaggcggcgg cggcggcggc cctataaaaa     780
gcgaagcgcg cggcgggcgg gagtcgctgc gcgctgcctt cgccccgtgc cccgctccgc     840
cgccgcctcg cgccgcccgc cccggctctg actgaccgcg ttactaaaac aggtaagtcc     900
ggcctccgcg ccgggttttg gcgcctcccg cgggcgcccc cctcctcacg cgagcgctg     960 ccacgtcaga cgaagggcgc agcgagcgtc ctgatcctc gcccggacg ctcaggacag    1020 cggcccgctg ctcataagac tcggccttag aaccccagta tcagcagaag gacattttag    1080
gacgggactt gggtgactct agggcactgg ttttctttcc agagagcgga acaggcgagg    1140
aaaagtagtc ccttctcggc gattctgcgg agggatctcc gtgggcggt gaacgccgat    1200 gatgcctcta ctaaccatgt tcatgttttc tttttttttc tacaggtcct gggtgacgaa    1260
```

```
cagggtaccg ccaccatggt gtccaaggga gaggagctgt tcaccggagt ggtgcccatc    1320
ctggtggagc tggacggcga tgtgaatggc cacaagttta gcgtgtccgg agagggagag    1380
ggcgacgcaa cctacggcaa gctgacactg aagttcatct gcaccacagg caagctgccc    1440
gtgccttggc caaccctggt gaccacactg acatacggcg tgcagtgttt ttctcggtat    1500
ccagaccaca tgaagcagca cgatttcttt aagagcgcca tgcccgaggg ctacgtgcag    1560
gagaggacaa tcttctttaa ggacgatggc aactataaga ccagagccga ggtgaagttc    1620
gagggcgaca cactggtgaa ccggatcgag ctgaagggca tcgactttaa ggaggatggc    1680
aatatcctgg ccacaagct ggagtacaac tataattccc acaacgtata catcatggcc    1740
gataagcaga agaacggcat caaggtgaac ttcaagatcc gccacaatat cgaggacggc    1800
tctgtgcagc tggccgatca ctaccagcag aacacccta tcggcgacgg acccgtgctg    1860
ctgcctgata atcactatct gtctacacag agcgccctgt ccaaggaccc aaacgagaag    1920
agggatcaca tggtgctgct ggagttcgtg accgcagcag gcatcacact gggcatggat    1980
gagctgtata agcgaaaaag aagatcaggt tcgggtgcgc cagtaaagca gacattaaac    2040
tttgatttgc tgaaacttgc aggtgatgta gagtcaaatc caggtccagg atccatggag    2100
cacacccacg cacacctggc agcaaacagc tccctgtcct ggtggtctcc tggcagcgcc    2160
tgcggactgg gcttcgtgcc agtggtgtac tatagcctgc tgctgtgcct gggactgcca    2220
gcaaacatcc tgacagtgat catcctgtcc cagctggtgg ccaggagaca gaagtctagc    2280
tacaattatc tgctggccct ggcagcagca gacatcctgg tgctgttctt tatcgtgttc    2340
gtggactttc tgctggagga tttcatcctg aacatgcaga tgccacaggt gcccgacaag    2400
atcatcgagg tgctggagtt ttcctctatc cacacctcca tctggatcac cgtgcctctg    2460
acaatcgata ggtacatcgc cgtgtgccac ccactgaagt accacaccgt gtcttatccc    2520
gccaggacaa gaaaagtgat cgtgagcgtg tacatcacct gtttcctgac atctatcccc    2580
tactattggt ggcctaatat ctggaccgag gattacatct ctacaagcgt gcaccacgtg    2640
ctgatctgga ttcactgctt cacagtgtat ctggtgccat gtagcatctt ctttatcctg    2700
aactccatca tcgtgtacaa gctgcggcgc aagtctaatt ttcggctgcg cggctatagc    2760
accggcaaga ccacagccat cctgttcacc atcacatcca tctttgccac actgtgggcc    2820
ccacggatca tcatgatcct gtaccacctg tatggagcac caatccagaa caggtggctg    2880
gtgcacatca tgtctgacat cgccaatatg ctggcctgc tgaacaccgc catcaatttc    2940
tttctgtact gcttcatcag caagaggttt agaaccatgg ccgccgccac actgaaggcc    3000
ttctttaagt gtcagaagca gcctgtgcag ttctacacca accacaattt ttccatcaca    3060
agctccccctt ggatctcccc agccaactct cactgcatca agatgctggt gtaccagtat    3120
gataagaatg gcaagcccat caaggtgagc ccctaccctt atgacgtgcc tgattacgcc    3180
tgaatctaga ataatcaacc tctggattac aaaatttgtg aaagattgac tggtattctt    3240
aactatgttg ctccttttac gctatgtgga tacgctgctt taatgccttt gtatcatgct    3300
attgcttccc gtatggcttt catttctcc tccttgtata aatcctggtt gctgtctctt    3360
tatgaggagt tgtggcccgt tgtcaggcaa cgtggcgtgg tgtgcactgt gtttgctgac    3420
gcaaccccca ctggttgggg cattgccacc acctgtcagc tcctttccgg gactttcgct    3480
ttccccctcc ctattgccac ggcggaactc atcgccgcct gccttgcccg ctgctggaca    3540
ggggctcggt gtgtgggcac tgacaattcc gtggtgttgt cggggaaatc atcgtccttt    3600
ccttggctgc tcgcctgtgt tgccacctgg attctgcgcg ggacgtcctt ctgctacgtc    3660
```

```
ccttcggccc tcaatccagc ggaccttcct tcccgcggcc tgctgccggc tctgcggcct   3720
cttccgcgtc ttcgccttcg ccctcagacg agtcggatct ccctttgggc cgcctccccg   3780
cctaagctta tcgataccgt cgagatctaa cttgtttatt gcagcttata atggttacaa   3840
ataaagcaat agcatcacaa atttcacaaa taaagcattt ttttcactgc attctagttg   3900
tggtttgtcc aaactcatca atgtatctta tcatgtctgg atctcgacct cgactagagc   3960
atggctacgt agataagtag catggcgggt taatcattaa ctacaaggaa cccctagtga   4020
tggagttggc cactccctct ctgcgcgctc gctcgctcac tgaggccggg cgaccaaagg   4080
tcgcccgacg cccgggcttt gcccgggcgg cctcagtgag cgagcgagcg cgcagctgg    4140 cgtaatagcg aagaggcccg caccgatcgc ccttcccaac agttgcgcag cctgaatggc   4200
gaatggaatt ccagacgatt gagcgtcaaa atgtaggtat ttccatgagc gtttttcctg   4260
ttgcaatggc tggcggtaat attgttctgg atattaccag caaggccgat agtttgagtt   4320
cttctactca ggcaagtgat gttattacta atcaaagaag tattgcgaca acggttaatt   4380
tgcgtgatgg acagactctt ttactcggtg gcctcactga ttataaaaac acttctcagg   4440
attctggcgt accgttcctg tctaaaatcc ctttaatcgg cctcctgttt agctcccgct   4500
ctgattctaa cgaggaaagc acgttatacg tgctcgtcaa agcaaccata gtacgcgccc   4560
tgtagcggcg cattaagcgc ggcgggtgtg gtggttacgc gcagcgtgac cgctacactt   4620
gccagcgccc tagcgcccgc tcctttcgct ttcttccctt cctttctcgc cacgttcgcc   4680
ggctttcccc gtcaagctct aaatcggggg ctcccttag ggttccgatt tagtgcttta   4740
cggcacctcg accccaaaaa acttgattag ggtgatggtt cacgtagtgg gccatcgccc   4800
tgatagacgt ttttcgccc tttgacgttg gagtccacgt tctttaatag tggactcttg   4860
ttccaaactg gaacaacact caaccctatc tcggtctatt cttttgattt ataagggatt   4920
ttgccgattt cggcctattg gttaaaaaat gagctgattt aacaaaaatt taacgcgaat   4980
tttaacaaaa tattaacgtt tacaatttaa atatttgctt atacaatctt cctgtttttg   5040
gggcttttct gattatcaac cggggtacat atgattgaca tgctagtttt acgattaccg   5100
ttcatcgatt ctcttgtttg ctccagactc tcaggcaatg acctgatagc ctttgtagag   5160
acctctcaaa aatagctacc ctctccggca tgaatttatc agctagaacg gttgaatatc   5220
atattgatgg tgatttgact gtctccggcc tttctcaccc gtttgaatct ttacctacac   5280
attactcagg cattgcattt aaaatatatg agggttctaa aattttttat ccttgcgttg   5340
aaataaaggc ttctcccgca aaagtattac agggtcataa tgtttttggt acaaccgatt   5400
tagctttatg ctctgaggct ttattgctta attttgctaa ttctttgcct tgcctgtatg   5460
atttattgga tgttggaatt cctgatgcgg tattttctcc ttacgcatct gtgcggtatt   5520
tcacaccgca tatggtgcac tctcagtaca atctgctctg atgccgcata gttaagccag   5580
ccccgacacc cgccaacacc cgctgacgcg ccctgacggg cttgtctgct cccggcatcc   5640
gcttacagac aagctgtgac cgtctccggg agctgcatgt gtcagaggtt ttcaccgtca   5700
tcaccgaaac gcgcgagacg aaagggcctc gtgatacgcc tatttttata ggttaatgtc   5760
atgataataa tggtttctta gacgtcaggt ggcacttttc ggggaaatgt gcgcggaacc   5820
cctatttgtt tatttttcta aatacattca aatatgtatc cgctcatgag acaataaccc   5880
tgataaatgc ttcaataata ttgaaaaagg aagagtatga gtattcaaca tttccgtgtc   5940
gcccttattc cctttttgc ggcatttgc cttcctgttt ttgctcaccc agaaacgctg   6000
```

-continued

```
gtgaaagtaa aagatgctga agatcagttg ggtgcacgag tgggttacat cgaactggat   6060
ctcaacagcg gtaagatcct tgagagtttt cgccccgaag aacgttttcc aatgatgagc   6120
acttttaaag ttctgctatg tggcgcggta ttatcccgta ttgacgccgg gcaagagcaa   6180
ctcggtcgcc gcatacacta ttctcagaat gacttggttg agtactcacc agtcacagaa   6240
aagcatctta cggatggcat gacagtaaga gaattatgca gtgctgccat aaccatgagt   6300
gataacactg cggccaactt acttctgaca acgatcggag gaccgaagga gctaaccgct   6360
tttttgcaca acatggggga tcatgtaact cgccttgatc gttgggaacc ggagctgaat   6420
gaagccatac caaacgacga gcgtgacacc acgatgcctg tagcaatggc aacaacgttg   6480
cgcaaactat taactggcga actacttact ctagcttccc ggcaacaatt aatagactgg   6540
atggaggcgg ataaagttgc aggaccactt ctgcgctcgg cccttccggc tggctggttt   6600
attgctgata aatctggagc cggtgagcgt gggtctcgcg gtatcattgc agcactgggg   6660
ccagatggta agccctcccg tatcgtagtt atctacacga cggggagtca ggcaactatg   6720
gatgaacgaa atagacagat cgctgagata ggtgcctcac tgattaagca ttggtaactg   6780
tcagaccaag tttactcata tatactttag attgatttaa aacttcattt ttaatttaaa   6840
aggatctagg tgaagatcct ttttgataat ctcatgacca aaatccctta acgtgagttt   6900
tcgttccact gagcgtcaga ccccgtagaa aagatcaaag gatcttcttg agatccttt   6960 tttctgcgcg taatctgctg cttgcaaaca aaaaaaccac cgctaccagc ggtggtttgt   7020
ttgccggatc aagagctacc aactctttt ccgaaggtaa ctggcttcag cagagcgcag   7080
ataccaaata ctgtccttct agtgtagccg tagttaggcc accacttcaa gaactctgta   7140
gcaccgccta catacctcgc tctgctaatc ctgttaccag tggctgctgc cagtggcgat   7200
aagtcgtgtc ttaccgggtt ggactcaaga cgatagttac cggataaggc gcagcggtcg   7260
ggctgaacgg ggggttcgtg cacacagccc agcttggagc gaacgaccta caccgaactg   7320
agatacctac agcgtgagct atgagaaagc gccacgcttc ccgaagggag aaaggcggac   7380
aggtatccgg taagcggcag ggtcggaaca ggagagcgca cgagggagct ccaggggga   7440 aacgcctggt atctttatag tcctgtcggg tttcgccacc tctgacttga gcgtcgattt   7500
ttgtgatgct cgtcaggggg gcggagccta tggaaaaacg ccagcaacgc ggccttttta   7560
cggttcctgg ccttttgctg gccttttgct cacatgttct ttcctgcgtt atcccctgat   7620
tctgtggata accgtattac cgcctttgag tgagctgata ccgctcgccg cagccgaacg   7680
accgagcgca gcgagtcagt gagcgaggaa gcggaagagc gcccaatacg caaaccgcct   7740
ctccccgcgc gttggccgat tcattaatg                                    7769
```

NEURORECEPTOR COMPOSITIONS AND METHODS OF USE

SEQUENCE LISTING SUBMISSION VIA EFS-WEB

A computer readable text file, entitled "101907-5005-US-Sequence-Listing.txt", created on or about Apr. 2, 2021, with a file size of 57,272 bytes contains the sequence listing for this application and is hereby incorporated by reference in its entirety.

BACKGROUND OF THE INVENTION

There remains a need for new or improved compounds and therapies for the treatment of neurological disorders.

SUMMARY OF THE INVENTION

Disclosed are compositions and methods for the treatment of neurological diseases such as Parkinson's disease, schizophrenia, Alzheimer's disease and Huntington's disease.

In one embodiment, a nucleic acid is provided comprising nucleotide sequence that encodes a dopamine receptor D1 (DRD1) polypeptide, wherein the nucleic acid sequence has been codon optimized for expression in humans.

In another embodiment, a nucleic acid is provided comprising nucleotide sequence that encodes a 5-Hydroxytryptamine receptor 4 (5HTR4) polypeptide, wherein the nucleic acid sequence has been codon optimized for expression in humans.

In another embodiment, a nucleic acid is provided comprising nucleotide sequence that encodes a G-protein coupled receptor 139 (GPR139) polypeptide, wherein the nucleic acid sequence has been codon optimized for expression in humans.

In related embodiments, an expression cassette is provided comprising a nucleotide sequence as herein described encoding a neuroreceptor polypeptide, wherein said nucleotide sequence is operably linked to an expression control sequence. In some embodiments, the expression control sequence comprises a constitutive promoter (e.g. a CAG, CBA or CASI promoter). In other embodiments, the expression control sequence comprises a tissue-specific promoter.

In other embodiments, a vector comprising a nucleic acid or expression cassette as herein described is provided. In some aspects, the vector is a non-viral vector (e.g. an expression plasmid). In other aspects, the vector is a viral vector (e.g. a recombinant adeno-associated virus (rAAV) vector). In some embodiments, the viral vector is an rAAV vector comprising a native capsid (e.g. a capsid of AAV serotype 2, 5, 6, 9 or rh10). In other embodiments, the rAAV vector comprises a capsid that is modified (e.g. comprises one or more peptide insertions and/or one or more amino acid substitutions and/or amino acid insertions or amino acid deletions) relative to a native AAV capsid (e.g. comprising one or more modifications relative to an AAV capsid of serotype 2, 5, 6 or 9). In preferred embodiments, the rAAV is a pseudotyped rAAV such as AAV2/5, AAV2/6 or AAV2/9.

In another embodiment, provided herein is a host cell comprising a nucleic acid as herein described. In some aspects, the host cell is a mammalian cell, including without limitation, a CHO cell, an HEK293 cell, a HeLa cell, a BHK21 cell, a Vero cell or a V27 cell.

In another embodiment, provided herein is a composition comprising a nucleic acid or vector as herein described and a pharmaceutically acceptable excipient. In some aspects, the composition is a pharmaceutical composition.

In some embodiments, the disclosure provides a method of treating a neurological disease in a subject (e.g. a human subject) by administering a nucleic acid, vector or pharmaceutical composition as herein described to the subject. In some aspects, the pharmaceutical composition, nucleic acid or vector is administered by intramuscular, intravenous, subcutaneous, intrathecal, intracisternal, intracerebroventricular, intracranial, intracerebral, intraparenchymal, intraganglionic and/or intranasal administration.

In some embodiments, a method of treating a psychiatric disorder is provided comprising administering to a subject in need thereof a nucleic acid, vector or pharmaceutical composition encoding a DRD1, 5HTR4 or GPR139 protein as herein described.

In other embodiments, a method of treating Parkinson's disease is provided comprising administering to a subject in need thereof a nucleic acid, vector or pharmaceutical composition encoding a DRD1 protein as herein described.

In other embodiments, a method of treating addiction is provided comprising administering to a subject need thereof a nucleic acid, vector or pharmaceutical composition encoding a DRD1 or GPR139 protein as herein described.

In other embodiments, a method of managing pain in a subject in need thereof is provided comprising administering to the subject a nucleic acid, vector or pharmaceutical composition encoding a GPR139 protein as herein described.

Also provided is a combination therapy comprising co-administering a nucleic acid, vector or pharmaceutical composition as herein described and a neurological agent to a subject (e.g. a human subject) in need thereof. In some embodiments, the therapeutically effective concentration of the neurological agent is reduced when co-administered with a pharmaceutical composition, nucleic acid or vector as herein described compared to the therapeutically effective concentration of the neurological agent when administered as a monotherapy. In some aspects, the neurological agent is selected from tetrabenazine (Xenazine for relief of chorea in Huntington's; 12.5-50 mg daily when administered as a monotherapy), neuroleptics such as haloperidol (0.5-15 mg daily when administered as a monotherapy), fluphenazine (1-10 mg daily when administered as a monotherapy), risperidone (0.5-10 mg daily when administered as a monotherapy), olanzapine (1.25-2.5 mg daily when administered as a monotherapy), levodopa (150-1000 mg daily dose), dopamine agonists (e.g. ropinirole, pramipexole, rotigotine), MAO-B inhibitors (e.g. selegiline, rasagiline), COMT-inhibitors (entacapone, tolcapone), amantadine, anticholinergics (trihexyphenidyl, benztropine).

DESCRIPTION OF THE DRAWINGS

FIG. 1 Vector pACASI-GFP-F2A-DRD1-HA-optimized is depicted. The location of 5' ITR, CASI promoter, eGFP encoding sequence, F2A sequence, DRD1 encoding sequence, WPRE, SV40 poly(A) sequence and 3' ITR are highlighted.

FIG. 2 Vector pACASI-GFP-F2A-5HTR4-HA-optimized is depicted. The location of 5' ITR, CASI promoter, eGFP encoding sequence, F2A sequence, 5HTR4 encoding sequence, WPRE, SV40 poly(A) sequence and 3' ITR are highlighted.

DETAILED DESCRIPTION OF THE INVENTION

Definitions

Figure 3:
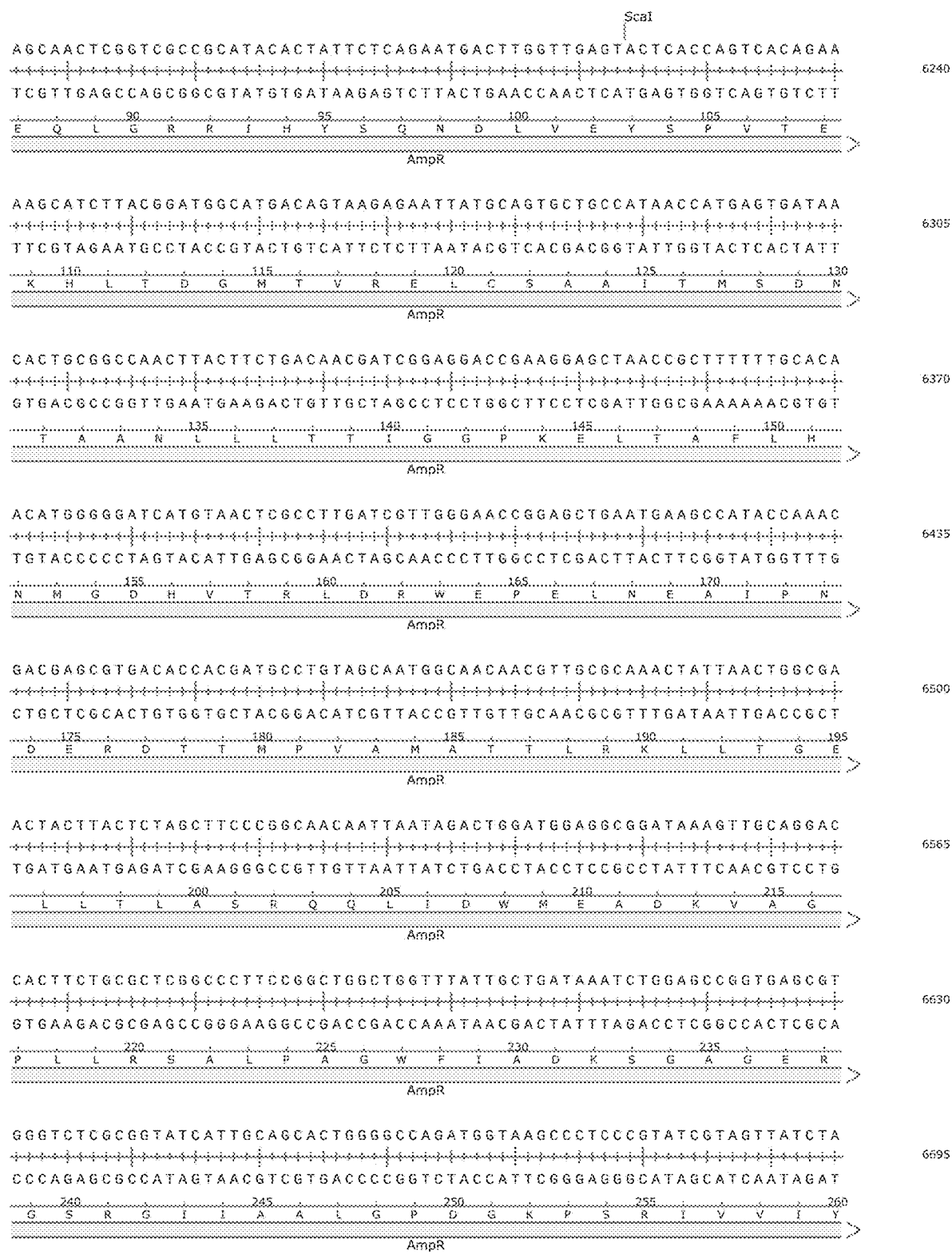
FIG. 3 Vector pACASI-GFP-F2A-GPR139-HA-optimized is depicted. The location of 5' ITR, CASI promoter, eGFP encoding sequence, F2A sequence, GPR139 encoding sequence, WPRE, SV40 poly(A) sequence and 3' ITR are highlighted.

A "codon adaptation index," as used herein, refers to a measure of codon usage bias. A codon adaptation index (CAI) measures the deviation of a given protein coding gene sequence with respect to a reference set of genes (Sharp P M and Li W H, Nucleic Acids Res. 15(3):1281-95 (1987)). CAI is calculated by determining the geometric mean of the weight associated to each codon over the length of the gene sequence (measured in codons):

$$CAI = \exp\left(1/L\sum_{l=1}^{L}\ln(w_1(l))\right), \quad \text{(I)}$$

For each amino acid, the weight of each of its codons, in CAI, is computed as the ratio between the observed frequency of the codon (fi) and the frequency of the synonymous codon (fj) for that amino acid:

$$w_i = \frac{f_i}{\max(f_j)} \quad ij \in [\text{synonymous codons for amino acid}] \quad \text{(II)}$$

The term "isolated" designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

As used herein, a "coding region" or "coding sequence" is a portion of polynucleotide which consists of codons translatable into amino acids. Although a "stop codon" (TAG, TGA, or TAA) is typically not translated into an amino acid, it can be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. Two or more coding regions can be present in a single polynucleotide construct, e.g., on a single vector, or in separate polynucleotide constructs, e.g., on separate (different) vectors. It follows, then that a single vector can contain just a single coding region or can comprise two or more coding regions.

A "2A peptide" refers to "self-cleaving" peptides of about 20 amino acids that produce equimolar levels of multiple genes from the same mRNA and may be used in place of IRES elements in multicistronic vectors. Non-limiting examples include T2A, P2A, E2A and F2A peptides sequences. In embodiments wherein a heterologous nucleic acid comprises nucleotide sequence encoding multiple gene products, expression of the multiple (e.g. 2) gene products can be mediated by multiple (e.g. 2) independent promoters or may be mediated by a single promoter, with the multiple transgenes separated by an internal ribosome entry site (IRES) or a 2A peptide sequence.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions can include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

As used herein, the term "nucleic acid" is interchangeable with "polynucleotide" or "nucleic acid molecule" and a polymer of nucleotides is intended.

A polynucleotide which encodes a gene product, e.g., a polypeptide, can include a promoter and/or other transcription or translation control elements operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other transcription control elements, besides a promoter, for example enhancers, operators, repressors, and transcription termination signals, can also be operably associated with a coding region to direct gene product expression.

"Transcriptional control sequences" or "expression control sequences" refer to DNA regulatory sequences, such as promoters, enhancers, terminators, and the like, that provide for the expression of a coding sequence in a host cell. A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit beta-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

A "CAG promoter" is composed of (C) the cytomegalovirus (CMV) early enhancer element, (A) the promoter, the first exon and the first intron of chicken beta-actin gene, (G) the splice acceptor of the rabbit beta-globin gene. See Miyazaki, J., Takaki, S., Araki, K., Tashiro, F., Tominaga, A., Takatsu, K., & Yamamura, K. (1989). Expression vector system based on the chicken β-actin promoter directs efficient production of interleukin-5. *Gene,* 79(2), 269-277, the contents of which are incorporated herein by reference.

A "CASI" promoter is composed of the CMV enhancer, chicken β-actin promoter, and UBC enhancer as well as splice donor (SD) and acceptor (SA) sequences. See e.g. Balazs et al., Nature 481, 81-84 (2012), the contents of which are incorporated herein by reference.

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), primary miRNA, small hairpin RNA (shRNA), small interfering RNA (siRNA), or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

A "vector" refers to any vehicle for the cloning of and/or transfer of a nucleic acid into a host cell. A vector can be a replicon to which another nucleic acid segment can be attached so as to bring about the replication of the attached segment. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion, of a polynucleotide into a suitable vector can be accomplished by ligating the appropriate polynucleotide fragments into a chosen vector that has complementary cohesive termini.

Vectors can be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), -galactosidase (LacZ), -glucuronidase (Gus), and the like. Selectable markers can also be considered to be reporters.

Eukaryotic viral vectors that can be used include, but are not limited to, adenovirus vectors, retrovirus vectors, adeno-associated virus vectors, poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

"Promoter" and "promoter sequence" are used interchangeably and refer to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths can have identical promoter activity.

The term "plasmid" refers to an extra-chromosomal element often carrying a gene that is not part of the central metabolism of the cell, and usually in the form of circular double-stranded DNA molecules. Such elements can be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA. Other techniques for alignment are described in Methods in Enzymology, vol. 266: Computer Methods for Macromolecular Sequence Analysis (1996), ed. Doolittle, Academic Press, Inc. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970).

Nucleic Acids Encoding Dopamine Receptor D1

Dopamine is involved in motivation, movement and cognition in the brain and is a key neurotransmitter in Parkinson's disease, schizophrenia and addiction. Dopamine receptors are broadly classified as D1-type and D2-type, based on their biochemical actions on adenylyl cyclase. D1-family (D1 and D5) receptors are coupled with a Gs/q-α subunit, whereas D2-family receptors (D2, D3, D4) are coupled with a Gi-α subunit. D1 dopamine receptors are exclusively expressed on postsynaptic neurons, whereas D2 dopamine receptors are expressed on both presynaptic and postsynaptic neurons. D1 dopamine receptors are densely expressed in the striatum, but are also expressed in the amygdala, olfactory bulb, cerebellum and prefrontal cortex. In the cerebral cortex, D1 dopamine receptors are expressed on dendrites of pyramidal cells and on interneurons. In the striatum, D1 dopamine receptors are expressed on medium spiny neurons.

During progression of Parkinson's' disease, there is a substantial loss of dopaminergic input to the striatum. Decreased signaling through D1 (and D2) dopamine receptors slows and disorganizes movement. Drugs targeting the dopaminergic system are widely used for treating psychiatric disorders. Dopamine replacement therapy with L-DOPA is the standard of care for treating motor aspects of Parkinson's disease; however, up to 80% of patients develop L-DOPA-induced dyskinesias within 5-10 years of initiating treatment.

In some embodiments, a nucleic acid is provided comprising nucleotide sequence encoding dopamine receptor D1 (DRD1). Representative human DRD1 sequences are found at GenBank Accession Nos. NP_000785.1 and NM_000794.5 (nt 968-2308).

In some preferred embodiments, a nucleic acid is provided comprising nucleotide sequence encoding human DRD1 and which has been codon-optimized for expression in humans. In some aspects, a codon-optimized nucleotide sequence encoding human DRD1 is provided having a nucleotide sequence at least 90%, at least 95%, at least 98% or at least 99% identical to the following:

(SEQ ID NO: 1)
ATGAGGACACTGAATACCTCTGCCATGGATGGCACAGGCCTGGTGGTGGAG

AGGGACTTTAGCGTGAGAATCCTGACCGCCTGCTTCCTGAGCCTGCTGATC

CTGTCCACACTGCTGGGCAATACCCTGGTGTGCGCCGCCGTGATCCGGTTT

CGCCACCTGAGATCCAAGGTGACAAACTTCTTTGTGATCAGCCTGGCCGTG

TCCGATCTGCTGGTGGCCGTGCTGGTCATGCCTTGGAAGGCAGTGGCAGAG

ATCGCAGGATTCTGGCCATTTGGCTCTTTCTGCAATATCTGGGTGGCCTTC

GATATCATGTGCTCCACCGCCTCTATCCTGAACCTGTGCGTGATCAGCGTG

GACCGGTACTGGGCCATCAGCTCCCCCTTCAGGTACGAGAGAAAGATGACA

CCCAAGGCCGCCTTCATCCTGATCAGCGTGGCCTGGACCCTGTCTGTGCTG

ATCAGCTTTATCCCCGTGCAGCTGTCCTGGCACAAGGCCAAGCCCACAAGC

CCTTCCGACGGCAATGCCACATCTCTGGCCGAGACCATCGATAACTGTGAC

TCTAGCCTGAGCCGCACCTACGCCATCTCCTCTAGCGTGATCTCCTTCTAT

ATCCCTGTGGCCATCATGATCGTGACATACACCCGGATCTATCGCATCGCC

CAGAAGCAGATCAGGAGAATCGCCGCCCTGGAGAGGGCAGCAGTGCACGCC

AAGAATTGCCAGACCACAACCGGCAACGGCAAGCCTGTGGAGTGTTCTCAG

CCAGAGTCCTCTTTCAAGATGAGCTTTAAGAGAGAGACAAAGGTGCTGAAG

ACCCTGTCCGTGATCATGGGCGTGTTCGTGTGCTGTTGGCTGCCTTTCTTT

ATCCTGAATTGCATCCTGCCATTTTGTGGCTCCGGCGAGACACAGCCCTTC

TGCATCGATTCTAACACCTTTGACGTGTTCGTGTGGTTTGGCTGGGCCAAT

AGCTCCCTGAACCCTATCATCTACGCCTTCAATGCCGATTTTCGGAAGGCC

TTCAGCACCCTGCTGGGCTGCTATCGCCTGTGCCCAGCCACAAACAATGCC

ATCGAGACCGTGTCCATCAACAATAACGGCGCCGCCATGTTCTCTAGCCAC

CACGAGCCCCGGGGCTCTATCAGCAAGGAGTGTAACCTGGTGTACCTGATC

CCTCACGCCGTGGGCTCCTCTGAGGACCTGAAGAAGGAGGAGGCAGCAGGA

ATCGCAAGGCCCCTGGAGAAGCTGTCCCCTGCCCTGTCTGTGATCCTGGAC

TACGATACCGACGTGAGCCTGGAGAAGATCCAGCCAATCACACAGAACGGC

CAGCACCCAACC.

In some embodiments, the nucleotide sequence encoding DRD1 is operably linked to an expression control sequence. In some embodiments, the expression control sequence comprises a viral, plant and/or mammalian promoter. In some aspects, the constitutive promoter is selected from a CAG promoter, a cytomegalovirus (CMV) immediate early promoter, a CASI promoter, a CBA promoter, an SV40 promoter, human elongation factor-1-alpha (ef1α), and human ubiquitin C (UCB) promoter.

In some preferred embodiments, the nucleotide sequence encoding DRD1 is operably linked to a CASI promoter having the following nucleotide sequence or a sequence at least 90%, at least 95%, at least 98% or at least 99% identical thereto:

(SEQ ID NO: 2)
ggagttccgcgttacataacttacggtaaatggcccgcctggctgaccgcc caacgacccccgcccattgacgtcaataatgacgtatgttcccatagtaac gccaatagggactttccattgacgtcaatgggtggagtatttacggtaaac tgcccacttggcagtacatcaagtgtatcatatgccaagtacgccccctat tgacgtcaatgacggtaaatggcccgcctggcattatgcccagtacatgac cttatgggactttcctacttggcagtacatctacgtattagtcatcgctat taccatggtcgaggtgagccccacgttctgcttcactctccccatctcccc cccctccccaccccaattttgtatttatttattttttaattattttgtgc agcgatggggggggggggggggggggcgcgcgccaggcggggcggggcgg ggcgaggggcggggcggggcgaggcggagaggtgcggcggcagccaatcag agcggcgcgctccgaaagtttccttttatggcgaggcggcggcggcggcgg ccctataaaaagcgaagcgcgcggcgggcgggagtcgctgcgcgctgcctt cgccccgtgccccgctccgccgccgcctcgcgccgcccgccccggctctga ctgaccgcgttactaaaacaggtaagtccggcctccgcgccgggttttggc -continued

```
gcctcccgcgggcgcccccctcctcacggcgagcgctgccacgtcagacga agggcgcagcgagcgtcctgatccttccgcccggacgctcaggacagcggc ccgctgctcataagactcggccttagaacccc agtatcagcagaaggacat tttaggacgggacttgggtgactctagggcactggttttctttccagagag cggaacaggcgaggaaaagtagtcccttctcggcgattctgcggagggatc tccgtggggcggtgaacgccgatgatgcctctactaaccatgttcatgttt tcttttttttctacaggtcctgggtgacgaacag
```

In some embodiments, the nucleic acid encoding DRD1 further comprises one or more sequences to increase expression of DRD1 from a vector (e.g. a viral vector). In preferred embodiments, the nucleic acid comprises a woodchuck hepatitis virus post-transcriptional regulatory element (WPRE), preferably located downstream of the DRD1 encoding sequence. In some preferred embodiments, the WPRE element has the following sequence or a sequence at least 90%, at least 95%, at least 98% or at least 99% identical thereto:

(SEQ ID NO: 3)
```
aatcaacctctggattacaaaatttgtgaaagattgactggtattcttaac tatgttgctccttttacgctatgtggatacgctgctttaatgcctttgtat catgctattgcttcccgtatggctttcattttctcctccttgtataaatcc tggttgctgtctctttatgaggagttgtggcccgttgtcaggcaacgtggc gtggtgtgcactgtgtttgctgacgcaaccccc actggttggggcattgcc accacctgtcagctcctttccgggactttcgctttccccctccctattgcc acggcggaactcatcgccgctgccttgcccgctgctggacaggggctcgg ctgttgggcactgacaattccgtggtgttgtcggggaaatcatcgtcctt t ccttggctgctcgcctgtgttgccacctggattctgcgcgggacgtccttc tgctacgtcccttcggccctcaatccagcggaccttccttcccgcggcctg ctgccggctctgcggcctcttccgcgtcttcgccttcgccctcagacgagt cggatctcccttt gggccgcctcccc gc
```

In some preferred embodiments, a vector is provided comprising a nucleic acid encoding DRD1 as herein described. In some embodiments, the vector is a viral vector. In preferred embodiments, the viral vector is a recombinant adeno-associated virus (rAAV). In a particularly preferred embodiment, the rAAV virus is a pseudotyped virus of type AAV2/6. In preferred embodiments the nucleic acid encapsidated within a capsid of serotype 6 comprises a 5' inverted terminal repeat (ITR) and 3' ITR of AAV2. In some aspects, the AAV2 5' ITR has the following sequence:

(SEQ ID NO: 4)
```
CTGCGCGCTCGCTCGCTCACTGAGGCCGCCCGGGCAAAGCCCGGGCGTCGG

GCGACCTTTGGTCGCCCGGCCTCAGTGAGCGAGCGAGCGCGCAGAGAGGGA

GTGGCCAACTCCATCACTAGGGGTTCCT
```

In related aspects, the AAV2 3' ITR has the following sequence:

(SEQ ID NO: 5)
```
AGGAACCCCTAGTGATGGAGTTGGCCACTCCCTCTCTGCGCGCTCGCTCGC

TCACTGAGGCCGGGCGACCAAAGGTCGCCCGACGCCCGGGCTTTGCCCGGG

CGGCCTCAGTGAGCGAGCGAGCGCGC
```

In some preferred aspects, the nucleic acid encoding DRD1 comprises (from 5' to 3'): (i) AAV2 5' ITR (ii) CASI promoter (iii) codon optimized DRD1 sequence (iv) WPRE (v) SV40 polyA sequence and (vi) 3' ITR. In some embodiments, nucleotide sequence encoding a second transgene (e.g. a reporter transgene such as GFP or RFP) is placed upstream (or downstream) of the DRD1 sequence and separated by a 2A peptide sequence allowing for expression of DRD1 and the second transgene from the CASI promoter (i.e. in a bicistronic formation). In preferred embodiments, an rAAV virion is provided comprising such a nucleic acid an AAV capsid. In particularly preferred embodiments the AAV capsid is a capsid of serotype 2, 5, 6 or 9, more preferably of serotype 2, 6 or 9.

In a particularly preferred embodiment, a nucleic acid encoding DRD1 is provided comprising the following nucleotide sequence or a sequence at least 80%, at least 85%, at least 90%, at least 95%, at least 98% or at least 99% identical thereto:

(SEQ ID NO: 6)
```
CTGCGCGCTCGCTCGCTCACTGAGGCCGCCCGGGCAAAGCCCGGGCGTCGG

GCGACCTTTGGTCGCCCGGCCTCAGTGAGCGAGCGAGCGCGCAGAGAGGGA

GTGGCCAACTCCATCACTAGGGGTTCCTTGTAGTTAATGATTAACCCGCCA

TGCTACTTATCTACGTAGCCATGCTCTAGGACATTGATTATTGACTAGTgg agttccgcgttacataacttacggtaaatggcccgcctggctgaccgccca acgaccccc gcccattgacgtcaataatgacgtatgttcccatagtaacgc caatagggactttccattgacgtcaatgggtggagtatttacggtaaactg cccacttggcagtacatcaagtgtatcatatgccaagtacgccccctattg acgtcaatgacggtaaatggcccgcctggcattatgcccagtacatgacct tatgggactttcctacttggcagtacatctacgtattagtcatcgctatta ccatggtcgaggtgagccccacgttctgcttcactctccccatctccccc c cctccccacccccaatttt gtatttatttatttttt aattattttt gtgcag cgatggggcgggggggggggggcgcgcgccaggcggggcggggcgggg cgaggggcggggcgggcgaggcggagaggtgcggcggcagccaatcagag cggcgcgctccgaaagtttccttttatggcgaggcggcggcggcggcggcc ctataaaaagcgaagcgcgcggcgggcgggagtcgctgcgcgctgccttcg ccccgtgccccgctccgccgccgcctcgcgccgcccgccccggctctgact gaccgcgttactaaaacaggtaagtccggcctccgcgccgggttttggcgc ctcccgcgggcgcccccctcctcacggcgagcgctgccacgtcagacgaag ggcgcagcgagcgtcctgatccttccgcccggacgctcaggacagcggccc gctgctcataagactcggccttagaacccc agtatcagcagaaggacattt taggacgggacttgggtgactctagggcactggttttctttccagagagcg
```

-continued

```
gaacaggcgaggaaaagtagtcccttctcggcgattctgcggagggatctc cgtggggcggtgaacgccgatgatgcctctactaaccatgttcatgttttc ttttttttctacaggtcctgggtgacgaacagGTACCGCCACCATGGTG

TCCAAGGGAGAGGAGCTGTTCACCGGAGTGGTGCCCATCCTGGTGGAGCTG

GACGGCGATGTGAATGGCCACAAGTTTAGCGTGTCCGGAGAGGGAGAGGGC

GACGCAACCTACGGCAAGCTGACACTGAAGTTCATCTGCACCACAGGCAAG

CTGCCCGTGCCTTGGCCAACCCTGGTGACCACACTGACATACGGCGTGCAG

TGTTTTTCTCGGTATCCAGACCACATGAAGCAGCACGATTTCTTTAAGAGC

GCCATGCCCGAGGGCTACGTGCAGGAGAGGACAATCTTCTTTAAGGACGAT

GGCAACTATAAGACCAGAGCCGAGGTGAAGTTCGAGGGCGACACACTGGTG

AACCGGATCGAGCTGAAGGGCATCGACTTTAAGGAGGATGGCAATATCCTG

GGCCACAAGCTGGAGTACAACTATAATTCCCACAACGTGTACATCATGGCC

GATAAGCAGAAGAACGGCATCAAGGTGAACTTCAAGATCCGCCACAATATC

GAGGACGGCTCTGTGCAGCTGGCCGATCACTACCAGCAGAACACCCCTATC

GGCGACGGACCCGTGCTGCTGCCTGATAATCACTATCTGTCTACACAGAGC

GCCCTGTCCAAGGACCCAAACGAGAAGAGGGATCACATGGTGCTGCTGGAG

TTCGTGACCGCAGCAGGCATCACACTGGGCATGGATGAGCTGTATAAGcga aaaagaagatcaggttcgggtgcgccagtaaagcagacattaaactttgat ttgctgaaacttgcaggtgatgtagagtcaaatccaggtccaGGATCCATG

AGGACACTGAATACCTCTGCCATGGATGGCACAGGCCTGGTGGTGGAGAGG

GACTTTAGCGTGAGAATCCTGACCGCCTGCTTCCTGAGCCTGCTGATCCTG

TCCACACTGCTGGGCAATACCCTGGTGTGCGCCGCCGTGATCCGGTTTCGC

CACCTGAGATCCAAGGTGACAAACTTCTTTGTGATCAGCCTGGCCGTGTCC

GATCTGCTGGTGGCCGTGCTGGTCATGCCTTGGAAGGCAGTGGCAGAGATC

GCAGGATTCTGGCCATTTGGCTCTTTCTGCAATATCTGGGTGGCCTTCGAT

ATCATGTGCTCCACCGCCTCTATCCTGAACCTGTGCGTGATCAGCGTGGAC

CGGTACTGGGCCATCAGCTCCCCCTTCAGGTACGAGAGAAAGATGACACCC

AAGGCCGCCTTCATCCTGATCAGCGTGGCCTGGACCCTGTCTGTGCTGATC

AGCTTTATCCCCGTGCAGCTGTCCTGGCACAAGGCCAAGCCCACAAGCCCT

TCCGACGGCAATGCCACATCTCTGGCCGAGACCATCGATAACTGTGACTCT

AGCCTGAGCCGCACCTACGCCATCTCCTCTAGCGTGATCTCCTTCTATATC

CCTGTGGCCATCATGATCGTGACATACACCCGGATCTATCGCATCGCCCAG

AAGCAGATCAGGAGAATCGCCGCCCTGGAGAGGGCAGCAGTGCACGCCAAG

AATTGCCAGACCACAACCGGCAACGGCAAGCCTGTGGAGTGTTCTCAGCCA

GAGTCCTCTTTCAAGATGAGCTTTAAGAGAGAGACAAAGGTGCTGAAGACC

CTGTCCGTGATCATGGGCGTGTTCGTGTGCTGTTGGCTGCCTTTCTTTATC

CTGAATTGCATCCTGCCATTTTGTGGCTCCGGCGAGACACAGCCCTTCTGC

ATCGATTCTAACACCTTTGACGTGTTCGTGTGGTTTGGCTGGGCCAATAGC

TCCCTGAACCCTATCATCTACGCCTTCAATGCCGATTTTCGGAAGGCCTTC

AGCACCCTGCTGGGCTGCTATCGCCTGTGCCCAGCCACAAACAATGCCATC

GAGACCGTGTCCATCAACAATAACGGCGCCGCCATGTTCTCTAGCCACCAC

GAGCCCCGGGGCTCTATCAGCAAGGAGTGTAACCTGGTGTACCTGATCCCT

CACGCCGTGGGCTCCTCTGAGGACCTGAAGAAGGAGGAGGCAGCAGGAATC

GCAAGGCCCCTGGAGAAGCTGTCCCCTGCCCTGTCTGTGATCCTGGACTAC

GATACCGACGTGAGCCTGGAGAAGATCCAGCCAATCACACAGAACGGCCAG

CACCCAACCTACCCCTATGATGTGCCCGACTATGCCTGACTCTAGAAtaat caacctctggattacaaaatttgtgaaagattgactggtattataactatg ttgctccttttacgctatgtggatacgctgctttaatgcctttgtatcatg ctattgatcccgtatggctttcattttctcctccttgtataaatcctggtt gctgtctctttatgaggagttgtggcccgttgtcaggcaacgtggcgtggt gtgcactgtgtttgctgacgcaaccccactggttggggcattgccaccac ctgtcagctccttccgggactttcgctttccccctccctattgccacggc ggaactcatcgccgcctgccttgcccgctgctggacagggctcggctgtt gggcactgacaattccgtggtgttgtcggggaaatcatcgtcctttccttg gctgctcgcctgtgttgccacctggattctgcgcgggacgtccttctgcta cgtcccttcggccctcaatccagcggaccttccttcccgcggcctgctgcc ggctctgcggcctcttccgcgtcttcgccttcgccctcagacgagtcggat ctcccctttgggccgcctccccgcctAAGCTTATCGATACCGTCGAGATCTA

ACTTGTTTATTGCAGCTTATAATGGTTACAAATAAAGCAATAGCATCACAA

ATTTCACAAATAAAGCATTTTTTTCACTGCATTCTAGTTGTGGTTTGTCCA

AACTCATCAATGTATCTTATCATGTCTGGATCTCGACCTCGACTAGAGCAT

GGCTACGTAGATAAGTAGCATGGCGGGTTAATCATTAACTACAAGGAACCC

CTAGTGATGGAGTTGGCCACTCCCTCTCTGCGCGCTCGCTCGCTCACTGAG

GCCGGGCGACCAAAGGTCGCCCGACGCCCGGGCTTTGCCCGGGCGGCCTCA

GTGAGCGAGCGAGCGCGC.
```

The nucleotide sequence set forth as SEQ ID NO:6 comprises (from 5' to 3'): (i) AAV2 5' ITR (ii) CASI promoter (iii) codon optimized eGFP sequence (iv) F2A sequence (v) codon optimized DRD1 sequence (vi) WPRE (vii) SV40 polyA sequence and (viii) 3' ITR.

In preferred embodiments, an rAAV comprising (i) a nucleic acid comprising the nucleotide sequence set forth as SEQ ID NO:6 and (ii) an AAV capsid. In particularly preferred embodiments the AAV capsid is a capsid of serotype 2, 5, 6 or 9, preferably of serotype 2, 6 or 9.

Nucleic Acids Encoding 5-Hydroxytryptamine Receptor 4

5-Hydroxytryptamine receptor 4 (5HTR4) is a member of the family of human serotonin receptors, which are G protein-coupled receptors that stimulate cAMP production in response to serotonin (5-hydroxytryptamine). The receptor is located in the alimentary tract, bladder, heart and adrenal gland as well as the central nervous system (putamen, caudate nucleus, nucleus accumbens, globus pallidus, substantia nigra, neocortex, raphe, poneine nuclei and some areas of the thalamus). the receptor functions in the peripheral and central nervous system to modulate the release of various neurotransmitters.

Serotonin plays an important role in several physiological processes in the periphery but also in the CNS through interaction with seventeen different 5HT receptors. Modulation of 5HTR activity has been connected to several different human pathologies including migraine, depression and schizophrenia. Based on the localization of the 5HTR4, ligands to 5HTR4 have been explored to treat depression, memory and gastrointestinal disorders. tegaserod ZEL-NORM™/ZELMAC™) and prucalopride are 5HTR4 agonists that have been approved for the treatment of irritable bowel syndrome and chronic constipation.

In some embodiments, a nucleic acid is provided comprising nucleotide sequence encoding 5HTR4. Representative human 5HTR4 sequences are found at GenBank Accession Nos. NP_000861.1, NP_001035259.1, NP_001035262.2, NP_001035263.1, and NP_001273339.1.

In some preferred embodiments, a nucleic acid is provided comprising nucleotide sequence encoding human 5HTR4 and which has been codon-optimized for expression in humans. In some aspects, a codon-optimized nucleotide sequence encoding human 5HTR4 is provided having a nucleotide sequence at least 90%, at least 95%, at least 98% or at least 99% identical to the following:

(SEQ ID NO: 7)
ATGGACAAGCTGGATGCCAATGTGAGCTCCGAGGAGGGCTTCGGCTCCGTG

GAGAAGGTGGTGCTGCTGACATTTCTGTCTACCGTGATCCTGATGGCCATC

CTGGGCAATCTGCTGGTCATGGTGGCCGTGTGCTGGGACAGGCAGCTGCGC

AAGATCAAGACAAACTACTTCATCGTGTCTCTGGCCTTTGCCGATCTGCTG

GTGAGCGTGCTGGTCATGCCTTTCGGCGCCATCGAGCTGGTGCAGGACATC

TGGATCTATGGCGAGGTGTTTTGCCTGGTGCGGACCAGCCTGGATGTGCTG

CTGACCACAGCCAGCATCTTCCACCTGTGCTGTATCTCCCTGGACCGCTAC

TATGCCATCTGCTGTCAGCCTCTGGTGTACCGGAATAAGATGACACCACTG

AGGATCGCCCTGATGCTGGGAGGATGTTGGGTCATCCCTACCTTCATCTCT

TTTCTGCCAATCATGCAGGGCTGGAACAATATCGGCATCATCGATCTGATC

GAGAAGAGGAAGTTCAACCAGAATTCCAACTCTACATACTGCGTGTTCATG

GTGAACAAGCCCTATGCCATCACCTGCAGCGTGGTGGCCTTCTACATCCCT

TTTCTGCTGATGGTGCTGGCCTACTATCGGATCTATGTGACAGCCAAGGAG

CACGCCCACCAGATCCAGATGCTGCAGAGGGCAGGAGCCTCTAGCGAGAGC

AGGCCACAGAGCGCCGACCAGCACTCCACACACAGGATGAGAACAGAGACC

AAGGCCGCCAAGACCCTGTGCATCATCATGGGCTGCTTCTGTCTGTGCTGG

GCCCCCTTCTTTGTGACCAATATCGTGGACCCCTTCATCGATTACAGTG

CCTGGCCAAGTGTGGACCGCCTTTCTGTGGCTGGGCTACATCAATAGCGGC

CTGAACCCCTTCCTGTATGCCTTTCTGAACAAGTCCTTCAGGAGAGCCTTT

CTGATCATCCTGTGCTGTGACGATGAGAGGTACAGGAGGCCCTCTATCCTG

GGCCAGACCGTGCCCTGTTCCACCACAACCATCAATGGCTCTACACACGTG

CTGAGGTATACCGTGCTGCACAGAGGCCACCACCAGGAGCTGGAGAAGCTG

CCAATCCACAACGATCCCGAGAGCCTGGAGTCCTGCTTT

In some embodiments, the nucleotide sequence encoding 5HTR4 is operably linked to an expression control sequence. In some embodiments, the expression control sequence comprises a viral, plant and/or mammalian promoter. In some aspects, the constitutive promoter is selected from a CAG promoter, a cytomegalovirus (CMV) immediate early promoter, a CASI promoter, a CBA promoter, an SV40 promoter, human ef1α promoter, and human UCB promoter. In a preferred embodiment, the expression control sequence comprises a CASI promoter, more preferably, a CASI promoter of SEQ ID NO:2.

In some embodiments, the nucleic acid encoding 5HTR4 further comprises one or more sequences to increase expression of 5HTR4 from a vector (e.g. a viral vector). In preferred embodiments, the nucleic acid comprises a woodchuck hepatitis virus post-transcriptional regulatory element (WPRE), preferably located downstream of the 5HTR4 encoding sequence. In some preferred embodiments, the WPRE element comprises the sequence of SEQ ID NO:3.

In some preferred embodiments, a vector is provided comprising a nucleic acid encoding 5HTR4 as herein described. In some embodiments, the vector is a viral vector. In preferred embodiments, the viral vector is a recombinant adeno-associated virus (rAAV). In a particularly preferred embodiment, the rAAV virus is a pseudotyped virus of type AAV2/6. In preferred embodiments the nucleic acid encapsidated within a capsid of serotype 6 comprises a 5' ITR and 3' ITR of AAV2, preferably of SEQ ID Nos: 4 and 5 respectively.

In some preferred aspects, the nucleic acid encoding 5HTR4 comprises (from 5' to 3'): (i) AAV2 5' ITR (ii) CASI promoter (iii) codon optimized 5HTR4 sequence (iv) WPRE (v) SV40 polyA sequence and (vi) 3' ITR. In some embodiments, nucleotide sequence encoding a second transgene (e.g. a reporter transgene such as GFP or RFP) is placed upstream (or downstream) of the 5HTR4 sequence and separated by a 2A peptide sequence allowing for expression of 5HTR4 and the second transgene from the CASI promoter (i.e. in a bicistronic formation). In preferred embodiments, an rAAV virion is provided comprising such a nucleic acid an AAV capsid. In particularly preferred embodiments the AAV capsid is a capsid of serotype 2, 5, 6 or 9, more preferably of serotype 2, 6 or 9.

In a particularly preferred embodiment, a nucleic acid encoding 5HTR4 is provided comprising the following nucleotide sequence or a sequence at least 80%, at least 85%, at least 90%, at least 95%, at least 98% or at least 99% identical thereto:

(SEQ ID NO: 8)
CTGCGCGCTCGCTCGCTCACTGAGGCCGCCCGGGCAAAGCCCGGGCGTCGG

GCGACCTTTGGTCGCCCGGCCTCAGTGAGCGAGCGAGCGCGCAGAGAGGGA

GTGGCCAACTCCATCACTAGGGGTTCCTTGTAGTTAATGATTAACCCGCCA

TGCTACTTATCTACGTAGCCATGCTCTAGGACATTGATTATTGACTAGTgg agttccgcgttacataacttacggtaaatggcccgcctggctgaccgccca acgacccccgcccattgacgtcaataatgacgtatgttcccatagtaacgc caatagggactttccattgacgtcaatgggtggagtatttacggtaaactg cccacttggcagtacatcaagtgtatcatatgccaagtacgccccctattg acgtcaatgacggtaaatggcccgcctggcattatgcccagtacatgacct tatgggactttcctacttggcagtacatctacgtattagtcatcgctatta ccatggtcgaggtgagccccacgttctgcttcactctccccatctcccccc cctccccacccccaatttttgtatttatttattttttaattattttgtgcag cgatggggcgggggggggggggggcgcgcgccaggcggggcggggcgggg cgaggggcggggcggggcgaggcggagaggtgcggcggcagccaatcagag -continued

```
cggcgcgctccgaaagtttccttttatggcgaggcggcggcggcggcggcc
ctataaaaagcgaagcgcgcggcgggcgggagtcgctgcgcgctgccttcg
ccccgtgccccgctccgccgccgcctcgcgccgcccgccccggctctgact
gaccgcgttactaaaacaggtaagtccggcctccgcgccgggttttggcgc
ctcccgcgggcgcccccctcctcacggcgagcgctgccacgtcagacgaag
ggcgcagcgagcgtcctgatccttccgcccggacgctcaggacagcggccc
gctgctcataagactcggccttagaaccccagtatcagcagaaggacattt
taggacgggacttgggtgactctagggcactggttttctttccagagagcg
gaacaggcgaggaaaagtagtcccttctcggcgattctgcggagggatctc
cgtgggcggtgaacgccgatgatgcctctactaaccatgttcatgttttc
ttttttttctacaggtcctgggtgacgaacagGTACCGCCACCATGGTG
TCCAAGGGAGAGGAGCTGTTCACCGGAGTGGTGCCCATCCTGGTGGAGCTG
GACGGCGATGTGAATGGCCACAAGTTTAGCGTGTCCGGAGAGGGAGAGGGC
GACGCAACCTACGGCAAGCTGACACTGAAGTTCATCTGCACCACAGGCAAG
CTGCCCGTGCCTTGGCCAACCCTGGTGACCACACTGACATACGGCGTGCAG
TGTTTTTCTCGGTATCCAGACCACATGAAGCAGCACGATTTCTTTAAGAGC
GCCATGCCCGAGGGCTACGTGCAGGAGAGGACAATCTTCTTTAAGGACGAT
GGCAACTATAAGACCAGAGCCGAGGTGAAGTTCGAGGGCGACACACTGGTG
AACCGGATCGAGCTGAAGGGCATCGACTTTAAGGAGGATGGCAATATCCTG
GGCCACAAGCTGGAGTACAACTATAATTCCCACAACGTGTACATCATGGCC
GATAAGCAGAAGAACGGCATCAAGGTGAACTTCAAGATCCGCCACAATATC
GAGGACGGCTCTGTGCAGCTGGCCGATCACTACCAGCAGAACACCCCTATC
GGCGACGGACCCGTGCTGCTGCCTGATAATCACTATCTGTCTACACAGAGC
GCCCTGTCCAAGGACCCAAACGAGAAGAGGGATCACATGGTGCTGCTGGAG
TTCGTGACCGCAGCAGGCATCACACTGGGCATGGATGAGCTGTATAAGcga
aaaagaagatcaggttcgggtgcgccagtaaagcagacattaaactttgat
ttgctgaaacttgcaggtgatgtagagtcaaatccaggtccaGGATCCATG
GACAAGCTGGATGCCAATGTGAGCTCCGAGGAGGGCTTCGGCTCCGTGGAG
AAGGTGGTGCTGCTGACATTTCTGTCTACCGTGATCCTGATGGCCATCCTG
GGCAATCTGCTGGTCATGGTGGCCGTGTGCTGGGACAGGCAGCTGCGCAAG
ATCAAGACAAACTACTTCATCGTGTCTCTGGCCTTTGCCGATCTGCTGGTG
AGCGTGCTGGTCATGCCTTTCGGCGCCATCGAGCTGGTGCAGGACATCTGG
ATCTATGGCGAGGTGTTTTGCCTGGTGCGACCAGCCTGGATGTGCTGCTG
ACCACAGCCAGCATCTTCCACCTGTGCTGTATCTCCCTGGACCGCTACTAT
GCCATCTGCTGTCAGCCTCTGGTGTACCGGAATAAGATGACACCACTGAGG
ATCGCCCTGATGCTGGGAGGATGTTGGGTCATCCCTACCTTCATCTCTTTT
CTGCCAATCATGCAGGGCTGGAACAATATCGGCATCATCGATCTGATCGAG
AAGAGGAAGTTCAACCAGAATTCCAACTCTACATACTGCGTGTTCATGGTG
AACAAGCCCTATGCCATCACCTGCAGCGTGGTGGCCTTCTACATCCCTTTT
CTGCTGATGGTGCTGGCCTACTATCGGATCTATGTGACAGCCAAGGAGCAC
```

```
GCCCACCAGATCCAGATGCTGCAGAGGGCAGGAGCCTCTAGCGAGAGCAGG
CCACAGAGCGCCGACCAGCACTCCACACACAGGATGAGAACAGAGACCAAG
GCCGCCAAGACCCTGTGCATCATCATGGGCTGCTTCTGTCTGTGCTGGGCC
CCCTTCTTTGTGACCAATATCGTGGACCCCTTCATCGATTACACAGTGCCT
GGCCAAGTGTGGACCGCCTTTCTGTGGCTGGGCTACATCAATAGCGGCCTG
AACCCCTTCCTGTATGCCTTTCTGAACAAGTCCTTCAGGAGAGCCTTTCTG
ATCATCCTGTGCTGTGACGATGAGAGGTACAGGAGGCCCTCTATCCTGGGC
CAGACCGTGCCCTGTTCCACCACAACCATCAATGGCTCTACACACGTGCTG
AGGTATACCGTGCTGCACAGAGGCCACCACCAGGAGCTGGAGAAGCTGCCA
ATCCACAACGATCCCGAGAGCCTGGAGTCCTGCTTTTACCCCTATGACGTG
CCTGATTATGCCTGACTCTAGAAtaatcaacctctggattacaaaatttgt
gaaagattgactggtattcttaactatgttgctccttttacgctatgtgga
tacgctgctttaatgcctttgtatcatgctattgcttcccgtatggctttc
attttctcctccttgtataaatcctggttgctgtctctttatgaggagttg
tggcccgttgtcaggcaacgtggcgtggtgtgcactgtgtttgctgacgca
acccccactggttggggcattgccaccacctgtcagctcctttccgggact
ttcgctttccccctccctattgccacggcggaactcatcgccgcctgcctt
gcccgctgctggacaggggctcggctgttgggcactgacaattccgtggtg
ttgtcggggaaatcatcgtcctttccttggctgctcgcctgtgttgccacc
tggattctgcgcgggacgtccttctgctacgtcccttcggccctcaatcca
gcggaccttccttcccgcggcctgctgccggctctgcggcctcttccgcgt
cttcgccttcgccctcagacgagtcggatctcccttttgggccgcctcccg
cctAAGCTTATCGATACCGTCGAGATCTAACTTGTTTATTGCAGCTTATAA
TGGTTACAAATAAAGCAATAGCATCACAAATTTCACAAATAAAGCATTTTT
TTCACTGCATTCTAGTTGTGGTTTGTCCAAACTCATCAATGTATCTTATCA
TGTCTGGATCTCGACCTCGACTAGAGCATGGCTACGTAGATAAGTAGCATG
GCGGGTTAATCATTAACTACAAGGAACCCCTAGTGATGGAGTTGGCCACTC
CCTCTCTGCGCGCTCGCTCGCTCACTGAGGCCGGGCGACCAAAGGTCGCCC
GACGCCCGGGCTTTGCCCGGGCGGCCTCAGTGAGCGAGCGAGCGCGC.
```

The nucleotide sequence set forth as SEQ ID NO:8 comprises (from 5' to 3'): (i) AAV2 5' ITR (ii) CASI promoter (iii) codon optimized eGFP sequence (iv) F2A sequence (v) codon optimized 5HTR4 sequence (vi) WPRE (vii) SV40 polyA sequence and (viii) 3' ITR.

In preferred embodiments, an rAAV comprising (i) a nucleic acid comprising the nucleotide sequence set forth as SEQ ID NO:8 and (ii) an AAV capsid. In particularly preferred embodiments the AAV capsid is a capsid of serotype 2, 5, 6 or 9, preferably of serotype 2, 6 or 9.

Nucleic Acids Encoding G-Protein Coupled Receptor 139

G-protein coupled receptor 139 (GPR139) is expressed in the striatum, thalamus, hypothalamus, pituitary and habenula of the CNS. It does not appear to be expressed peripheral tissues. Recent evidence supports that the aromatic amino acids may be endogenous signaling molecules for GPR139 and some similarities between the ligand binding pocket residues of GPR139 and the melanocortin 4 receptor (MC4R) have been reported. Small molecule surrogate agonists of GRP139 have been reported in Hu et al., J. Biomol. Screen, 14:789-797 (2009) and Shi et al., ACS Med Chem Lett, 2:303-306 (2011), the contents of both of which are incorporated herein by reference.

GPR139 is currently classified as an orphan receptor; however, recent studies have led to four primary hypotheses about the physiological function and therapeutic potential. First, GPR139 may have a role in control of locomotor activity (movement) and as such may play a role in the etiology of Parkinson's Disease. See Liu et al., Mol. Pharmacol., 88:911-925 (2015) and Andersen et al., Front Cell Neurosci, 10:164 (2016), the contents of both of which are incorporated herein by reference. Second, GPR139 may play a role in metabolism, in particular regulation of food consumption and/or energy expenditure. Third, GPR139 may play a role in alcohol addiction and hyperalgesia. See Kononoff et al., eNeuro, 5:1-14 (2018), the contents of which are incorporated herein by reference. GPR139 may play a role in the metabolic disorder phenylketonuria (PKU). Finally, GPR139 may play a role in schizophrenia and depression. See Castellani et al., Twin Res Hum Genet, 17:108-120 (2014) and US Patent Application Publication No. 2016/0145218, the contents of each of which are incorporated herein by reference.

In some embodiments, a nucleic acid is provided comprising nucleotide sequence encoding GPR139. Representative human GPR139 sequences are found at GenBank Accession Nos. NP_001002911.1 and NP_001305412.1.

In some preferred embodiments, a nucleic acid is provided comprising nucleotide sequence encoding human GPR139 and which has been codon-optimized for expression in humans. In some aspects, a codon-optimized nucleotide sequence encoding human GPR139 is provided having a nucleotide sequence at least 90%, at least 95%, at least 98% or at least 99% identical to the following:

(SEQ ID NO: 9)
ATGGAGCACACCCACGCACACCTGGCAGCAAACAGCTCCCTGTCCTGGTGG

TCTCCTGGCAGCGCCTGCGGACTGGGCTTCGTGCCAGTGGTGTACTATAGC

CTGCTGCTGTGCCTGGGACTGCCAGCAAACATCCTGACAGTGATCATCCTG

TCCCAGCTGGTGGCCAGGAGACAGAAGTCTAGCTACAATTATCTGCTGGCC

CTGGCAGCAGCAGACATCCTGGTGCTGTTCTTTATCGTGTTCGTGGACTTT

CTGCTGGAGGATTTCATCCTGAACATGCAGATGCCACAGGTGCCCGACAAG

ATCATCGAGGTGCTGGAGTTTTCCTCTATCCACACCTCCATCTGGATCACC

GTGCCTCTGACAATCGATAGGTACATCGCCGTGTGCCACCCACTGAAGTAC

CACACCGTGTCTTATCCCGCCAGGACAAGAAAAGTGATCGTGAGCGTGTAC

ATCACCTGTTTCCTGACATCTATCCCCTACTATTGGTGGCCTAATATCTGG

ACCGAGGATTACATCTCTACAAGCGTGCACCACGTGCTGATCTGGATTCAC

TGCTTCACAGTGTATCTGGTGCCATGTAGCATCTTCTTTATCCTGAACTCC

ATCATCGTGTACAAGCTGCGGCGCAAGTCTAATTTTCGGCTGCGCGGCTAT

AGCACCGGCAAGACCACAGCCATCCTGTTCACCATCACATCCATCTTTGCC

ACACTGTGGGCCCCACGGATCATCATGATCCTGTACCACCTGTATGGAGCA

CCAATCCAGAACAGGTGGCTGGTGCACATCATGTCTGACATCGCCAATATG

CTGGCCCTGCTGAACACCGCCATCAATTTCTTTCTGTACTGCTTCATCAGC

AAGAGGTTTAGAACCATGGCCGCCGCCACACTGAAGGCCTTCTTTAAGTGT

CAGAAGCAGCCTGTGCAGTTCTACACCAACCACAATTTTTCCATCACAAGC

TCCCCTTGGATCTCCCCAGCCAACTCTCACTGCATCAAGATGCTGGTGTAC

CAGTATGATAAGAATGGCAAGCCCATCAAGGTGAGCCCC

In some embodiments, the nucleotide sequence encoding GPR139 is operably linked to an expression control sequence. In some embodiments, the expression control sequence comprises a viral, plant and/or mammalian promoter. In some aspects, the constitutive promoter is selected from a CAG promoter, a cytomegalovirus (CMV) immediate early promoter, a CASI promoter, a CBA promoter, an SV40 promoter, human ef1α promoter, and human UCB promoter. In a preferred embodiment, the expression control sequence comprises a CASI promoter, more preferably, a CASI promoter of SEQ ID NO:2.

In some embodiments, the nucleic acid encoding GPR139 further comprises one or more sequences to increase expression of GPR139 from a vector (e.g. a viral vector). In preferred embodiments, the nucleic acid comprises a woodchuck hepatitis virus post-transcriptional regulatory element (WPRE), preferably located downstream of the GPR139 encoding sequence. In some preferred embodiments, the WPRE element comprises the sequence of SEQ ID NO:3.

In some preferred embodiments, a vector is provided comprising a nucleic acid encoding GPR139 as herein described. In some embodiments, the vector is a viral vector. In preferred embodiments, the viral vector is a recombinant adeno-associated virus (rAAV). In a particularly preferred embodiment, the rAAV virus is a pseudotyped virus of type AAV2/6. In preferred embodiments the nucleic acid encapsidated within a capsid of serotype 6 comprises a 5' ITR and 3' ITR of AAV2, preferably of SEQ ID Nos: 4 and 5 respectively.

In some preferred aspects, the nucleic acid encoding GPR139 comprises (from 5' to 3'): (i) AAV2 5' ITR (ii) CASI promoter (iii) codon optimized GPR139 sequence (iv) WPRE (v) SV40 polyA sequence and (vi) 3' ITR. In some embodiments, nucleotide sequence encoding a second transgene (e.g. a reporter transgene such as GFP or RFP) is placed upstream (or downstream) of the GPR139 sequence and separated by a 2A peptide sequence allowing for expression of GPR139 and the second transgene from the CASI promoter (i.e. in a bicistronic formation). In preferred embodiments, an rAAV virion is provided comprising such a nucleic acid an AAV capsid. In particularly preferred embodiments the AAV capsid is a capsid of serotype 2, 5, 6 or 9, preferably of serotype 2, 6 or 9.

In a particularly preferred embodiment, a nucleic acid encoding GPR139 is provided comprising the following nucleotide sequence or a sequence at least 80%, at least 85%, at least 90%, at least 95%, at least 98% or at least 99% identical thereto:

(SEQ ID NO: 10)
CTGCGCGCTCGCTCGCTCACTGAGGCCGCCCGGGCAAAGCCCGGGCGTCGG

GCGACCTTTGGTCGCCCGGCCTCAGTGAGCGAGCGAGCGCGCAGAGAGGGA

GTGGCCAACTCCATCACTAGGGGTTCCTTGTAGTTAATGATTAACCCGCCA

TGCTACTTATCTACGTAGCCATGCTCTAGGACATTGATTATTGACTAGTgg agttccgcgttacataacttacggtaaatggcccgcctggctgaccgccca

```
acgaccccgcccattgacgtcaataatgacgtatgttcccatagtaacgc
caatagggactttccattgacgtcaatgggtggagtatttacggtaaactg
cccacttggcagtacatcaagtgtatcatatgccaagtacgccccctattg
acgtcaatgacggtaaatggcccgcctggcattatgcccagtacatgacct
tatgggactttcctacttggcagtacatctacgtattagtcatcgctatta
ccatggtcgaggtgagcccacgttctgcttcactctccccatctccccc
cctccccaccccaattttgtatttatttattttttaattattttgtgcag
cgatggggcgggggggggggggcgcgcgccaggcggggcggggcgggg
cgagggcggggcggggcgaggcggagaggtgcggcggcagccaatcagag
cggcgcgctccgaaagtttccttttatggcgaggcggcggcggcggcggcc
ctataaaaagcgaagcgcgcggcgggcgggagtcgctgcgcgctgccttcg
ccccgtgccccgctccgccgcgcctcgcgccgcccgccccggctctgact
gaccgcgttactaaaacaggtaagtccggcctccgcgccgggttttggcgc
ctcccgcgggcgcccccctcctcacggcgagcgctgccacgtcagacgaag
ggcgcagcgagcgtcctgatccttccgcccggacgctcaggacagcggcc
gctgctcataagactcggccttagaaccccagtatcagcagaaggacattt
taggacgggacttgggtgactctagggcactggttttctttccagagagcg
gaacaggcgaggaaaagtagtcccttctcggcgattctgcggagggatctc
cgtggggcggtgaacgccgatgatgcctctactaaccatgttcatgttttt
ctttttttttctacaggtcctgggtgacgaacagGGTACCGCCACCATGGT
GTCCAAGGGAGAGGAGCTGTTCACCGGAGTGGTGCCCATCCTGGTGGAGCT
GGACGGCGATGTGAATGGCCACAAGTTTAGCGTGTCCGGAGAGGGAGAGGG
CGACGCAACCTACGGCAAGCTGACACTGAAGTTCATCTGCACCACAGGCAA
GCTGCCCGTGCCTTGGCCAACCCTGGTGACCACACTGACATACGGCGTGCA
GTGTTTTTCTCGGTATCCAGACCACATGAAGCAGCACGATTTCTTTAAGAG
CGCCATGCCCGAGGGCTACGTGCAGGAGAGGACAATCTTCTTTAAGGACGA
TGGCAACTATAAGACCAGACCGAGGTGAAGTTCGAGGGCGACACACTGGTG
AACCGGATCGAGCTGAAGGGCATCGACTTTAAGGAGGATGGCAATATCCTG
GGCCACAAGCTGGAGTACAACTATAATTCCCACAACGTGTACATCATGGCC
GATAAGCAGAAGAACGGCATCAAGGTGAACTTCAAGATCCGCCACAATATC
GAGGACGGCTCTGTGCAGCTGGCCGATCACTACCAGCAGAACACCCCTATC
GGCGACGGACCCGTGCTGCTGCCTGATAATCACTATCTGTCTACACAGAGC
GCCCTGTCCAAGGACCCAAACGAGAAGAGGGATCACATGGTGCTGCTGGAG
TTCGTGACCGCAGCAGGCATCACACTGGGCATGGATGAGCTGTATAAGcga
aaaagaagatcaggttcgggtgcgccagtaaagcagacattaaactttgat
ttgctgaaacttgcaggtgatgtagagtcaaatccaggtccaGGATCCATG
GAGCACACCCACGCACACCTGGCAGCAAACAGCTCCCTGTCCTGGTGGTCT
CCTGGCAGCGCCTGCGGACTGGGCTTCGTGCCAGTGGTGTACTATAGCCTG
CTGCTGTGCCTGGGACTGCCAGCAAACATCCTGACAGTGATCATCCTGTCC
CAGCTGGTGGCCAGGAGACAGAAGTCTAGCTACAATTATCTGCTGGCCCTG
GCAGCAGCAGACATCCTGGTGCTGTTCTTTATCGTGTTCGTGGACTTTCTG
CTGGAGGATTTCATCCTGAACATGCAGATGCCACAGGTGCCCGACAAGATC
ATCGAGGTGCTGGAGTTTTCCTCTATCCACACCTCCATCTGGATCACCGTG
CCTCTGACAATCGATAGGTACATCGCCGTGTGCCACCCACTGAAGTACCAC
ACCGTGTCTTATCCCGCCAGGACAAGAAAAGTGATCGTGAGCGTGTACATC
ACCTGTTTCCTGACATCTATCCCCTACTATTGGTGGCCTAATATCTGGACC
GAGGATTACATCTCTACAAGCGTGCACCACGTGCTGATCTGGATTCACTGC
TTCACAGTGTATCTGGTGCCATGTAGCATCTTCTTTATCCTGAACTCCATC
ATCGTGTACAAGCTGCGGCGCAAGTCTAATTTTCGGCTGCGCGGCTATAGC
ACCGGCAAGACCACAGCCATCCTGTTCACCATCACATCCATCTTTGCCACA
CTGTGGGCCCCACGGATCATCATGATCCTGTACCACCTGTATGGAGCACCA
ATCCAGAACAGGTGGCTGGTGCACATCATGTCTGACATCGCCAATATGCTG
GCCCTGCTGAACACCGCCATCAATTTCTTTCTGTACTGCTTCATCAGCAAG
AGGTTTAGAACCATGGCCGCCGCCACACTGAAGGCCTTCTTTAAGTGTCAG
AAGCAGCCTGTGCAGTTCTACACCAACCACAATTTTTCCATCACAAGCTCC
CCTTGGATCTCCCCAGCCAACTCTCACTGCATCAAGATGCTGGTGTACCAG
TATGATAAGAATGGCAAGCCCATCAAGGTGAGCCCCTACCCTTATGACGTG
CCTGATTACGCCTGAATCTAGAAtaatcaacctctggattacaaaatttgt
gaaagattgactggtattcttaactatgttgctccttttacgctatgtgga
tacgctgctttaatgcctttgtatcatgctattgcttcccgtatggctttc
attttctcctccttgtataaatcctggttgctgtctctttatgaggagttg
tggcccgttgtcaggcaacgtggcgtggtgtgcactgtgtttgctgacgca
acccccactggttggggcattgccaccacctgtcagctcctttccgggact
ttcgctttccccctccctattgccacggcggaactcatcgccgcctgcctt
gcccgctgctggacagggggctcggctgttgggcactgacaattccgtggtg
ttgtcggggaaatcatcgtcctttccttggctgctcgcctgtgttgccacc
tggattctgcgcgggacgtccttctgctacgtcccttcggccctcaatcca
gcggaccttccttcccgcggcctgctgccggctctgcggcctcttccgcgt
cttcgccttcgccctcagacgagtcggatctccattgggccgcctccccgc
ctAAGCTTATCGATACCGTCGAGATCTAACTTGTTTATTGCAGCTTATAAT
GGTTACAAATAAAGCAATAGCATCACAAATTTCACAAATAAAGCATTTTTT
TCACTGCATTCTAGTTGTGGTTTGTCCAAACTCATCAATGTATCTTATCAT
GTCTGGATCTCGACCTCGACTAGAGCATGGCTACGTAGATAAGTAGCATGG
CGGGTTAATCATTAACTACAAGGAACCCCTAGTGATGGAGTTGGCCACTCC
CTCTCTGCGCGCTCGCTCGCTCACTGAGGCCGGGCGACCAAAGGTCGCCCG
ACGCCCGGGCTTTGCCCGGGCGGCCTCAGTGAGCGAGCGAGCGCGC
```

The nucleotide sequence set forth as SEQ ID NO:10 comprises (from 5' to 3'): (i) AAV2 5' ITR (ii) CASI promoter (iii) codon optimized eGFP sequence (iv) F2A sequence (v) codon optimized GPR139 sequence (vi) WPRE (vii) SV40 polyA sequence and (viii) 3' ITR.

In preferred embodiments, an rAAV comprising (i) a nucleic acid comprising the nucleotide sequence set forth as SEQ ID NO:10 and (ii) an AAV capsid. In particularly preferred embodiments the AAV capsid is a capsid of serotype 2, 5, 6 or 9, preferably of serotype 2, 6 or 9.

Codon Optimized Sequences

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprises the codons encoding the amino acids of, any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE-US-00001

TABLE 1 The Standard Genetic Code

```
TCAGT TTT Phe (F) TCT Ser (S) TAT Tyr (Y) TGT Cys
(C) TTC Phe (F) TCC Ser (S) TAC Tyr (Y) TGC TTA Leu
(L) TCA Ser (S) TAA Stop TGA Stop TTG Leu (L) TCG
Ser (S) TAG Stop TGG Trp (W) C CTT Leu (L) CCT Pro
(P) CAT His (H) CGT Arg (R) CTC Leu (L) CCC Pro (P)
CAC His (H) CGC Arg (R) CTA Leu (L) CCA Pro (P) CAA
Gln (Q) CGA Arg (R) CTG Leu (L) CCG Pro (P) CAG Gln
(Q) CGG Arg (R) A ATT Ile (I) ACT Thr (T) AAT Asn
(N) AGT Ser (S) ATC Ile (I) ACC Thr (T) AAC Asn (N)
AGC Ser (S) ATA Ile (I) ACA Thr (T) AAA Lys (K) AGA
Arg (R) ATG Met (M) ACG Thr (T) AAG Lys (K) AGG Arg
(R) G GTT Val (V) GCT Ala (A) GAT Asp (D) GGT Gly
(G) GTC Val (V) GCC Ala (A) GAC Asp (D) GGC Gly (G)
GTA Val (V) GCA Ala (A) GAA Glu (E) GGA Gly (G) GTG
Val (V) GCG Ala (A) GAG Glu (E) GGG Gly (G)
```

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, the relative frequencies of codon usage have been calculated. Codon usage tables are available, for example, at the "Codon Usage Database" available at www.kazusa.or.jp/codon/ (visited Jun. 18, 2012). See Nakamura, Y., et al. Nucl. Acids Res. 28:292 (2000).

Randomly assigning codons at an optimized frequency to encode a given polypeptide sequence can be done manually by calculating codon frequencies for each amino acid, and then assigning the codons to the polypeptide sequence randomly. Additionally, various algorithms and computer software programs can be used to calculate an optimal sequence.

Non-Viral Vectors

In some embodiments, a non-viral vector (e.g. an expression plasmid, transposon, cosmid, bacterial artificial chromosome) comprising a nucleic acid encoding a DRD1, 5HTR4 or GPR139 protein as herein described is provided. Preferably, the non-viral vector is a plasmid comprising a nucleotide sequence of any one of SEQ ID Nos: 1, 7 and 9, or a sequence at least 90% identical thereto.

Viral Vectors

In preferred embodiments, a viral vector comprising a modified (codon optimized) nucleic acid as herein described is provided. Preferably, the viral vector comprises a nucleotide sequence of any one of SEQ ID Nos: 1, 7 and 9 or a sequence at least 90% identical thereto. A viral vector is a delivery vehicle that comprises a viral capsid or envelope surrounding a polynucleotide encoding a polypeptide or RNA. In some cases, the viral vector is derived from a replication-deficient virus. Examples of suitable viral vectors include but are not limited to adenoviral, retroviral (e.g. lentiviral), herpesvirus (e.g. HSV-1) and adeno-associated virus (AAV) vectors.

In a preferred embodiment, the viral vector includes a portion of a parvovirus genome, such as an AAV genome with the rep and cap genes deleted and/or replaced by the sequence encoding a codon optimized neuroreceptor as herein described and their associated expression control sequences. The sequence encoding modified human neuroreceptor gene sequence is typically inserted adjacent to one or two (i.e., is flanked by) AAV TRs or TR elements adequate for viral replication (Xiao et al., 1997, J. Virol. 71(2): 941-948), in place of the nucleic acid encoding viral rep and cap proteins. Other regulatory sequences suitable for use in facilitating tissue-specific expression of the modified neuroreceptor gene sequence in the target cell may also be included.

In some embodiments, the AAV viral vector comprises a nucleic acid comprising: (a) an AAV2 terminal repeat (b) a transcription control sequence (c) nucleotide sequence encoding a neuroreceptor as herein described (d) a polyadenylation sequence and (e) an AAV2 terminal repeat. In preferred embodiments, the nucleotide sequence encoding a neuroreceptor comprising a nucleotide sequence selected from those set forth as SEQ ID Nos: 1, 7 and 9. In other preferred embodiments, the transcription control sequence comprises a CASI promoter.

In other embodiments, the AAV viral vector comprises a nucleic acid comprising: (a) an AAV2 terminal repeat (b) a transcription control sequence (c) nucleotide sequence encoding a first polypeptide (d) a 2A sequence (e) nucleotide sequence encoding a neuroreceptor as herein described (f) a WRPE element (g) a polyadenylation sequence and (h) an AAV2 terminal repeat. In preferred embodiments, the nucleotide sequence encoding a neuroreceptor comprising a nucleotide sequence selected from those set forth as SEQ ID Nos: 1, 7 and 9. In other preferred embodiments, the transcription control sequence comprises a CASI promoter.

In some embodiments, the 5' ITR has the sequence of SEQ ID NO:4 and/or the 3' ITR has the sequence of SEQ ID NO:5.

In some embodiments, the polyadenylation sequence is an SV40 polyadenylation sequence having the following sequence:

```
                                              (SEQ ID NO: 11)
AACTTGTTTATTGCAGCTTATAATGGTTACAAATAAAGCAATAGCATCACA

AATTTCACAAATAAAGCATTTTTTTCACTGCATTCTAGTTGTGGTTTGTCC

AAACTCATCAATGTATCTTATCATGTCTGGATC
```

In some embodiments, the WPRE element comprises the sequence of SEQ ID NO:3

In particularly preferred embodiments, the AAV viral vector comprises a nucleic acid (transgene cassette) comprising the sequence of any of SEQ ID NOs: 6, 8 and 10 or a sequence at least 90%, at least 95%, at least 98% or at least 99% identical thereto.

Figure 2:
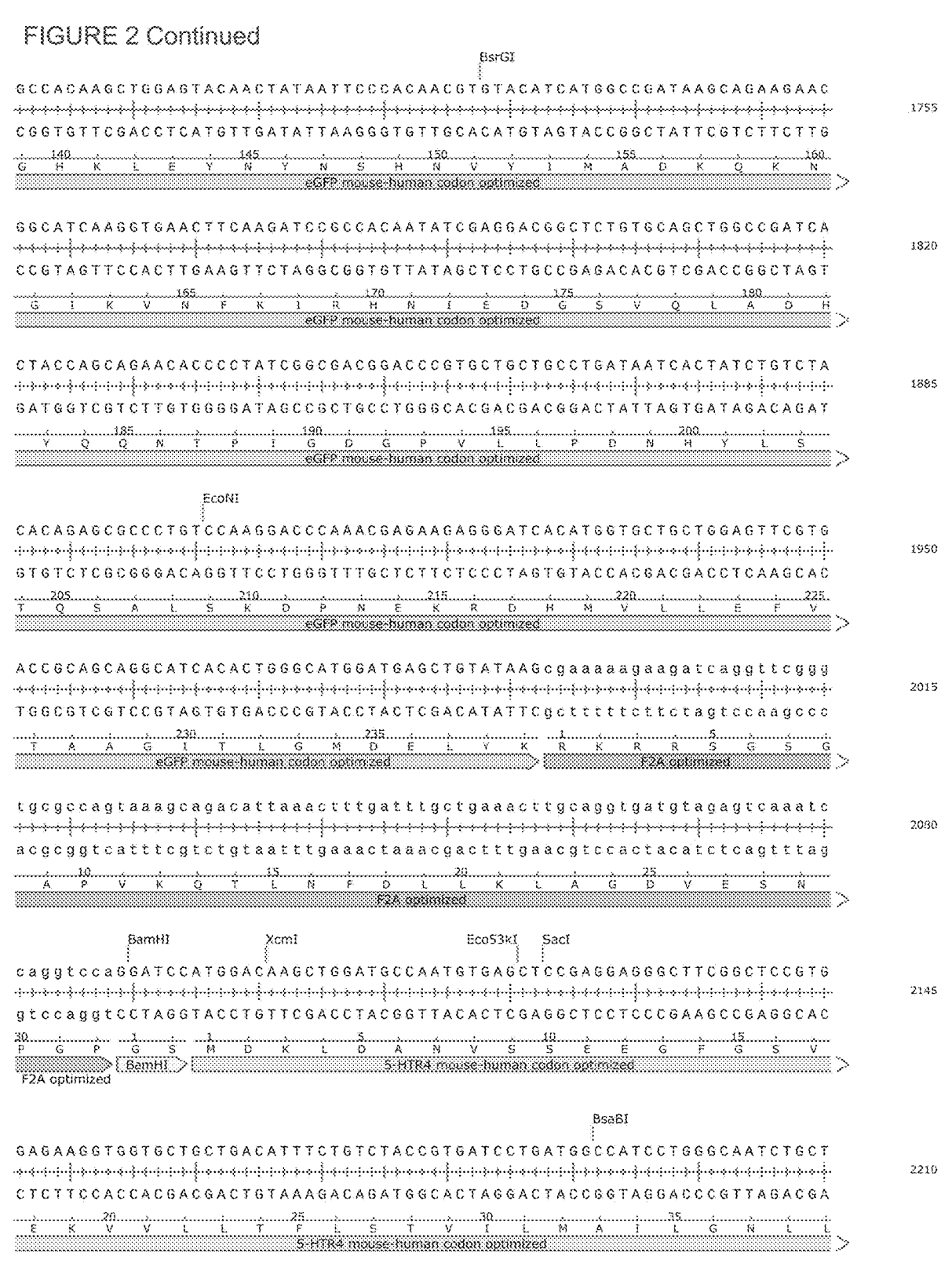

The components of the transgene cassettes of SEQ ID Nos 6, 8 and 10 and their respective locations are identified FIGS. 1-3.

Those skilled in the art will appreciate that an AAV vector comprising a transgene and lacking virus proteins needed for viral replication (e.g., cap and rep), cannot replicate since such proteins are necessary for virus replication and packaging. Helper viruses include, typically, adenovirus or herpes simplex virus. Alternatively, as discussed below, the helper functions (E1a, E1b, E2a, E4, and VA RNA) can be provided to a packaging cell including by transfecting the cell with one or more nucleic acids encoding the various helper elements and/or the cell can comprise the nucleic acid encoding the helper protein. For instance, HEK 293 were generated by transforming human cells with adenovirus 5 DNA and now express a number of adenoviral genes, including, but not limited to E1 and E3 (see, e.g., Graham et al., 1977, J. Gen. Virol. 36:59-72). Thus, those helper functions can be provided by the HEK 293 packaging cell without the need of supplying them to the cell by, e.g., a plasmid encoding them.

The viral vector may be any suitable nucleic acid construct, such as a DNA or RNA construct and may be single stranded, double stranded, or duplexed (i.e. self complementary as described in WO 2001/92551).

The viral capsid component of the packaged viral vectors may be a parvovirus capsid. AAV Cap and chimeric capsids are preferred. For example, the viral capsid may be an AAV capsid (e.g., AAV1, AAV2, AAV3, AAV4, AAV5, AAV6, AAV7 AAV8, AAV9, AAV10, AAV11, AAV12, AAV1.1, AAV2.5, AAV6.1, AAV6.3.1, AAV9.45, AAVrh10, AAVrh74, RHM4-1, AAV2-TT, AAV2-TT-S312N, AAV3B-S312N, AAV-LK03, snake AAV, avian AAV, bovine AAV, canine AAV, equine AAV, ovine AAV, goat AAV, shrimp AAV, and any other AAV now known or later discovered. see, e.g., Fields et al., VIROLOGY, volume 2, chapter 69 (4.sup.th ed., Lippincott-Raven Publishers).

In some embodiments, the viral capsid component of the packaged viral vector is a variant of a native AAV capsid (i.e. comprises one or more modifications (e.g. amino acid substitutions, insertions and/or deletions) relative to a native AAV capsid). In some embodiments, the capsid is a variant of an AAV2, AAV5, AAV6 or AAV9 capsid.

A full complement of AAV Cap proteins includes VP1, VP2, and VP3. The ORF comprising nucleotide sequences encoding AAV VP capsid proteins may comprise less than a full complement AAV Cap proteins or the full complement of AAV Cap proteins may be provided.

The invention includes packaging cells, which are encompassed by "host cells," which may be cultured to produce packaged viral vectors of the invention. The packaging cells of the invention generally include cells with heterologous (1) viral vector function(s), (2) packaging function(s), and (3) helper function(s). Each of these component functions is discussed in the ensuing sections.

Initially, the vectors can be made by several methods known to skilled artisans (see, e.g., WO 2013/063379). A preferred method is described in Grieger, et al. 2015, Molecular Therapy 24(2):287-297, the contents of which are incorporated by reference herein for all purposes. Briefly, efficient transfection of HEK293 cells is used as a starting point, wherein an adherent HEK293 cell line from a qualified clinical master cell bank is used to grow in animal component-free suspension conditions in shaker flasks and WAVE bioreactors that allow for rapid and scalable rAAV production. Using the triple transfection method (e.g., WO 96/40240), the suspension HEK293 cell line generates greater than $10^5$ vector genome containing particles (vg)/cell or greater than $10^{14}$ vg/L of cell culture when harvested 48 hours post-transfection. More specifically, triple transfection refers to the fact that the packaging cell is transfected with three plasmids: one plasmid encodes the AAV rep and cap genes, another plasmid encodes various helper functions (e.g., adenovirus or HSV proteins such as E1a, E1b, E2a, E4, and VA RNA, and another plasmid encodes the transgene and its various control elements (e.g., modified neuroreceptor gene and CASI promoter).

To achieve the desired yields, a number of variables are optimized such as selection of a compatible serum-free suspension media that supports both growth and transfection, selection of a transfection reagent, transfection conditions and cell density. A universal purification strategy, based on ion exchange chromatography methods, was also developed that resulted in high purity vector preps of AAV serotypes 1-6, 8, 9 and various chimeric capsids. This user-friendly process can be completed within one week, results in high full to empty particle ratios (>90% full particles), provides post-purification yields (>1.times.10.sup.13 vg/L) and purity suitable for clinical applications and is universal with respect to all serotypes and chimeric particles. This scalable manufacturing technology has been utilized to manufacture GMP Phase I clinical AAV vectors for retinal neovascularization (AAV2), Hemophilia B (scAAV8), Giant Axonal Neuropathy (scAAV9) and Retinitis Pigmentosa (AAV2), which have been administered into patients. In addition, a minimum of a 5-fold increase in overall vector production by implementing a perfusion method that entails harvesting rAAV from the culture media at numerous time-points post-transfection.

The packaging cells include viral vector functions, along with packaging and vector functions. The viral vector functions typically include a portion of a parvovirus genome, such as an AAV genome, with rep and cap deleted and replaced by the modified neuroreceptor sequence and its associated expression control sequences. The viral vector functions include sufficient expression control sequences to result in replication of the viral vector for packaging. Typically, the viral vector includes a portion of a parvovirus genome, such as an AAV genome with rep and cap deleted and replaced by the transgene and its associated expression control sequences. The transgene is typically flanked by two AAV TRs, in place of the deleted viral rep and cap ORFs. Appropriate expression control sequences are included, such as a tissue-specific promoter and other regulatory sequences suitable for use in facilitating tissue-specific expression of the transgene in the target cell. The transgene is typically a nucleic acid sequence that can be expressed to produce a therapeutic polypeptide or a marker polypeptide.

The terminal repeats (TR(s)) (resolvable and non-resolvable) selected for use in the viral vectors are preferably AAV sequences, with serotypes 1, 2, 3, 4, 5 and 6 being preferred. Resolvable AAV TRs need not have a wild-type TR sequence (e.g., a wild-type sequence may be altered by insertion, deletion, truncation or missense mutations), as long as the TR mediates the desired functions, e.g., virus packaging, integration, and/or provirus rescue, and the like. The TRs may be synthetic sequences that function as AAV inverted terminal repeats, such as the "double-D sequence" as described in U.S. Pat. No. 5,478,745 to Samulski et al., the entire disclosure of which is incorporated in its entirety herein by reference. Typically, but not necessarily, the TRs are from the same parvovirus, e.g., both TR sequences are from AAV2.

In some embodiments, an rAAV genome is packaged with a capsid of a different AAV serotype (and preferably, of a different serotype from the one or more AAV ITRs), and is referred to herein as a pseudotyped rAAV. For example, an rAAV type 1, 2, 3, 4, 5, 6, 7, 8, 9, or 10 genome may be encapsidated within an AAV type 1, 2, 3, 4, 5, 6, 7, 8, 9, 10 capsid or variants thereof, provided that the AAV capsid and genome (and preferably, the one or more AAV ITRs) are of different serotypes. In certain embodiments, a pseudotyped rAAV particle may be referred to as being of the type "x/y", where "x" indicates the source of ITRs and "y" indicates the serotype of capsid, for example a 2/6 rAAV particle has ITRs from AAV2 and a capsid from AAV6. Without limitation, illustrative examples of pseudotyped vectors include recombinant AAV2/5, AAV2/6 and AAV2/9 serotype vectors. In particular instances, provided herein is an AAV2/6 or AAV2/9 viral vector including a nucleic acid comprising nucleotide sequence encoding a neuroreceptor as herein described. See e.g. Viral Vectors for Gene Therapy: Methods and Protocols, ed. Machida, Humana Press, 2003.

In some instances, a particular AAV serotype vector may be selected based upon the intended use, e.g., based upon the intended route of administration. For example, for direct injection into the brain, e.g., either into the striatum, an AAV2 serotype vector can be used. For intrathecal delivery, e.g. an AAV9 or AAVrh10 serotype vector can be used. For intramuscular delivery, e.g. an AAV6 or AAV9 serotype vector can be used. For intraganglionic delivery, e.g. an AAV6 serotype vector can be used.

The packaging functions include capsid components. The capsid components are preferably from a parvoviral capsid, such as an AAV capsid or a chimeric AAV capsid function. Examples of suitable parvovirus viral capsid components are capsid components from the family Parvoviridae, such as an autonomous parvovirus or a Dependovirus. For example, the capsid components may be selected from AAV capsids, e.g., AAV1, AAV2, AAV3, AAV4, AAV5, AAV6, AAV7, AAV8, AAV9, AAV10, AAV11, AAV12, AAVrh10, AAVrh74, RHM4-1, RHM15-1, RHM15-2, RHM15-3/RHM15-5, RHM15-4, RHM15-6, AAV Hu.26, AAV1.1, AAV2.5, AAV6.1, AAV6.3.1, AAV9.45, AAV2i8, AAV2G9, AAV2i8G9, AAV2-TT, AAV2-TT-S312N, AAV3B-S312N, and AAV-LK03, and other novel capsids as yet unidentified or from non-human primate sources. Capsid components may include components from two or more AAV capsids.

The packaged viral vector generally includes sequence encoding a neuroreceptor as herein described and corresponding expression control sequence(s) flanked by TR elements, referred to herein as the "transgene" or "transgene expression cassette," sufficient to result in packaging of the vector DNA and subsequent expression of the interfering RNA and/or gene sequence in the transduced cell. The viral vector functions may, for example, be supplied to the cell as a component of a plasmid or an amplicon. The viral vector functions may exist extrachromosomally within the cell line and/or may be integrated into the cell's chromosomal DNA.

Any method of introducing the nucleotide sequence carrying the viral vector functions into a cellular host for replication and packaging may be employed, including but not limited to, electroporation, calcium phosphate precipitation, microinjection, cationic or anionic liposomes, and liposomes in combination with a nuclear localization signal. In embodiments wherein the viral vector functions are provided by transfection using a virus vector; standard methods for producing viral infection may be used.

The packaging functions include genes for viral vector replication and packaging. Thus, for example, the packaging functions may include, as needed, functions necessary for viral gene expression, viral vector replication, rescue of the viral vector from the integrated state, viral gene expression, and packaging of the viral vector into a viral particle. The packaging functions may be supplied together or separately to the packaging cell using a genetic construct such as a plasmid or an amplicon, a Baculovirus, or HSV helper construct. The packaging functions may exist extrachromosomally within the packaging cell, but are preferably integrated into the cell's chromosomal DNA. Examples include genes encoding AAV Rep and Cap proteins.

The helper functions include helper virus elements needed for establishing active infection of the packaging cell, which is required to initiate packaging of the viral vector. Examples include functions derived from adenovirus, baculovirus and/or herpes virus sufficient to result in packaging of the viral vector. For example, adenovirus helper functions will typically include adenovirus components E1a, E1b, E2a, E4, and VA RNA. The packaging functions may be supplied by infection of the packaging cell with the required virus. The packaging functions may be supplied together or separately to the packaging cell using a genetic construct such as a plasmid or an amplicon. See, e.g., pXR helper plasmids as described in Rabinowitz et al., 2002, J. Virol. 76:791, and pDG plasmids described in Grimm et al., 1998, Human Gene Therapy 9:2745-2760. The packaging functions may exist extrachromosomally within the packaging cell, but are preferably integrated into the cell's chromosomal DNA (e.g., E1 or E3 in HEK 293 cells).

Any suitable helper virus functions may be employed. For example, where the packaging cells are insect cells, baculovirus may serve as a helper virus. Herpes virus may also be used as a helper virus in AAV packaging methods. Hybrid herpes viruses encoding the AAV Rep protein(s) may advantageously facilitate for more scalable AAV vector production schemes.

Any method of introducing the nucleotide sequence carrying the helper functions into a cellular host for replication and packaging may be employed, including but not limited to, electroporation, calcium phosphate precipitation, microinjection, cationic or anionic liposomes, and liposomes in combination with a nuclear localization signal. In embodiments wherein the helper functions are provided by transfection using a virus vector or infection using a helper virus; standard methods for producing viral infection may be used.

Any suitable permissive or packaging cell known in the art may be employed in the production of the packaged viral vector. Mammalian cells or insect cells are preferred. Examples of cells useful for the production of packaging cells in the practice of the invention include, for example, human cell lines, such as VERO, WI38, MRC5, A549, HEK 293 cells (which express functional adenoviral E1 under the control of a constitutive promoter), B-50 or any other HeLa cells, HepG2, Saos-2, HuH7, and HT1080 cell lines. In one aspect, the packaging cell is capable of growing in suspension culture, more preferably, the cell is capable of growing in serum-free culture. In one embodiment, the packaging cell is a HEK293 that grows in suspension in serum free medium. In another embodiment, the packaging cell is the HEK293 cell described in U.S. Pat. No. 9,441,206 and deposited as ATCC No. PTA 13274. Numerous rAAV packaging cell lines are known in the art, including, but not limited to, those disclosed in WO 2002/46359. In another aspect, the packaging cell is cultured in the form of a cell stack (e.g. 10-layer cell stack seeded with HEK293 cells).

Cell lines for use as packaging cells include insect cell lines. Any insect cell which allows for replication of AAV and which can be maintained in culture can be used in accordance with the present invention. Examples include *Spodoptera frugiperda*, such as the Sf9 or Sf21 cell lines, *Drosophila* spp. cell lines, or mosquito cell lines, e.g., *Aedes albopictus* derived cell lines. A preferred cell line is the *Spodoptera frugiperda* Sf9 cell line. The following references are incorporated herein for their teachings concerning use of insect cells for expression of heterologous polypeptides, methods of introducing nucleic acids into such cells, and methods of maintaining such cells in culture: Methods in Molecular Biology, ed. Richard, Humana Press, N.J. (1995); O'Reilly et al., Baculovirus Expression Vectors: A Laboratory Manual, Oxford Univ. Press (1994); Samulski et al., 1989, J. Virol. 63:3822-3828; Kajigaya et al., 1991, Proc. Nat'l. Acad. Sci. USA 88: 4646-4650; Ruffing et al., 1992, J. Virol. 66:6922-6930; Kimbauer et al., 1996, Virol. 219: 37-44; Zhao et al., 2000, Virol. 272:382-393; and Samulski et al., U.S. Pat. No. 6,204,059.

Virus capsids according to the invention can be produced using any method known in the art, e.g., by expression from a baculovirus (Brown et al., (1994) Virology 198:477-488). As a further alternative, the virus vectors of the invention can be produced in insect cells using baculovirus vectors to deliver the rep/cap genes and rAAV template as described, for example, by Urabe et al., 2002, Human Gene Therapy 13:1935-1943.

In another aspect, the present invention provide for a method of rAAV production in insect cells wherein a baculovirus packaging system or vectors may be constructed to carry the AAV Rep and Cap coding region by engineering these genes into the polyhedrin coding region of a baculovirus vector and producing viral recombinants by transfection into a host cell. Notably when using Baculovirus production for AAV, preferably the AAV DNA vector product is a self-complementary AAV like molecule without using mutation to the AAV ITR. This appears to be a by-product of inefficient AAV rep nicking in insect cells which results in a self-complementary DNA molecule by virtue of lack of functional Rep enzyme activity. The host cell is a baculovirus-infected cell or has introduced therein additional nucleic acid encoding baculovirus helper functions or includes these baculovirus helper functions therein. These baculovirus viruses can express the AAV components and subsequently facilitate the production of the capsids.

During production, the packaging cells generally include one or more viral vector functions along with helper functions and packaging functions sufficient to result in replication and packaging of the viral vector. These various functions may be supplied together or separately to the packaging cell using a genetic construct such as a plasmid or an amplicon, and they may exist extrachromosomally within the cell line or integrated into the cell's chromosomes.

The cells may be supplied with any one or more of the stated functions already incorporated, e.g., a cell line with one or more vector functions incorporated extrachromosomally or integrated into the cell's chromosomal DNA, a cell line with one or more packaging functions incorporated extrachromosomally or integrated into the cell's chromosomal DNA, or a cell line with helper functions incorporated extrachromosomally or integrated into the cell's chromosomal DNA The rAAV vector may be purified by methods standard in the art such as by column chromatography or cesium chloride gradients. Methods for purifying rAAV vectors are known in the art and include methods described in Clark et al., 1999, Human Gene Therapy 10(6):1031-1039; Schenpp and Clark, 2002, Methods Mol. Med. 69:427-443; U.S. Pat. No. 6,566,118 and WO 98/09657.

Treatment Methods

In some embodiments, a nucleic acid or vector as herein described—or a pharmaceutical composition comprising such a nucleic acid or vector and a pharmaceutically acceptable excipient—is administered to a subject (e.g. a human) to treat a neurological disease or disorder.

Neurological disorders that can be treated by the compositions and methods described herein include post-traumatic stress disorder (PTSD), gastroesophageal reflex disease (GERD), addiction (e.g., alcohol, drugs), anxiety, depression, migraine, memory loss, dementia, sleep apnea, stroke, urinary incontinence, narcolepsy, essential tremor, movement disorder, atrial fibrillation, cancer (e.g., brain tumors), Parkinson's disease, schizophrenia, Huntington's disease, epilepsy or Alzheimer's disease. Other non-limiting examples of neurological diseases or disorders that can be treated by the compositions and methods herein include: Abulia, Agraphia, Alcoholism, Alexia, Aneurysm, Amaurosis fugax, Amnesia, Amyotrophic lateral sclerosis (ALS), Angelman syndrome, Aphasia, Apraxia, Arachnoiditis, Arnold-Chiari malformation, Asperger syndrome, Ataxia, Ataxia-telangiectasia, Attention deficit hyperactivity disorder, Auditory processing disorder, Autism spectrum, Bipolar disorder, Bell's palsy, Brachial plexus injury, Brain damage, Brain injury, Brain tumor, Canavan disease, Capgras delusion, Carpal tunnel syndrome, Causalgia, Central pain syndrome, Central pontine myelinolysis, Centronuclear myopathy, Cephalic disorder, Cerebral aneurysm, Cerebral arteriosclerosis, Cerebral atrophy, Cerebral autosomal dominant arteriopathy with subcortical infarcts and leukoencephalopathy (CADASIL), Cerebral gigantism, Cerebral palsy, Cerebral vasculitis, Cervical spinal stenosis, Charcot-Marie-Tooth disease, Chiari malformation, Chorea, Chronic fatigue syndrome, Chronic inflammatory demyelinating polyneuropathy (CIDP), Chronic pain, Coffin-Lowry syndrome, Coma, Complex regional pain syndrome, Compression neuropathy, Congenital facial diplegia, Corticobasal degeneration, Cranial arteritis, Craniosynostosis, Creutzfeldt-Jakob disease, Cumulative trauma disorders, Cushing's syndrome, Cyclothymic disorder, Cytomegalic inclusion body disease (CIBD), Cytomegalovirus Infection, Dandy-Walker syndrome, Dawson disease, De Morsier's syndrome, Dejerine-Klumpke palsy, Dejerine-Sottas disease, Delayed sleep phase syndrome, Dementia, Dermatomyositis, Developmental coordination disorder, Diabetic neuropathy, Diffuse sclerosis, Diplopia, Down syndrome, Dravet syndrome, Duchenne muscular dystrophy, Dysarthria, Dysautonomia, Dyscalculia, Dysgraphia, Dyskinesia, Dyslexia, Dystonia, Empty sella syndrome, Encephalitis, Encephalocele, Encephalotrigeminal angiomatosis, Encopresis, Enuresis, Epilepsy-intellectual disability in females, Erb's palsy, Erythromelalgia, Exploding head syndrome, Fabry's disease, Fahr's syndrome, Fainting, Familial spastic paralysis, Febrile seizures, Fisher syndrome, Friedreich's ataxia, Fibromyalgia, Foville's syndrome, Fetal alcohol syndrome, Fragile X syndrome, Fragile X-associated tremor/ataxia syndrome (FXTAS), Gaucher's disease, Generalized epilepsy with febrile seizures plus, Gerstmann's syndrome, Giant cell arteritis, Giant cell inclusion disease, Globoid Cell Leukodystrophy, Gray matter heterotopia, Guillain-Barre syndrome, Generalized anxiety disorder, HTLV-1 associated myelopathy, Hallervorden-Spatz disease, Head injury, Headache, Hemifacial Spasm, Hereditary Spastic Paraplegia, Heredopathia atactica polyneuritiformis, Herpes zoster oticus, Herpes zoster, Hirayama syndrome, Hirschsprung's disease, Holmes-Adie syndrome, Holoprosencephaly, Hydranencephaly, Hydrocephalus, Hypercortisolism, Hypoxia, Immune-Mediated encephalomyelitis, Inclusion body myositis, Incontinentia pigmenti, Infantile Refsum disease, Infantile spasms, Inflammatory myopathy, Intracranial cyst, Intracranial hypertension, Isodicentric 15, Joubert syndrome, Karak syndrome, Kearns-Sayre syndrome, Kinsbourne syndrome, Kleine-Levin Syndrome, Klippel Feil syndrome, Krabbe disease, Lafora disease, Lambert-Eaton myasthenic syndrome, Landau-Kleffner syndrome, Lateral medullary (Wallenberg) syndrome, Learning disabilities, Leigh's disease, Lennox-Gastaut syndrome, Lesch-Nyhan syndrome, Leukodystrophy, Leukoencephalopathy with vanishing white matter, Lewy body dementia, Lissencephaly, Locked-In syndrome, Lumbar disc disease, Lumbar spinal stenosis, Lyme disease-Neurological Sequelae, Machado-Joseph disease (Spinocerebellar ataxia type 3), Macrencephaly, Macropsia, Mal de debarquement, Megalencephalic leukoencephalopathy with subcortical cysts, Megalencephaly, Melkersson-Rosenthal syndrome, Menieres disease, Meningitis, Menkes disease, Metachromatic leukodystrophy, Microcephaly, Micropsia, Miller Fisher syndrome, Mini-stroke (transient ischemic attack), Misophonia, Mitochondrial myopathy, Mobius syndrome, Monomelic amyotrophy, Motor skills disorder, Moyamoya disease, Mucopolysaccharidoses, Multi-infarct dementia, Multifocal motor neuropathy, Multiple sclerosis, Multiple system atrophy, Muscular dystrophy, Myalgic encephalomyelitis, Myasthenia gravis, Myelinoclastic diffuse sclerosis, Myoclonic Encephalopathy of infants, Myoclonus, Myopathy, Myotubular myopathy, Myotonia congenita, Narcolepsy, Neuro-Behçet's disease, Neurofibromatosis, Neuroleptic malignant syndrome, Neurological manifestations of AIDS, Neurological sequelae of lupus, Neuromyotonia, Neuronal ceroid lipofuscinosis, Neuronal migration disorders, Neuropathy, Neurosis, Niemann-Pick disease, Non-24-hour sleep-wake disorder, Nonverbal learning disorder, O'Sullivan-McLeod syndrome, Occipital Neuralgia, Occult Spinal Dysraphism Sequence, Ohtahara syndrome, Olivopontocerebellar atrophy, Opsoclonus myoclonus syndrome, Optic neuritis, Orthostatic Hypotension, Otosclerosis, Overuse syndrome, Palinopsia, Paresthesia, Paramyotonia Congenita, Paraneoplastic diseases, Paroxysmal attacks, Parry-Romberg syndrome, PANDAS, Pelizaeus-Merzbacher disease, Periodic Paralyses, Peripheral neuropathy, Pervasive developmental disorders, Photic sneeze reflex, Phytanic acid storage disease, Pick's disease, Pinched nerve, Pituitary tumors, PMG, Polyneuropathy, Polio, Polymicrogyria, Polymyositis, Porencephaly, Post-Polio syndrome, Postherpetic Neuralgia (PHN), Postural Hypotension, Prader-Willi syndrome, Primary Lateral Sclerosis, Prion diseases, Progressive hemifacial atrophy, Progressive multifocal leukoencephalopathy, Progressive Supranuclear Palsy, Prosopagnosia, Pseudotumor cerebri, Quadrantanopia, Quadriplegia, Rabies, Radiculopathy, Ramsay Hunt syndrome type I, Ramsay Hunt syndrome type II, Ramsay Hunt syndrome type III, Rasmussen encephalitis, Reflex neurovascular dystrophy, Refsum disease, REM sleep behavior disorder, Repetitive stress injury, Restless legs syndrome, Retrovirus-associated myelopathy, Rett syndrome, Reye's syndrome, Rhythmic Movement Disorder, Romberg syndrome, Saint Vitus dance, Sandhoff disease, Schilder's disease, Schizencephaly, Sensory processing disorder, Septo-optic dysplasia, Shaken baby syndrome, Shingles, Shy-Drager syndrome, Sjogren's syndrome, Sleep apnea, Sleeping sickness, Snatiation, Sotos syndrome, Spasticity, Spina bifida, Spinal cord injury, Spinal cord tumors, Spinal muscular atrophy, Spinal and bulbar muscular atrophy, Spinocerebellar ataxia, Split-brain, Steele-Richardson-Olszewski syndrome, Stiff-person syndrome, Stroke, Sturge-Weber syndrome, Stuttering, Subacute sclerosing panencephalitis, Subcortical arteriosclerotic encephalopathy, Superficial siderosis, Sydenham's chorea, Syncope, Synesthesia, Syringomyelia, Tarsal tunnel syndrome, Tardive dyskinesia, Tardive dysphrenia, Tarlov cyst, Tay-Sachs disease, Temporal arteritis, Temporal lobe epilepsy, Tetanus, Tethered spinal cord syndrome, Thomsen disease, Thoracic outlet syndrome, Tic Douloureux, Todd's paralysis, Tourette syndrome, Toxic encephalopathy, Transient ischemic attack, Transmissible spongiform encephalopathies, Transverse myelitis, Traumatic brain injury, Tremor, Trichotillomania, Trigeminal neuralgia, Tropical spastic paraparesis, Trypanosomiasis, Tuberous sclerosis, Unverricht-Lundborg disease, Von Hippel-Lindau disease (VHL), Viliuisk Encephalomyelitis (VE), Wallenberg's syndrome, West syndrome, Whiplash, Williams syndrome, Wilson's disease, or Zellweger syndrome.

In other embodiments, a nucleic acid as herein described—or a pharmaceutical composition comprising such a nucleic acid and a pharmaceutically acceptable excipient—is administered to a subject (e.g. a human) to treat an eating disorder. An eating disorder may be a mental disorder defined by abnormal eating behaviors that negatively affect a subject's physical or mental health. In some cases, the eating disorder is anorexia nervosa. In other cases, the eating disorder is bulimia nervosa. In some cases, the eating disorder is pica, rumination disorder, avoidant/restrictive food intake disorder, binge eating disorder (BED), other specified feeding and eating disorder (OSFED), compulsive overeating, diabulimia, orthorexia nervosa, selective eating disorder, drunkorexia, pregorexia, or Gourmand syndrome.

In some aspects, a ligand that activates the neuroreceptor (DRD1, 5HTR4 or GPR139) is co-administered to the subject in an effective amount to control the activity of the receptor in the subject.

In preferred embodiments, the nucleic acid is delivered to the subject in a recombinant AAV (rAAV) vector, preferably wherein the rAAV vector is a pseudotyped AAV2/6 or AAV2/9 vector or a pharmaceutical composition comprising such a vector and a pharmaceutically acceptable excipient.

In related aspects, a nucleic acid or vector as herein described for use in the treatment of a neurological disease or disorder or for the manufacture of a medicament for the treatment of a neurological disease or disorder is provided.

Also provided herein are compositions comprising a nucleic acid as herein described, preferably encapsidated within an rAAV (e.g. comprising a capsid of serotype 6). Also provided herein are pharmaceutical compositions comprising: a) a nucleic acid as herein described, preferably encapsidated within an rAAV and; and b) a pharmaceutically acceptable carrier, diluent, excipient, or buffer. In some embodiments, the pharmaceutically acceptable carrier, diluent, excipient, or buffer is suitable for use in a human or non-human patient. Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, surfactants, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

In some embodiments, the pharmaceutical composition comprises $1\times10^8$ to $1\times10^{15}$ vector particles/kg or vector genomes/kg, $1\times10^{12}$ to $1\times10^{15}$ vector particles or vector genomes, or about $1\times10^{12}$, about $2\times10^{12}$, $3\times10^{12}$, about $4\times10^{12}$, about $5\times10^{12}$, about $6\times10^{12}$, about $7\times10^{12}$, about $8\times10^{12}$, about $9\times10^{12}$, about $1\times10^{13}$, about $2\times10^{13}$, about $3\times10^{13}$, about $4\times10^{13}$, about $5\times10^{13}$, about $6\times10^{13}$, about $7\times10^{13}$, about $8\times10^{13}$, about $9\times10^{13}$, about $1\times10^{14}$, about $2\times10^{14}$, about $3\times10^{14}$, about $4\times10^{14}$, about $5\times10^{14}$ about $6\times10^{14}$, about $7\times10^{14}$, about $8\times10^{14}$, about $9\times10^{14}$ or about $1\times10^{15}$ vector particles/kg or vector genomes/kg.

EXAMPLES

The following examples illustrate preferred embodiments of the present invention and are not intended to limit the scope of the invention in any way. While this invention has been described in relation to its preferred embodiments, various modifications thereof will be apparent to one skilled in the art from reading this application.

Example 1

The cDNA sequences for human neuroreceptors dopamine receptor D1 (DRD1), 5-Hydroxytryptamine receptor 4 (5HTR4), and G-protein coupled receptor 139 (GPR139) were codon optimized to generate cDNA sequences with increased expression in human cells.

Codon optimized sequence encoding each gene was placed within a plasmid under the control of a CASI promoter and flanked by AAV2 ITRs.

The sequence of pACASI-GFP-F2A-DRD1-HA-optimized vector is shown at FIG. 1. The location of 5' ITR, CASI promoter, eGFP encoding sequence, F2A sequence, DRD1 encoding sequence, WPRE, SV40 poly(A) sequence and 3' ITR are highlighted.

The sequence of pACASI-GFP-F2A-5HRT4-HA-optimized vector is shown at FIG. 2. The location of 5' ITR, CASI promoter, eGFP encoding sequence, F2A sequence, 5HRT4 encoding sequence, WPRE, SV40 poly(A) sequence, and 3' ITR are highlighted.

The sequence of pACASI-GFP-F2A-GPR139-HA-optimized vector is shown at FIG. 3. The location of 5' ITR, CASI promoter, eGFP encoding sequence, F2A sequence, GPR139 encoding sequence, WPRE, SV40 poly(A) sequence, and 3' ITR are highlighted.

To confirm transgene expression from the plasmids, HEK293 cells were (separately) transfected with DRD1, 5HTR4 and GPR139 with the aforementioned AAV vector plasmids. Briefly, HEK293 cells were seeded in 96-well plates in DMEM/10% FBS media. The next day, plasmid DNA (pACASI-GFP-F2A-GPR139-HA, pACASI-GFP-F2A-5HRT4-HA or pACASI-GFP-F2A-DRD1-HA) was added to the cells. 48 hrs post-transfection cells were imaged for the presence of GFP.

Figure 4:
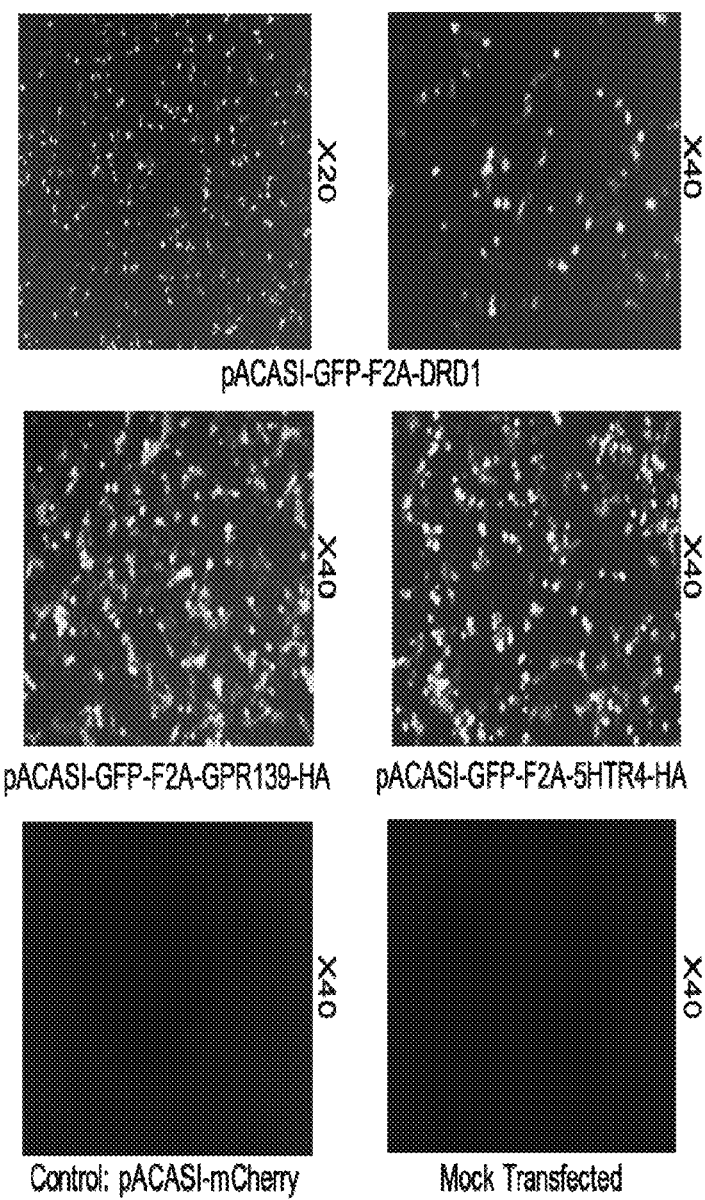
FIG. 4 shows imaging results in HEK293 cells transfected with each of the plasmids depicted in FIGS. 1-3, 48 hours after transfection FIGS. 5A-B

As can be seen from FIG. 4, robust expression of GFP from each plasmid was observed (compare to mock transfected cells and cells transfected with control vector).

Next, rAAV populations were generated comprising a capsid of serotype 6 and (i) a nucleic acid comprising the sequence of SEQ ID NO:6 (encoding DRD1) (ii) a nucleic acid comprising the sequence of SEQ ID NO:8 (encoding 5HTR4) or (iii) a nucleic acid comprising the sequence of SEQ ID NO:10 (encoding GPR139). Briefly, AAV vectors were produced by cotransfection of HEK293 cells with genome and packaging plasmids as described in Halbert et al., Nat. Biotechnol., 20:697-701 (2002). Vectors pseudotyped with AAV6 capsid were purified by use of a heparin column as described in Halbert et al., Methods Mol Biol, 1687:257-66 (2018). AAV vector titers were determined by quantitative PCR analysis.

Figure 5A:
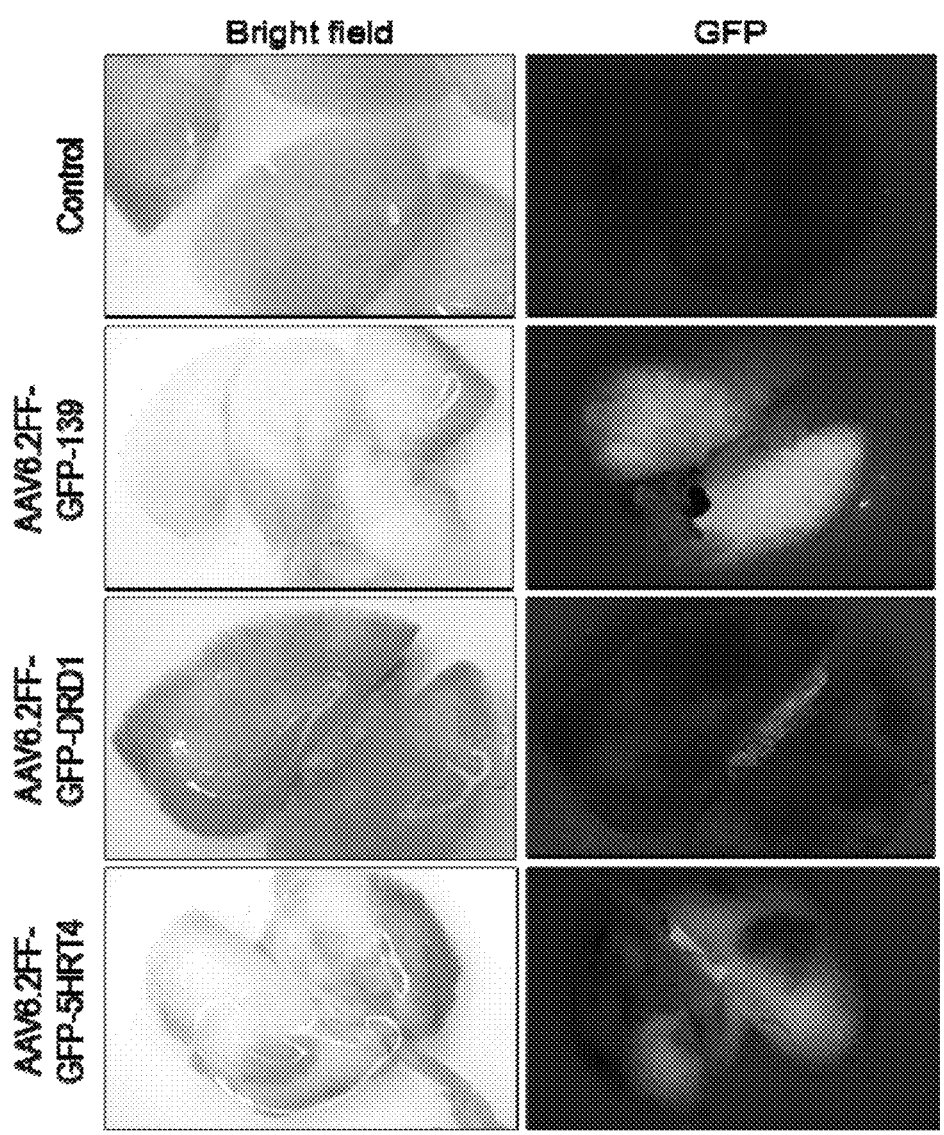
FIG. 5A depicts expression of GFP in whole lung 26 days after internasal administration of rAAV vectors comprising a capsid of serotype 6 and a nucleic comprising the sequence set forth as SEQ ID NO:6 (AAV6.2FF-GFP-DRD1), SEQ ID NO:8 (AAV6.2FF-GFP-5HTR4) or SEQ ID NO:10 (AAV6.2FF-GFP-139).
Figure 5B:
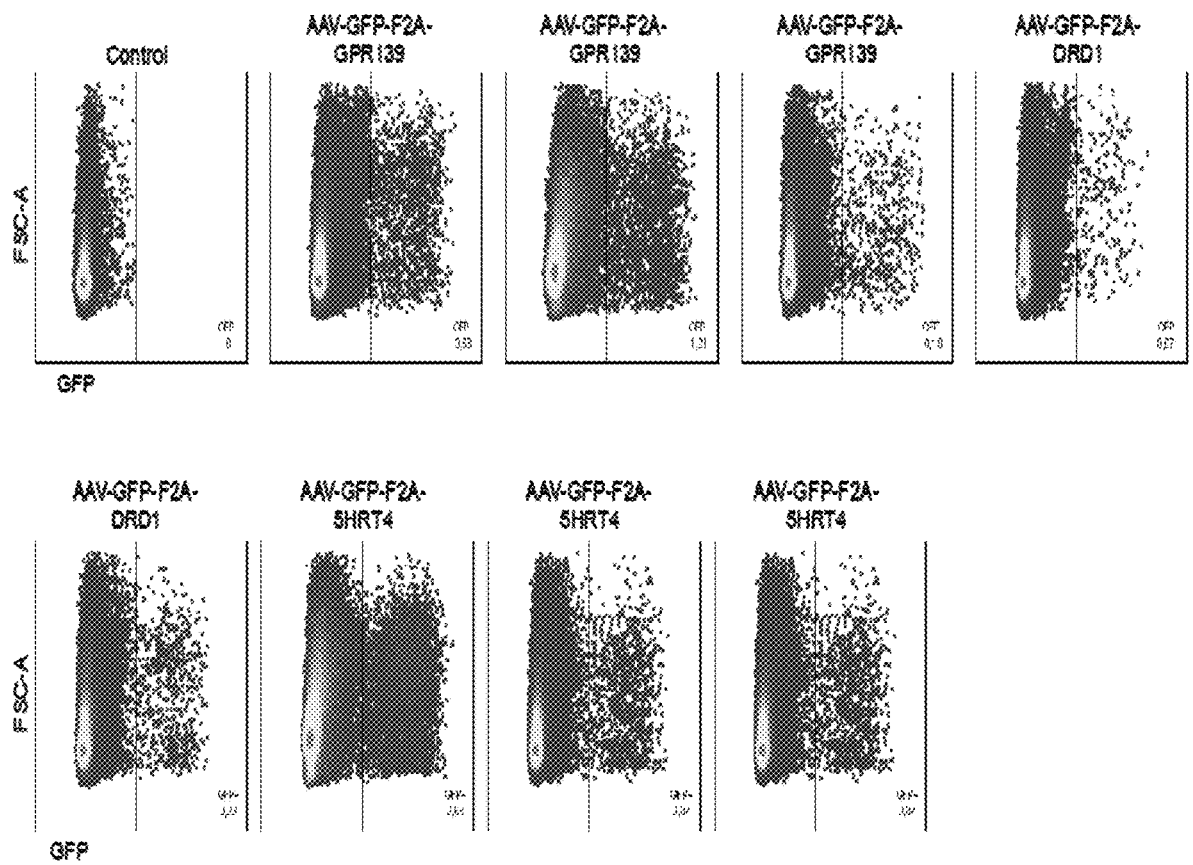
FIG. 5B illustrate the results of flow cytometric analysis of GFP positive lung cells from mice receiving the same treatment as in FIG. 5A.

Balb/c mice (n=4) were administered $1\times10^{11}$ vector genomes (vg) of each AAV vector intranasally. Twenty-six days later, mice were euthanized and exsanguinated. FIG. 5A illustrates imaging of lungs (perfused with PBS) with an inverted fluorescence microscope. FIG. 5B illustrates quantification of GFP-positive cells by flow cytometry following enzymatic digestion of lungs. Robust expression of the encoded proteins was observed in lungs following transduction with each rAAV population.

This data demonstrates that the nucleic acids and vectors described herein are useful for robust in vivo delivery of the encoded neuroreceptors.

While the materials and methods of this invention have been described in terms of preferred embodiments, it will be apparent to those of skill in the art that variations may be applied to the method described herein without departing from the concept, spirit and scope of the invention. All such similar substitutes and modifications apparent to those skilled in the art are deemed to be within the spirit, scope and concept of the invention.

The invention claimed is:

1. A nucleic acid codon optimized for expression in humans and encoding:
    (i) a human dopamine receptor D1 (DRD1) protein, the nucleic acid comprising the nucleotide sequence set forth as SEQ ID NO: 1 or comprising a nucleotide sequence at least 95% identical thereto;
    (ii) a human 5-Hydroxytryptamine receptor 4 (5HTR4) protein, the nucleic acid comprising the nucleotide sequence set forth as SEQ ID NO: 7 or comprising a nucleotide sequence at least 95% identical thereto; or
    (iii) a human G-protein coupled receptor 139 (GPR139) protein, the nucleic acid comprising the nucleotide sequence set forth as SEQ ID NO: 9 or comprising a nucleotide sequence at least 95% identical thereto.

2. The nucleic acid according to claim 1, the nucleic acid, comprising the nucleotide sequence set forth as any one of SEQ ID NOs:1-3.

3. An expression cassette comprising the nucleic acid according to claim 1 and an expression control sequence operably linked and heterologous to the nucleic acid sequence.

4. The expression cassette according to claim 3, wherein the expression control sequence is a constitutive promoter.

5. The expression cassette of claim 4, wherein the expression control sequence comprises a CASI promoter having, the nucleotide sequence set forth as SEQ ID NO:2 or a sequence at least 95% identical thereto.

6. The expression cassette according to claim 5, comprising from 5' to 3': (a) an AAV2 inverted terminal repeat (ITR)

(b) a CASI promoter (c) codon optimized DRD1 gene of SEQ ID NO:1, a codon optimized 5HTR4 gene of SEQ ID NO: 7 or a codon optimized GPR139 gene of SEQ ID NO:9 (d) an SV40 polyadenylation sequence and (e) an AAV2 ITR.

7. The expression cassette according to claim 6, wherein the 5' ITR comprises the sequence of SEQ ID NO:4 and the 3' ITR comprises the sequence of SEQ ID NO:5.

8. The expression cassette according to claim 6 further comprising a woodchuck hepatitis virus post-transcriptional regulatory element (WPRE) comprising the nucleotide sequence set forth as SEQ ID NO:3 or a sequence at least 95% identical thereto.

9. The expression cassette according to claim 6, comprising the nucleotide sequence of SEQ ID NO:6 or a sequence at least 90% identical thereto.

10. The expression cassette according to claim 6, comprising the nucleotide sequence of SEQ ID NO:8 or a sequence at least 90% identical thereto.

11. The expression cassette according to claim 6, comprising the nucleotide sequence of SEQ ID NO:10 or a sequence at least 90% identical thereto.

12. A vector comprising the expression cassette according to claim 3.

13. The vector of claim 12, wherein the vector is a recombinant adeno-associated (rAAV) vector.

14. The vector of claim 13, wherein the rAAV vector comprises an AAV capsid of serotype 2, 5, 6, 9 or rh10 or a variant thereof.

15. The vector of claim 14, wherein the rAAV vector comprises an AAV6 capsid or variant thereof.

16. The vector of claim 14, wherein the rAAV vector comprises a nucleic acid comprising from 5' to 3': (a) an AAV2 5' ITR (b) a CASI promoter (c) codon optimized eGFP sequence (d) F2A sequence (e) codon optimized DRD1 sequence (f) WPRE sequence (g) SV40 poly(A) sequence and (h) an AAV2 3' ITR.

17. The vector of claim 14, wherein the rAAV vector comprises a nucleic acid comprising from 5' to 3': (a) an AAV2 5' ITR (b) a CASI promoter (c) codon optimized eGFP sequence (d) F2A sequence (e) codon optimized 5HTR4 sequence (f) WPRE sequence (g) SV40 poly(A) sequence and (h) an AAV2 3' ITR.

18. The vector of claim 14, wherein the rAAV vector comprises a nucleic acid comprising from 5' to 3': (a) an AAV2 5' ITR (b) a CASI promoter (c) codon optimized eGFP sequence (d) F2A sequence (e) codon optimized GPR139 sequence (f) WPRE sequence (g) SV40 poly(A) sequence and (h) an AAV2 3' ITR.

19. A mammalian host cell comprising the expression cassette according to claim 3.

20. A composition comprising the expression cassette according to claim 3, and optionally a pharmaceutically acceptable excipient.

21. The composition according to claim 20, comprising an rAAV, said rAAV comprising a nucleic acid comprising the nucleotide sequence set forth as any one of SEQ ID NOs:6, 8 and 10 and an AAV capsid of serotype 2, 5, 6, 9 or rh10.

22. The composition according to claim 21, wherein the rAAV comprises a capsid of serotype 6.

23. A plasmid comprising a nucleotide sequence as set forth in any one of SEQ ID NOs: 6, 8 and 10 or a sequence at least 80% identical thereto.

24. The plasmid according to claim 23, which is a circular plasmid comprising a backbone sequence, said backbone sequence comprising an origin of replication, and a selection marker.

* * * * *